United States Patent
Takayanagi et al.

(10) Patent No.: US 12,168,781 B2
(45) Date of Patent: Dec. 17, 2024

(54) PRODUCTION METHOD FOR T CELLS OR NK CELLS, MEDIUM FOR CULTURING T CELLS OR NK CELLS, METHOD FOR CULTURING T CELLS OR NK CELLS, METHOD FOR MAINTAINING UNDIFFERENTIATED STATE OF UNDIFFERENTIATED T CELLS, AND GROWTH-ACCELERATING AGENT FOR T CELLS OR NK CELLS

(71) Applicants: KIRIN HOLDINGS KABUSHIKI KAISHA, Tokyo (JP); Kyoto University, Kyoto (JP)

(72) Inventors: Shinichiro Takayanagi, Tokyo (JP); Atsushi Kunisato, Tokyo (JP); Sayaka Chuganji, Tokyo (JP); Ken Fukumoto, Tokyo (JP); Kazuki Nakazono, Tokyo (JP); Shin Kaneko, Kyoto (JP); Yohei Kawai, Kyoto (JP)

(73) Assignees: KIRIN HOLDINGS KABUSHIKI KAISHA, Tokyo (JP); Kyoto University, Kyoto (JP)

( * ) Notice: Subject to any disclaimer, the term of this patent is extended or adjusted under 35 U.S.C. 154(b) by 727 days.

(21) Appl. No.: 17/311,001

(22) PCT Filed: Dec. 6, 2019

(86) PCT No.: PCT/JP2019/047808
§ 371 (c)(1),
(2) Date: Jun. 4, 2021

(87) PCT Pub. No.: WO2020/116606
PCT Pub. Date: Jun. 11, 2020

(65) Prior Publication Data
US 2022/0017867 A1    Jan. 20, 2022

(30) Foreign Application Priority Data
Dec. 6, 2018    (JP) .................................. 2018-229478

(51) Int. Cl.
| | | |
|---|---|---|
| *C12N 5/0783* | (2010.01) | |
| *C07D 215/00* | (2006.01) | |
| *C07D 217/22* | (2006.01) | |
| *C07D 471/18* | (2006.01) | |

(52) U.S. Cl.
CPC ......... *C12N 5/0646* (2013.01); *C07D 215/00* (2013.01); *C07D 217/22* (2013.01); *C07D 471/18* (2013.01); *C12N 5/0637* (2013.01); *C12N 2501/48* (2013.01); *C12N 2501/999* (2013.01)

(58) Field of Classification Search
CPC .. C12N 5/0646; C12N 5/0637; C12N 5/0636; C07D 215/00; C07D 217/22; C07D 471/18
See application file for complete search history.

(56) References Cited

U.S. PATENT DOCUMENTS

| | | |
|---|---|---|
| 2009/0305242 A1 | 12/2009 | Miyata et al. |
| 2012/0021519 A1 | 1/2012 | Ichida et al. |
| 2012/0171173 A1 | 7/2012 | Ideno et al. |
| 2013/0078226 A1 | 3/2013 | Nakauchi et al. |
| 2013/0178470 A1 | 7/2013 | Xu et al. |
| 2016/0202242 A1 | 7/2016 | Tanaka et al. |
| 2017/0009206 A1 | 1/2017 | Nakauchi et al. |
| 2018/0015123 A1 | 1/2018 | Choi et al. |
| 2019/0120824 A1 | 4/2019 | Jaques et al. |
| 2019/0330596 A1 | 10/2019 | Kaneko et al. |
| 2020/0277574 A1 | 9/2020 | Choi et al. |
| 2021/0032595 A1 | 2/2021 | Nakauchi et al. |

FOREIGN PATENT DOCUMENTS

| | | |
|---|---|---|
| CN | 101248192 A | 8/2008 |
| CN | 101273989 A | 10/2008 |
| CN | 101429201 A | 5/2009 |
| CN | 108064172 A | 5/2018 |
| CN | 108700568 A | 10/2018 |
| EP | 2 610 257 A1 | 7/2013 |
| JP | 2013-537171 A | 9/2013 |
| JP | 2018-502585 A | 2/2018 |
| WO | WO-2011/030851 A1 | 3/2011 |
| WO | WO-2011/096482 A1 | 8/2011 |
| WO | WO-2017/221975 A1 | 12/2017 |

OTHER PUBLICATIONS

Sojka, D. K.; et al. "Tissue-resident natural killer (NK) cells are cell lineages distinct from thymic and conventional splenic NK cells" 2014, eLife, vol. 3, e01659. (Year: 2014).*

Jia, X.- J.; et al. "Berbamine Exerts Anti-Inflammatory Effects via Inhibition of NF-κB and MAPK Signaling Pathways" 2017, Cellular Physiology and Biochemistry, vol. 41, pp. 2307-2318. (Year: 2017).*

Yuan, X.; et al. "Tetrandrine ameliorates collagen-induced arthritis in mice by restoring the balance between Th17 and Treg cells via the aryl hydrocarbon receptor" 2016, Biochemical Pharmacology, vol. 101, pp. 87-99. (Year: 2016).*

Granzin, M.; et al. "Highly efficient IL-21 and feeder cell-driven ex vivo expansion of human NK cells with therapeutic activity in a xenograft mouse model of melanoma" 2016, OncoImmunology, vol. 5, e1219007. (Year: 2016).*

Ho, et al., "Plant alkaloid tetrandrine downregulates protein kinase C-dependent signaling pathway in T cells", European Journal of Pharmacology 367: 389-398 (1999).

(Continued)

*Primary Examiner* — Eric Olson
*Assistant Examiner* — Benjamin M Brandsen
(74) *Attorney, Agent, or Firm* — Foley & Lardner LLP

(57) ABSTRACT

The present invention relates to a method for producing T cells or NK cells including culturing T cells or NK cells in a culture medium containing a CaMKII inhibitor such as a bisbenzylisoquinoline alkaloid compound. The disclosed compounds and methods can be used for maintaining the undifferentiated state of undifferentiated T cells, or for efficiently proliferating T cells or NK cells.

13 Claims, 23 Drawing Sheets

(56) References Cited

OTHER PUBLICATIONS

Office Action dated Sep. 29, 2021 issued in a corresponding Japanese Patent Application No. 2020-560042, (5 pages).
Extended European Search Report issued in corresponding European Patent Application No. EP19892251, dated Sep. 1, 2022.
Kubbies Manfred, et al., "Complex Ca2 flux 1,9,10 inhibition as primary mechanism of staurosporine-induced impairment of T cell activation", Eur. J. Immunol., Jan. 1, 1989, pp. 1393-1398.
Condiotti et al., "Ex vivo expansion of CD561 cytotoxic cells from human umbilical cord blood", Experimental Hematol.,29(1): 104-113, 2001.
Goodier et al., "Lipopolysaccharide Stimulates the Proliferation of Human CD56+CD3-NK Cell: A Regulatory Role of Monocytes and IL-10", The Journal of Immunology, 165(1): 139-147, 2000.
Granzin et al., "Shaping of Natural Killer Cell Antitumor Activity by Ex Vivo Cultivation", Frontiers Immunology, 8(458): 1-18, 2017.
Gu, Ying et al., "CaMKII y, a critical regulator of CML stem/progenitor cells, is a target of the natural product berbamine", Blood, 120(24): 4829-4839, 2012.
International Search Report and Written Opinion dated Mar. 10, 2020, issued in corresponding International Application No. PCT/JP2019/047808 (17 pages).
Li et al., "Human iPSC-derived Natural Killer Cells Engineered with Chimeric Antigen Receptors Enhance Anti-Tumor Activity", Cell Stem Cell, 23(2): 181-192 2018.
Liu et al., "The Effect of Berbamine on the Immunoregulation of BALB/c Mice", Journal of China Medical University, 1996, vol. 25, No. 3, pp. 229-231.
Nishimura T, et al., "Generation of rejuvenated Antigen-Specific T Cells by Reprogramming to Pluripotency and Redifferentiation", Cell Stem Cell 12, 114-126, Jan. 3, 2013.
Ono, Minoru, "Anti-tumor effects of cepharanthin—Mechanism of Antimetastatic effect on Lewis Lung Carcinoma" Jpn J Cancer Chemother, 1988, vol. 15, No. 2, pp. 249-255.
Porter et al., "Chimeric antigen receptor T cells persist and induce sustained remissions in relapsed refractory chronic lymphocytic leukemia", Science Translational Medicine. 7(303): 1-13, 2015.
Restifo, "Big bang theory of stem-like T cells confirmed", Blood, 124(4):476-477, Jul. 2014.
Takayama N, et al., "Transient activation of c-MYC expression is critical for efficient platelet generation from human induced pluripotent stem cells", Journal of Experimental Medicine, 207(13): 2817-2830, 2010.
Kubbies Manfred, et al., "Complex Ca2 flux inhibition as primary mechanism of staurosporine-induced impairment of T cell activation", Eur. J. Immunol., Jan. 1, 1989, pp. 1393-1398.
Office Action issued in corresponding Japanese Patent Application No. 2022-003212 dated Nov. 7, 2023 (9 pages).
Oyaizu et al., "Protection of T cells from radiation-induced apoptosis by Cepharanthin", International Immunopharmacology, Elsevier, Jun. 27, 2001, vol. 1, pp. 2091-2099.
Ebert et al., "MAP Kinase Inhibition Promotes T Cell and Antitumor Activity in Combination with PD-L1 Checkpoint Blockade", Immunity, CellPress, vol. 44, No. 03, Mar. 15, 2016, pp. 609-621.
Office Action issued in corresponding Chinese Patent Application No. 201980080762.8 dated Jan. 11, 2024 (78 pages).
Ren, Huayi, "Handbook of Clinical Practical Tumor Drugs", Ed., Lake Science and Technology, Jan. 31, 1998, pp. 238-239.
Office Action issued in corresponding Japanese Patent Application No. 2022-003212 dated Jul. 2, 2024 (7 pages).
Office Action issued in corresponding Chinese Patent Application No. 201980080762.8 dated Sep. 21, 2024 (23 pages).

* cited by examiner

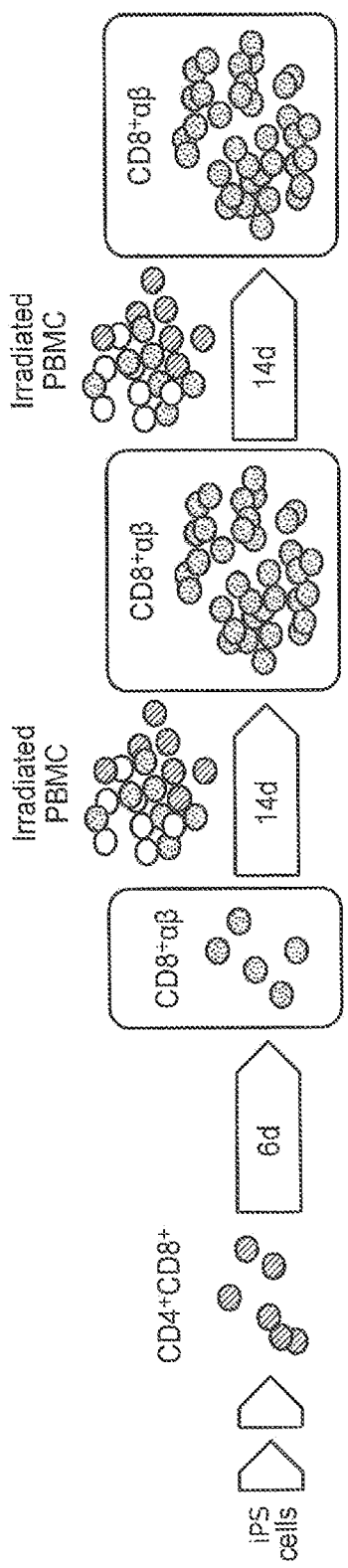
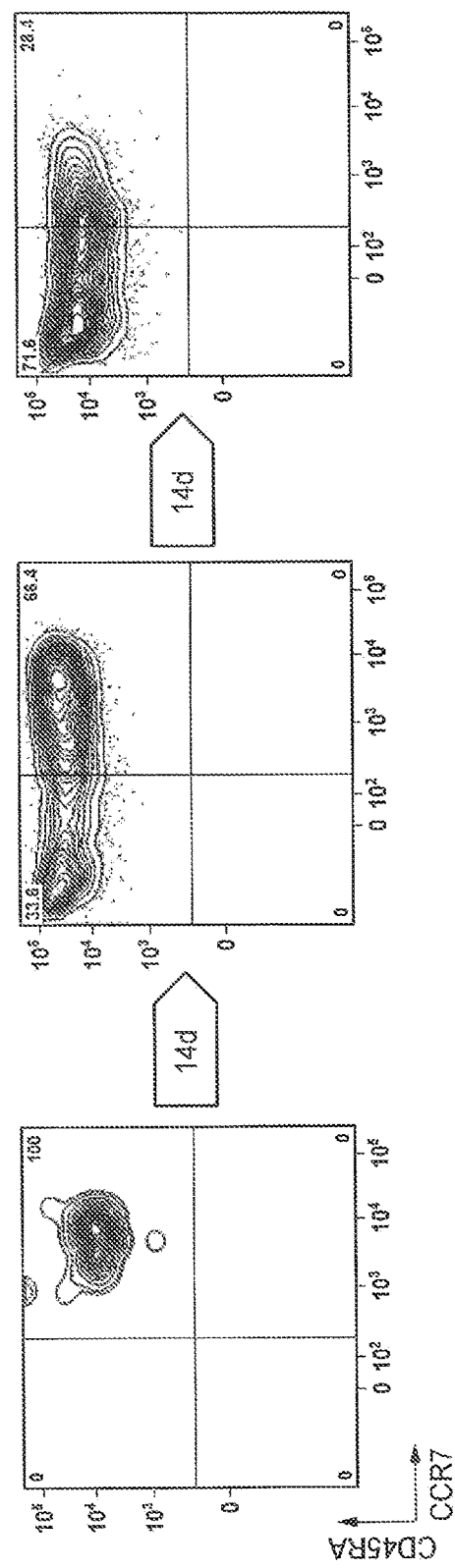
Fig. 4

Fig. 12
(A)
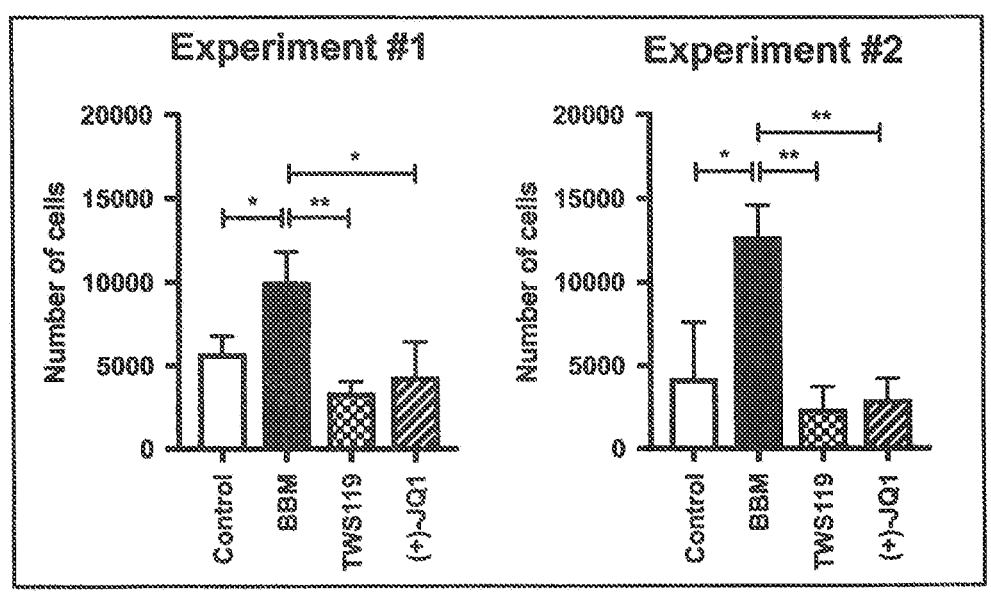
(B)
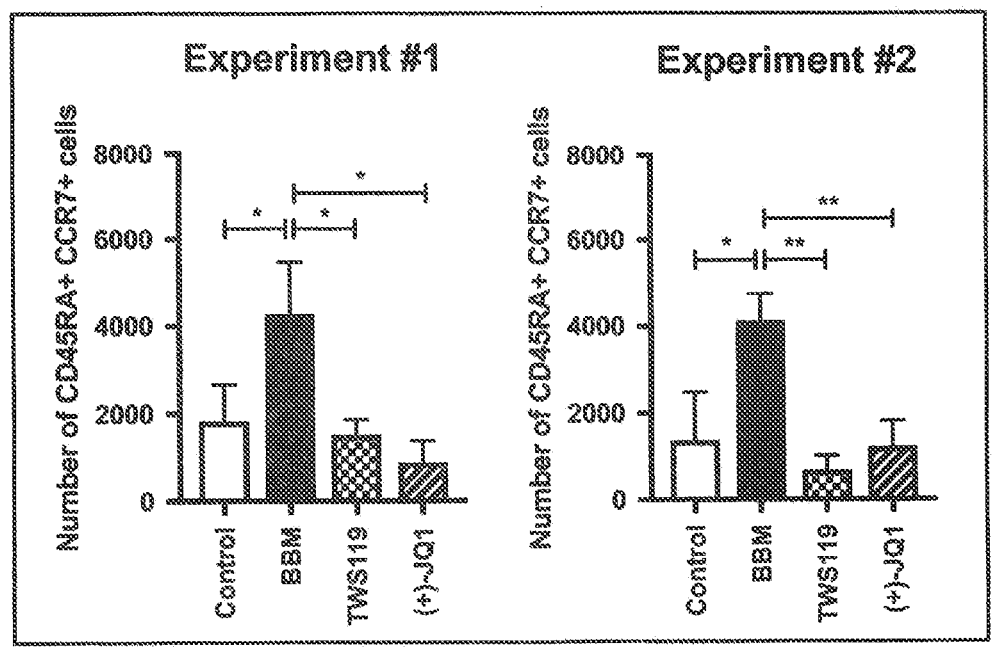

Fig. 14
(A)
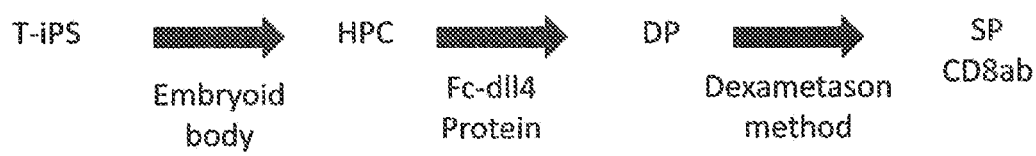
(B)
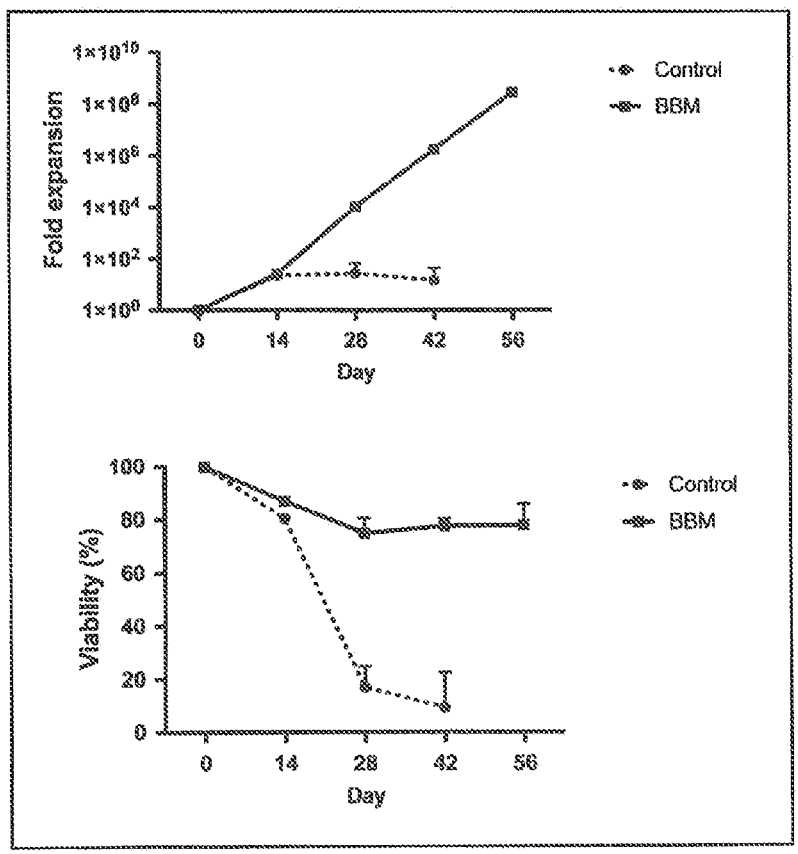

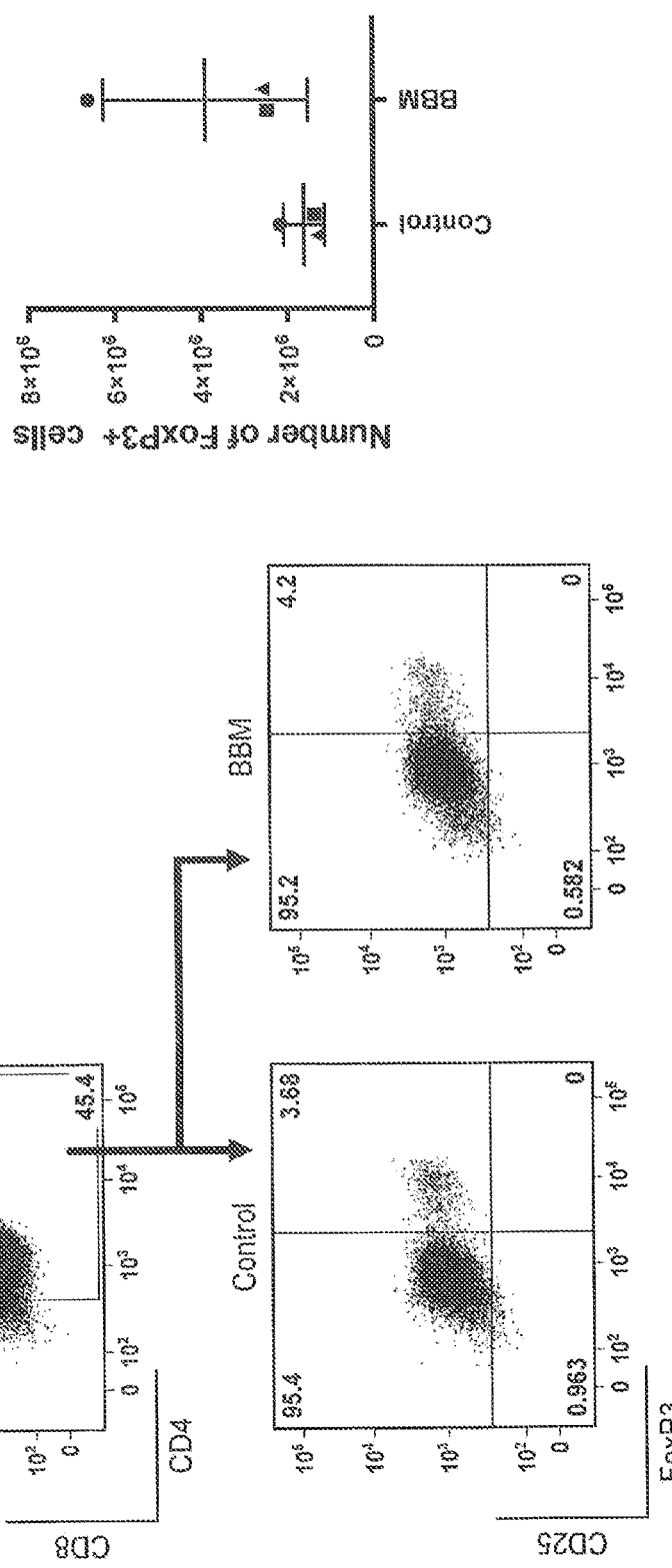
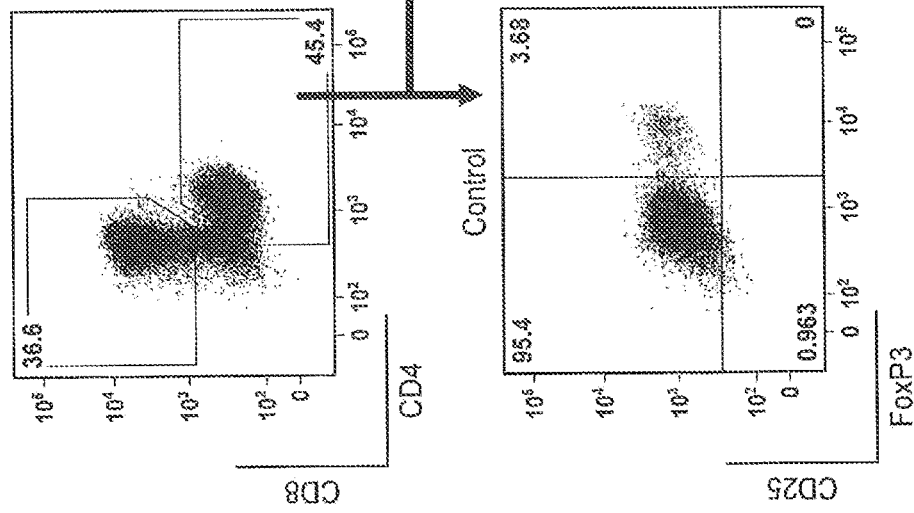
Fig. 17

Fig. 19
(A)
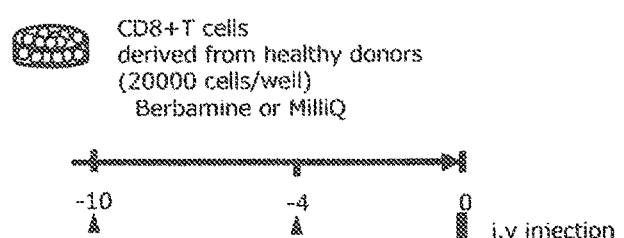
(B)
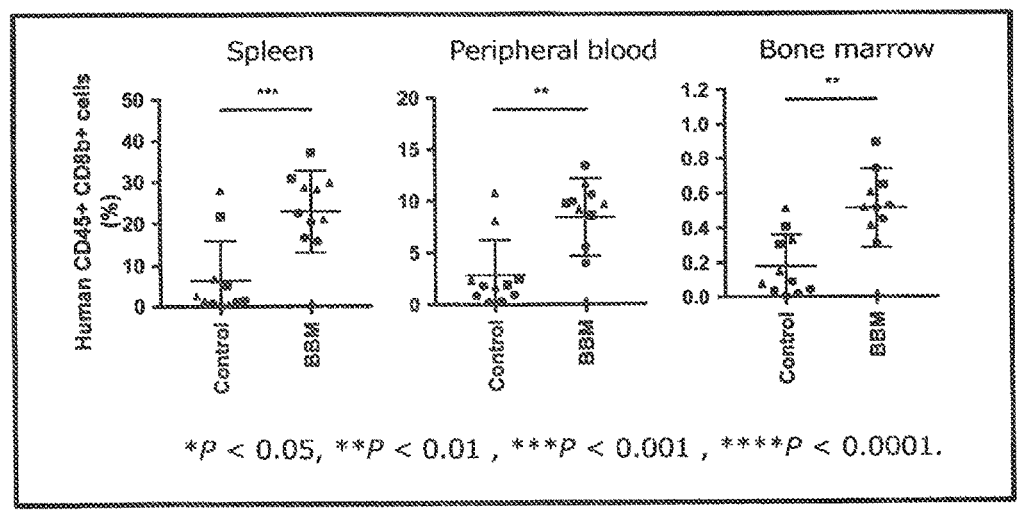

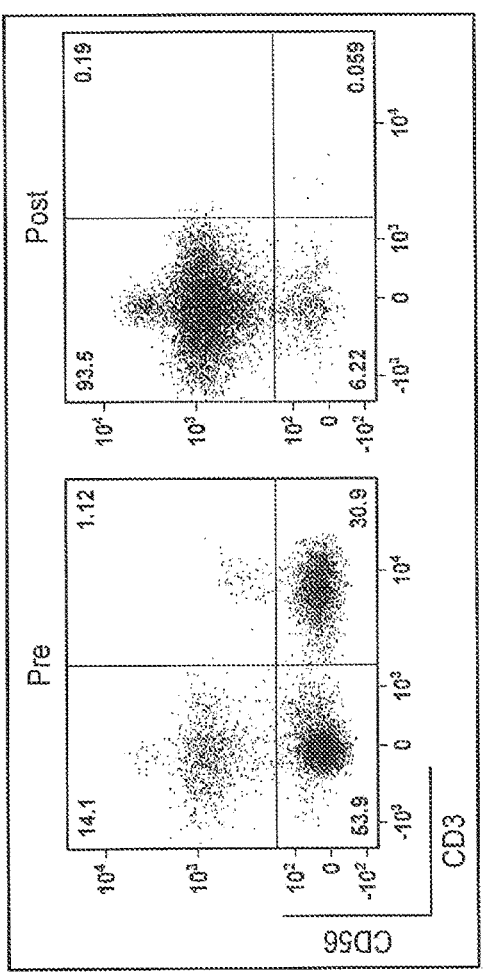
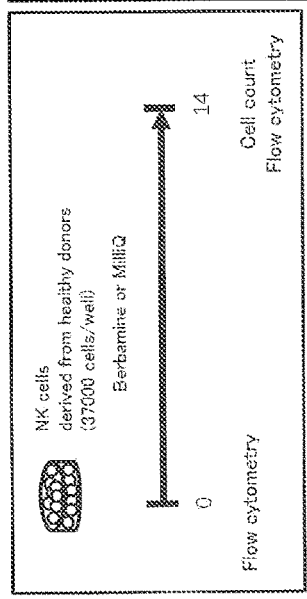
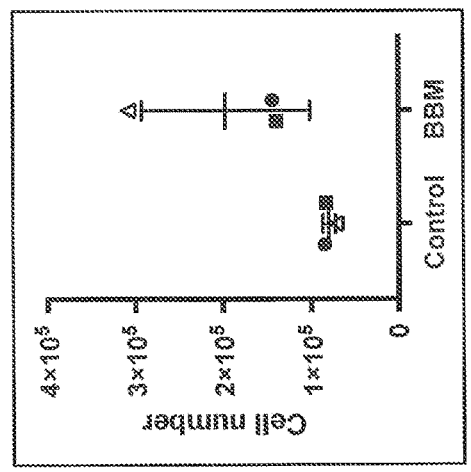
Fig. 20

PRODUCTION METHOD FOR T CELLS OR NK CELLS, MEDIUM FOR CULTURING T CELLS OR NK CELLS, METHOD FOR CULTURING T CELLS OR NK CELLS, METHOD FOR MAINTAINING UNDIFFERENTIATED STATE OF UNDIFFERENTIATED T CELLS, AND GROWTH-ACCELERATING AGENT FOR T CELLS OR NK CELLS

CROSS-REFERENCE TO RELATED APPLICATIONS

The present application claims priority under 37 U.S.C. § 371 to International Patent Application No. PCT/JP2019/047808, filed Dec. 6, 2019, which claims priority to and the benefit of Japanese Patent Application No. 2018-229478, filed on Dec. 6, 2018. The contents of these applications are hereby incorporated by reference in their entireties.

TECHNICAL FIELD

The present invention relates to a method for producing T cells or NK cells, a culture medium for culturing T cells or NK cells, a method for culturing T cells or NK cells, a method for maintaining the undifferentiated state of undifferentiated T cells, and a growth promoter for T cells or NK cells.

BACKGROUND ART

T cells are one of the immune cells derived from hematopoietic stein cells. T cells express a T cell receptor (TCR) on the cell surface and specifically recognize an HLA-peptide complex on a target cell. In addition, T cells can proliferate with a proliferative signal via TCR. T cells are roughly classified into helper T cells (Th cells) and cytotoxic T cells (CTLs), and work in cooperation in the body.

The immune response to tumors (anti-tumor immune response) is mainly composed of CTLs that directly damage tumors and Th cells that enhance the function of CTLs. On the other hand, it is considered that dendritic cells (DCs) have a role as a control tower that regulates the dynamics of other immune cells, and Th cells activate CTLs through activation of DCs and exhibit an antitumor effect.

In a method for treating cancer using an anti-tumor immune response, an adoptive immunotherapy using CTLs or the like specific to a tumor-related antigen that functions as effector cells is a therapeutic method that also exhibits an effect on regression of primary cancer, and suppression of metastasis or recurrence thereof, and has few side effects on normal tissues.

It is considered that among adoptive immunotherapies, T cells induced from pluripotent stem cells such as induced pluripotent stem (iPS) cells lead to cellular immunotherapy that induces a strong antitumor immune response when administered in vivo, and development has proceeded (PTL 1, NPL 1). For example, the methods described in PTL 1 and NPL 1 are methods in which iPS cells are produced from antigen-specific CD8-positive CTLs, and redifferentiation into CD8-positive CTLs is induced.

In T cells induced from pluripotent stem cells, high persistence in vivo correlates with response (NPL 3), and as T cells are in a more undifferentiated state, a higher therapeutic effect is exhibited (NPL 4).

However, in the culturing of T cells induced from pluripotent stem cells, in general, cells derived from a healthy donor or the like are used as feeder cells, but there is a fear of contamination with an unknown component at an unknown concentration, a risk of infection, or a problem of cost, which is a problem in clinical application (NPL 2).

Natural killer (NK) cells account for about 10% of blood cells, and are one of the lymphocytes that play an important role in immunoreaction. NK cells can perform various functions, but in particular have an ability to kill a cancer cell or a cell infected with a pathogen or a virus having invaded from the outside, or the like, and play a role in removing an abnormal cell that has undergone neoplastic transformation or is undergoing neoplastic transformation.

Further, NK cells also function as effector cells when an antibody drug recognizes a tumor cell or the like and exhibits an antibody-dependent cellular cytotoxicity activity in the body of a patient. Similarly to T cells, NK cells can be given specificity by introducing a chimeric antigen receptor (CAR) or TCR, and can exhibit a cytotoxicity activity specific to a cancer cell or the like (NPL 5).

Despite the possibility of NK cells as a therapeutic agent for cancer or an infectious disease as described above, the number of NK cells present in the body of a patient is not large. Therefore, there has been a demand for a technique capable of mass-producing NK cells while maintaining sufficient efficacy to such an extent that the cells can be used in therapeutic applications.

However, NK cells cannot be proliferated nor cultured in a large amount in vitro as compared with T cells, and therefore, many studies have been conducted for techniques for proliferating and culturing NK cells to a therapeutically useful level.

For example, with respect to the culturing of NK cells, studies of a proliferation or activation method using IL-21, LPS (NPL 6), or an OKT-3 antibody (NPL 7) that stimulates CD3 as well as IL-2 that has been used for T cell proliferation/activity have been conducted. However, these merely found a new proliferative substance in the form of variation and development of use of conventionally used IL-2.

Further, a method for culturing NK cells in which IL-12, IL-15, or IL-18 is combined has also been developed (NPL 8). In addition, a method using autologous or allogeneic feeder cells for culturing NK cells has also been developed.

However, an innovative method for proliferating NK cells using a low-molecular weight compound or the like, which is excellent in terms of quality control, safety, cost, etc., has not yet been found out.

A bisbenzylisoquinoline alkaloid is a low-molecular weight compound derived from a naturally occurring medicinal material. Among the bisbenzylisoquinoline alkaloids, for example, berbamine or the like has been used as a clinical medicine.

Berbamine is one of the components of a cepharanthine preparation, and is known to have a cytostatic effect on a cancer cell and exhibit an antitumor effect (NPL 9). It is also known that berbamine has an effect of stimulating the proliferation of myeloid cells, improving the level of a hematopoietic stem cell colony stimulating factor (GCSF), promoting the proliferation of myeloid hematopoietic stem cells and myeloid progenitor cells and their differentiation into granulocytes, and promoting the proliferation of leukocytes. (PTL 2).

CITATION LIST

Patent Literature (PTL)

PTL 1: WO 2011/096482
PTL 2: JP-T-2013-537171

Non Patent Literature (NPL)

NPL 1: Nishimura T, et al., Cell Stem Cell. 12(1): 114-126, 2013
NPL 2: Takayama N, et al., Journal of Experimental Medicine, 207(13): 2817-2830, 2010
NPL 3: Porter et al., Science Translational Medicine. 7(303): 303ra139, 2015
NPL 4: Nicholas P. Restifo, Blood. 124(4): 476-477, 2014
NPL 5: Li Y, et al., Cell Stem Cell, 23(2): 181-192, 2018
NPL 6: J. Immunol., 165(1): 139-147, 2000
NPL 7: Experimental Hematol., 29(1): 104-113, 2001
NPL 8: Front. Immunol., 8(458): 1-18, 2017
NPL 9: Ying Gu et al., Blood, 120(24): 4829-4839, 2012

SUMMARY OF INVENTION

Technical Problem

As described above, there has been a demand for a technique capable of mass-producing T cells or NK cells while maintaining sufficient efficacy to such an extent that the cells can be used in therapeutic applications. However, the above-mentioned known methods are merely in the form of variation and development of use of conventionally used IL-2 or the like, and an innovative proliferation or activation method achieving a level applicable to therapy has not yet been found out. On the other hand, an effect of promoting the proliferation of T cells or NK cells and an effect of maintaining the state of the cells (for example, undifferentiated property) of a bisbenzylisoquinoline alkaloid such as berbamine have not been known so far.

An object of the present invention is to provide a method for producing T cells or NK cells, a culture medium for culturing T cells or NK cells, a method for culturing T cells, a method for maintaining the undifferentiated state of undifferentiated T cells, and a growth promoter for T cells or NK cells, which are capable of efficiently proliferating T cells or NK cells and maintaining the state of the cells (for example, undifferentiated property).

Solution to Problem

The present inventors conducted intensive studies in order to achieve the above object, and as a result, they found that a bisbenzylisoquinoline alkaloid represented by formula (X-1) or (X-2) or a compound resulting from cleavage of one ether bond thereof or a pharmaceutically acceptable salt thereof has an excellent proliferation promoting effect on T cells or NK cells and an excellent effect of maintaining the state of the cells (for example, undifferentiated property), and thus completed the present invention.

That is, the present invention provides the following inventions.

1. A method for producing T cells or NK cells, including culturing T cells or NK cells in a culture medium containing a bisbenzylisoquinoline alkaloid represented by the following formula (X-1) or formula (X-2) or a compound resulting from cleavage of one ether bond thereof or a pharmaceutically acceptable salt thereof.

[Chem. 1]

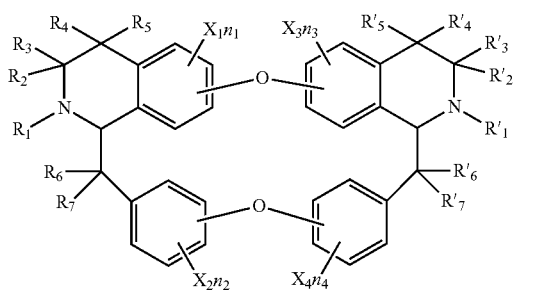

(X-1)

[Chem. 2]

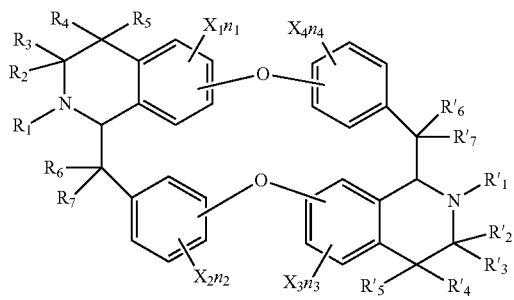

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

2. The production method according to the above 1, wherein the T cells or the NK cells are T cells or NK cells for immune cell therapy.

3. The production method according to the above 1 or 2, wherein the T cells or the NK cells are peripheral blood-derived, primary hematopoietic stem and progenitor cell-derived, or pluripotent stem cell-derived cells.

4. The production method according to any one of the above 1 to 3, wherein the T cells are undifferentiated T cells.

5. The production method according to any one of the above 1 to 4, wherein the T cells express at least one of CD4 and CD8.

6. The production method according to any one of the above 1 to 5, wherein the T cells are cells selected from the group consisting of helper T cells, regulatory T cells, cytotoxic T cells, naive T cells, memory T cells, and terminal effector T cells.

7. The production method according to the above 6, wherein the regulatory T cells express FoxP3.

8. The production method according to the above 6, wherein the memory T cells are stem cell memory T cells, central memory T cells, or effector memory T cells.

9. The production method according to any one of the above 1 to 3, wherein the NK cells are immature NK cells or mature NK cells.

10. The production method according to any one of the above 1 to 9, wherein the bisbenzylisoquinoline alkaloid or the compound resulting from cleavage of one ether bond thereof or the pharmaceutically acceptable salt thereof is at least one of berbamine, (+)-berbamine, E6-berbamine, cepharanthine, and a pharmaceutically acceptable salt thereof.

11. The production method according to any one of the above 1 to 10, wherein the concentration of the bisbenzylisoquinoline alkaloid or the compound resulting from cleavage of one ether bond thereof or the pharmaceutically acceptable salt thereof in the culture medium is from 0.1 nM to 10 μM.

12. The production method according to any one of the above 1 to 11, wherein the culture medium further contains a MAPK cascade inhibitor.

13. The production method according to any one of the above 1 to 12, wherein feeder cells are not contained in the culture medium.

14. The production method according to any one of the above 1 to 13, wherein the culturing period is 50 days or more.

15. T cells or TK cells produced by the production method according to any one of the above 1 to 14.

16. An immune cell therapeutic agent, containing the T cells or the TK cells according to the above 15.

17. A culture medium for culturing T cells or NK cells, containing a bisbenzylisoquinoline alkaloid represented by the following formula (X-1) or formula (X-2) or a compound resulting from cleavage of one ether bond thereof or a pharmaceutically acceptable salt thereof.

[Chem. 3]

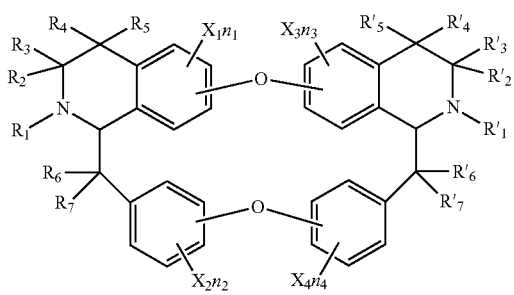

(X-1)

-continued

[Chem. 4]

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

18. The culture medium according to the above 17, wherein the T cells or the NK cells are peripheral blood-derived, primary hematopoietic stem and progenitor cell-derived, or pluripotent stem cell-derived cells.

19. The culture medium according to the above 17 or 18, wherein the bisbenzylisoquinoline alkaloid or the compound resulting from cleavage of one ether bond thereof or the pharmaceutically acceptable salt thereof is at least one of berbamine, (+)-berbamine, E6-berbamine, cepharanthine, and a pharmaceutically acceptable salt thereof.

20. The culture medium according to any one of the above 17 to 19, wherein the concentration of the bisbenzylisoquinoline alkaloid or the compound resulting from cleavage of one ether bond thereof or the pharmaceutically acceptable salt thereof is from 0.1 nM to 10 μM.

21. The culture medium according to any one of the above 17 to 20, further containing a MAPK cascade inhibitor.

22. A method for culturing T cells or NK cells, including culturing T cells or NK cells in a culture medium containing a bisbenzylisoquinoline alkaloid represented by the following formula (X-1) or formula (X-2) or a compound resulting from cleavage of one ether bond thereof or a pharmaceutically acceptable salt thereof.

[Chem. 5]

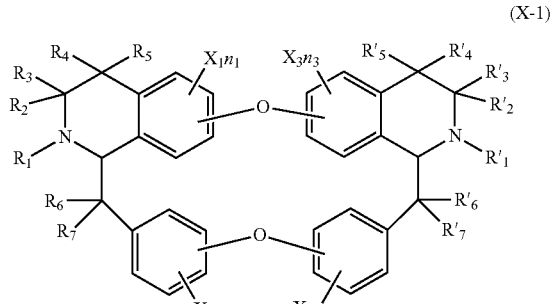

(X-1)

[Chem. 6]

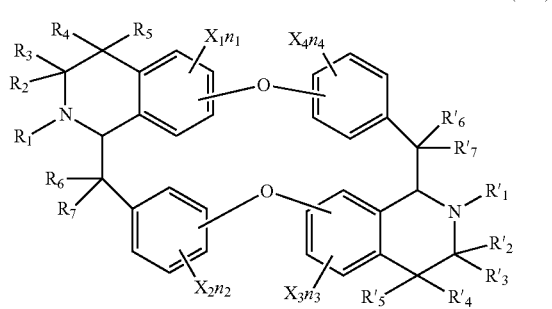

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

23. The culturing method according to the above 22, wherein the T cells or the NK cells are peripheral blood-derived, primary hematopoietic stem and progenitor cell-derived, or pluripotent stem cell-derived cells.

24. The culturing method according to the above 22 or 23, wherein the bisbenzylisoquinoline alkaloid or the compound resulting from cleavage of one ether bond thereof or the pharmaceutically acceptable salt thereof is at least one of berbamine, (+)-berbamine, E6-berbamine, cepharanthine, and a pharmaceutically acceptable salt thereof.

25. The culturing method according to any one of the above 22 to 24, wherein the concentration of the bisbenzylisoquinoline alkaloid or the compound resulting from cleavage of one ether bond thereof or the pharmaceutically acceptable salt thereof in the culture medium is from 0.1 nM to 10 μM.

26. A method for maintaining the undifferentiated state of undifferentiated T cells, including culturing undifferentiated T cells in a culture medium containing a bisbenzylisoquinoline alkaloid represented by the following formula (X-1) or formula (X-2) or a compound resulting from cleavage of one ether bond thereof or a pharmaceutically acceptable salt thereof.

[Chem. 7]

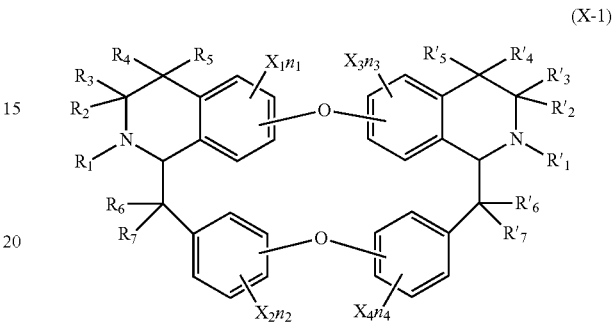

(X-1)

[Chem. 8]

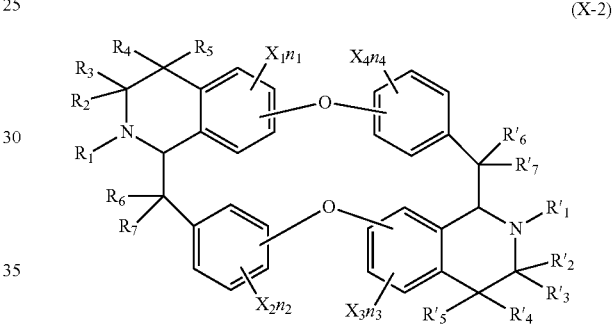

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

27. A growth promoter for T cells or NK cells, containing a bisbenzylisoquinoline alkaloid represented by the following formula (X-1) or formula (X-2) or a compound resulting from cleavage of one ether bond thereof or a pharmaceutically acceptable salt thereof as an active ingredient.

[Chem. 9]

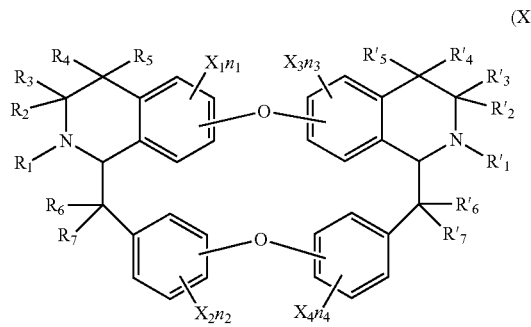

(X-1)

[Chem. 10]

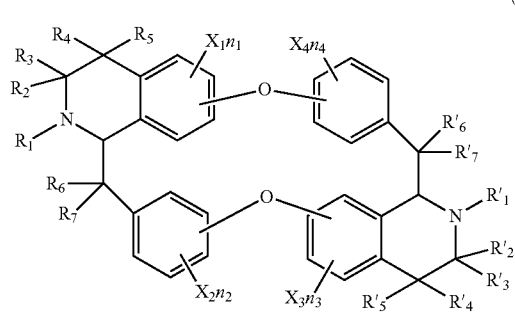

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

28. A method for producing T cells or NK cells, including culturing T cells or NK cells in a culture medium containing a CaMKII inhibitor.

29. The production method according to the above 28, wherein the CaMKII inhibitor is a bisbenzylisoquinoline alkaloid represented by the following formula (X-1) or formula (X-2) or a compound resulting from cleavage of one ether bond thereof or a pharmaceutically acceptable salt thereof.

[Chem. 11]

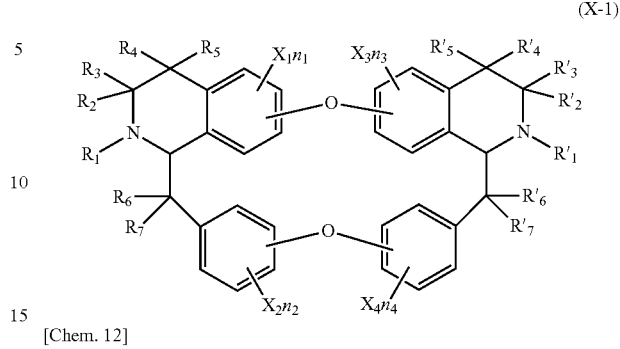

(X-1)

[Chem. 12]

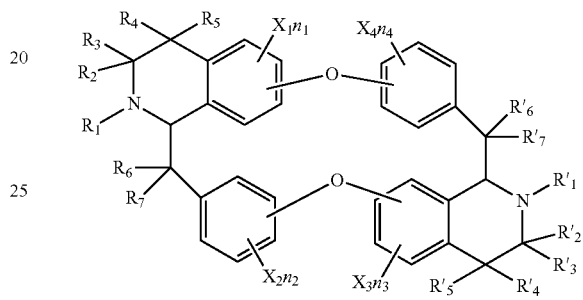

(X-2)

[In the formula (X-1) and the formula (X-2), $R_1$ and $R'_1$ are each independently H or straight-chain or branched-chain alkyl having 1 to 10 carbon atoms, $R_2$, $R'_2$, $R_3$, $R'_3$, $R_4$, $R'_4$, $R_5$, and $R'_5$ are each independently H, acyl, straight-chain or branched-chain alkyl having 1 to 10 carbon atoms, and the alkyl may be interrupted by an O, N, or S heteroatom, or $R_2$ and $R_3$, $R_4$ and $R_5$, $R'_2$ and $R'_3$, or $R'_4$ and $R'_5$ together represent O or S, $R_6$, $R'_6$, $R_7$, and $R'_7$ are each independently H, acyl, or straight-chain or branched-chain alkyl having 1 to 10 carbon atoms, and the alkyl may be interrupted by an O, N, or S heteroatom, or $R_6$ and $R_7$ or $R'_6$ and $R'_7$ together represent O or S, and $X_1$, $X_2$, $X_3$, and $X_4$ may be the same or different, and are each independently H, hydroxy, straight-chain or branched-chain alkyl having 1 to 10 carbon atoms, alkoxy, acyloxy, or sulfonyloxy, and each may further have a substituent, $n_1$ and $n_3$ are each independently an integer of 0 to 3, $n_2$ and $n_4$ are each independently an integer of 0 to 4, and these may be linked to each other to form a ring.]

Advantageous Effects of Invention

According to the present invention, T cells or TK cells can be efficiently proliferated while maintaining the state of the cells (for example, undifferentiated property) by culturing T cells or TK cells in the presence of a bisbenzylisoquinoline alkaloid represented by formula (X-1) or formula (X-2) or a compound resulting from cleavage of one ether bond thereof or a pharmaceutically acceptable salt thereof. Therefore, according to the present invention, a method for producing T cells or NK cells, a culture medium for culturing T cells or NK cells, a method for culturing T cells or NK cells, a method for maintaining the undifferentiated state of undifferentiated T cells, and a growth promoter for T cells or NK cells, which are capable of producing T cells or NK cells that exhibit excellent in vivo persistence more safely at low cost, are provided.

BRIEF DESCRIPTION OF DRAWINGS

FIG. 4(A) shows a schematic view of a procedure for an immunophenotyping test using T-iPS-T cells, and FIG. 4(B) shows the results.

FIGS. 12(A) and 12(B) show the results of evaluation of the effect on culturing of T-iPS-T cells by comparison of a known compound that contributes to the proliferation of memory T cells with berbamine.

FIG. 14(A) shows an experimental scheme of evaluation of feeder-free long-term culturing of T-iPS-T cells using berbamine, and FIG. 14(B) shows the results.

FIGS. 17(A) and 17(B) show the results of verification of the usefulness of berbamine in the proliferation of regulatory T cells (Treg).

FIG. 19(A) shows an experimental scheme of examination of the effect of cells cultured with berbamine on engraftment into mice, and FIG. 19(B) shows the results.

FIG. 20(A) shows an experimental scheme of examination of the effect of berbamine on NK cells, and FIGS. 20(B) and 20(C) show the results. FIG. 20(B) shows FACS plots before and after purification of NK cells. FIG. 20(C) shows the number of cells after culturing.

DESCRIPTION OF EMBODIMENTS

Figure 1:
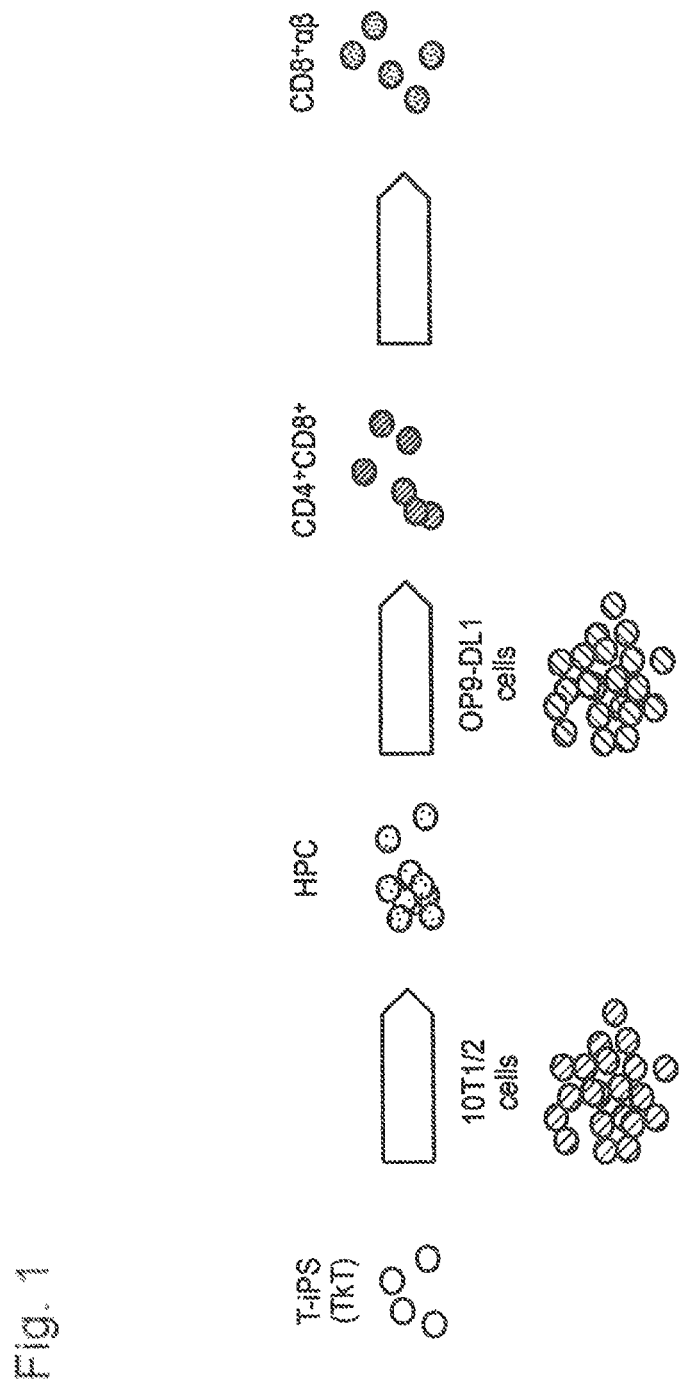
FIG. 1 shows a schematic view of a procedure for inducing the differentiation of iPS cells.

[Method for Producing T Cells or NK Cells]

The method for producing T cells or NK cells according to the present invention includes a step of culturing T cells or NK cells in a culture medium containing a bisbenzylisoquinoline alkaloid represented by formula (X-1) or formula (X-2) or a compound resulting from cleavage of one ether bond thereof or a pharmaceutically acceptable salt thereof (hereinafter, also referred to as culture medium for culturing T cells or NK cells according to the present invention).

[Bisbenzylisoquinoline Alkaloid Represented by Formula (X-1) or Formula (X-2)]

The bisbenzylisoquinoline alkaloid represented by the following formula (X-1) or (X-2) or the compound resulting from cleavage of one ether bond thereof in the present invention will be described.

[Chem. 13]

(X-1)

[Chem. 14]

(X-2)

In the formulae (X-1) and (X-2), $R_1$ and $R'_1$ are each independently H or straight-chain or branched-chain alkyl having 1 to 10 carbon atoms, R$_2$, R'$_2$, R$_3$, R'$_3$, R$_4$, R'$_4$, R$_5$, and R'$_5$ are each independently H, acyl, straight-chain or branched-chain alkyl having 1 to 10 carbon atoms, and the alkyl may be interrupted by an O, N, or S heteroatom, or R$_2$ and R$_3$, R$_4$ and R$_5$, R'$_2$ and R'$_3$, or R'$_4$ and R'$_5$ together represent O or S, R$_6$, R'$_6$, R$_7$, and R'$_7$ are each independently H, acyl, or straight-chain or branched-chain alkyl having 1 to 10 carbon atoms, and the alkyl may be interrupted by an O, N, or S heteroatom, or R$_6$ and R$_7$ or R'$_6$ and R'$_7$ together represent O or S, and X$_1$, X$_2$, X$_3$, and X$_4$ may be the same or different, and are each independently H, hydroxy, straight-chain or branched-chain alkyl having 1 to 10 carbon atoms, alkoxy, acyloxy, or sulfonyloxy, and each may further have a substituent, n$_1$ and n$_3$ are each independently an integer of 0 to 3, n$_2$ and n$_4$ are each independently an integer of 0 to 4, and these may be linked to each other to form a ring.

In the present invention, the acyl refers to RC(=O)—, and R may be any of straight-chain or branched-chain alkyl having 1 to 10 carbon atoms, aryl, or a heterocycle, which may further have a substituent.

In the present invention, the acyloxy refers to RC(=O)O—, and R is the same as described above.

In the present invention, the sulfonyloxy refers to RS(=O)$_2$O—, and R is the same as described above.

In the present invention, as the additional substituent when acyl, acyloxy or sulfonyloxy, or X$_1$, X$_2$, X$_3$, or X$_4$ further has a substituent, for example, straight-chain or branched-chain alkyl having 1 to 10 carbon atoms, aryl, or a heterocycle, a halogen, amino, an amine, nitro, hydroxy, a substituent represented by a structural formula shown below, or the like is exemplified.

[Chem. 15]

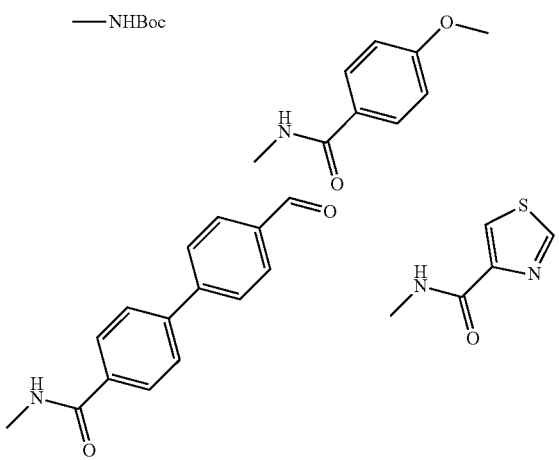

Boc denotes tert-butoxycarbonyl. In addition, among these, the aryl or the heterocycle may further have a substituent such as straight-chain or branched-chain alkyl having 1 to 10 carbon atoms, a halogen, amino, an amine, nitro, or hydroxy.

One of the ether bonds at two sites in the above formula (X-1) or (X-2) may be cleaved.

Further, a quaternary N ion compound in which one or two tertiary N atoms included in an isoquinoline backbone in the above formula (X-1) or (X-2) are further modified with straight-chain or branched-chain alkyl having 1 to 10 carbon atoms or aryl is also included in the bisbenzylisoquinoline alkaloid of the present invention. Examples of the quaternary N ion compound include compounds represented by the following formula (X-3) or (X-4), or the like.

[Chem. 16]

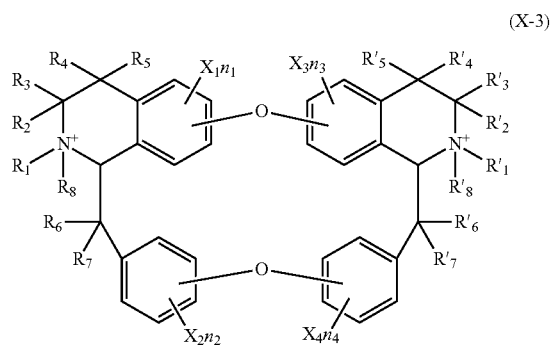

[Chem. 17]

(X-4)

R$_1$ to R$_7$, R'$_1$ to R'$_7$, X$_1$ to X$_4$, and n$_1$ to n$_4$ in the formula (X-3) or the formula (X-4) have the same definitions as those in the formula (X-1) and the formula (X-2), respectively. Further, in the formula (X-3) and the formula (X-4), R$_8$ and R'$_8$ are each independently H or straight-chain or branched-chain alkyl having 1 to 10 carbon atoms or aryl.

Examples of the bisbenzylisoquinoline alkaloid represented by the formula (X-1) to formula (X-4) include compounds represented by the following formula (I) to formula (V), respectively.

[Chem. 18]

(I)

[Chem. 19]

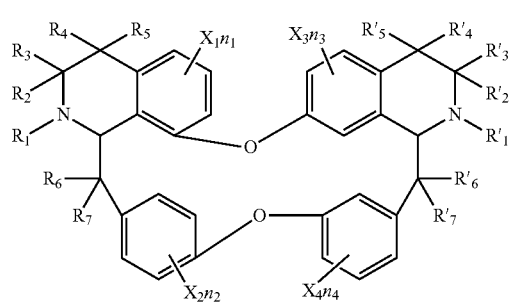

(II)

[Chem. 20]

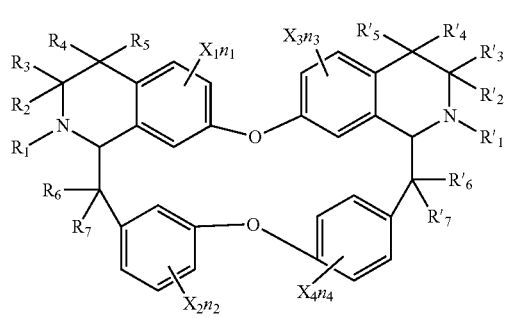

(III)

[Chem. 21]

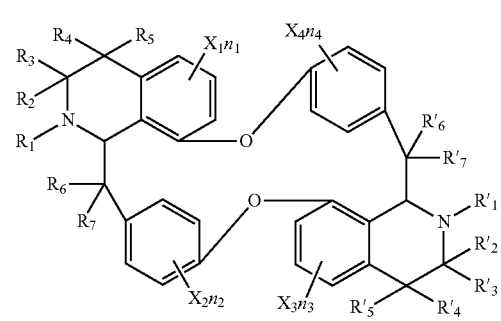

(IV)

[Chem. 22]

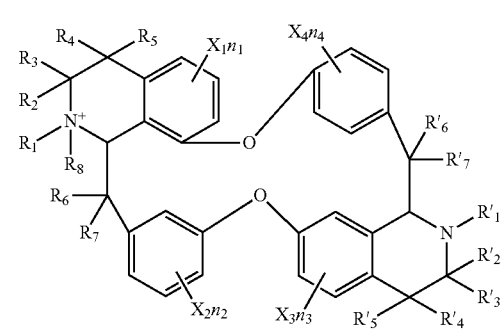

(V)

$R_1$ to $R_8$, $R'_1$ to $R'_7$, $X_1$ to $X_4$, and $n_1$ to $n_4$ in the formula (I) to the formula (V) have the same definitions as those in the formula (X-1) to the formula (X-4), respectively.

As the compound resulting from cleavage of one ether bond in the formula (X-1) to the formula (X-4), for example, a compound represented by the following formula (VI) that is a compound resulting from cleavage of one ether bond in the formula (III) is exemplified.

[Chem.23]

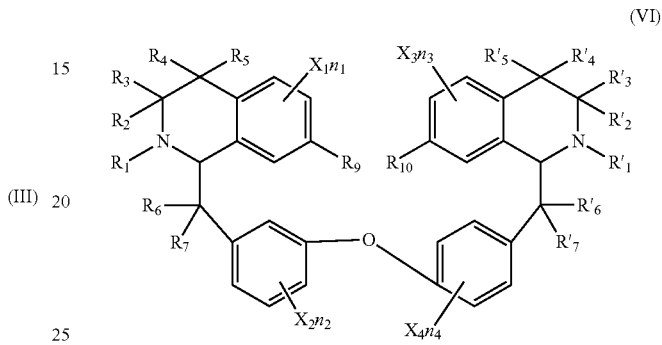

(VI)

$R_1$ to $R_7$, $R'_1$ to $R'_7$, $X_1$ to $X_4$, and $n_1$ to $n_4$ in the formula (VI) have the same definitions as those in the formula (X-1) and the formula (X-2), respectively, and $R_9$ and $R_{10}$ are each independently H, hydroxy, or straight-chain or branched-chain alkoxy having 1 to 10 carbon atoms.

In the bisbenzylisoquinoline alkaloid represented by the above formula (X-1) or formula (X-2) or the compound resulting from cleavage of one ether bond in the present invention, any stereoisomers, optical isomers, or mixtures thereof are included. For example, a compound having a stereoisomeric configuration in which C(1) and C(1') that are quaternary carbon atoms on an isoquinoline ring are each selected from RR, SS, 1S1'R, or 1R1'S is exemplified.

The bisbenzylisoquinoline alkaloid represented by the above formula (X-1) or (X-2) or the compound resulting from cleavage of one ether bond in the present invention may be a hydrate.

Further, as the pharmaceutically acceptable salt of the bisbenzylisoquinoline alkaloid represented by the above formula (X-1) or formula (X-2) or the compound resulting from cleavage of one ether bond in the present invention, an inorganic salt or an organic acid salt, or the like is exemplified. Examples of the inorganic salt include, but are not limited to, hydrochlorides, sulfates, nitrates, bicarbonates, carbonates, phosphates, hydrobromides, hydroiodides, and the like. Examples of the organic acid salt include, but are not limited to, tosylates, methanesulfonates, malates, acetates, citrates, malonates, tartrates, succinates, benzoates, ascorbates, α-ketoglutarates, α-glycerophosphates, and the like.

Specific examples of the bisbenzylisoquinoline alkaloid represented by the formula (I) and the pharmaceutically acceptable salt thereof include berbamine, (+)-berbamine, berbamine dihydrochloride, E6-berbamine (E6-norberbamine), fangchinoline, tetrandrine, isotetrandrine, cocsoline, and the like.

The structural formula of berbamine is shown below.
[Chem. 24]
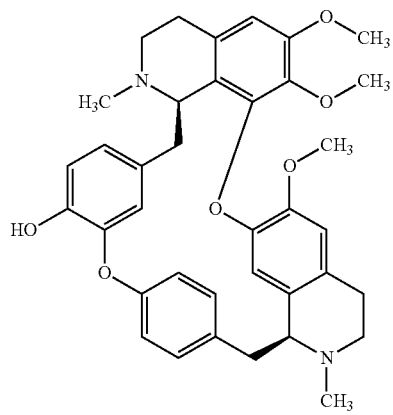
The structural formula of (+)-berbamine is shown below.
[Chem. 25]
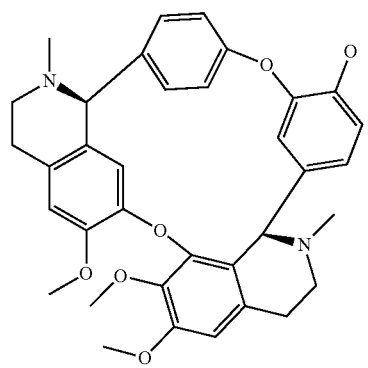
The structural formula of E6-berbamine is shown below.
[Chem. 26]
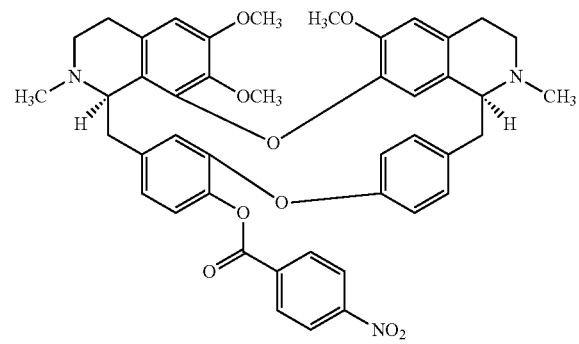
The structural formula of fangchinoline is shown below.
[Chem. 27]
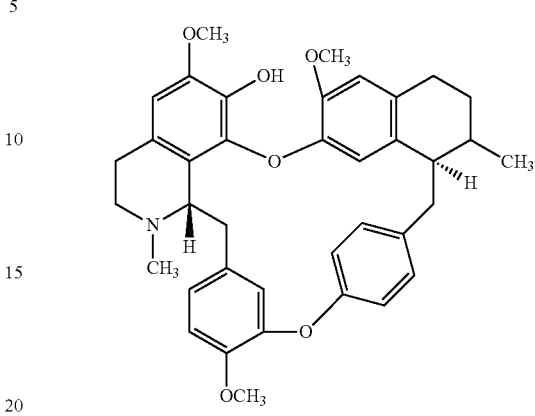
The structural formula of tetrandrine is shown below.
[Chem. 28]
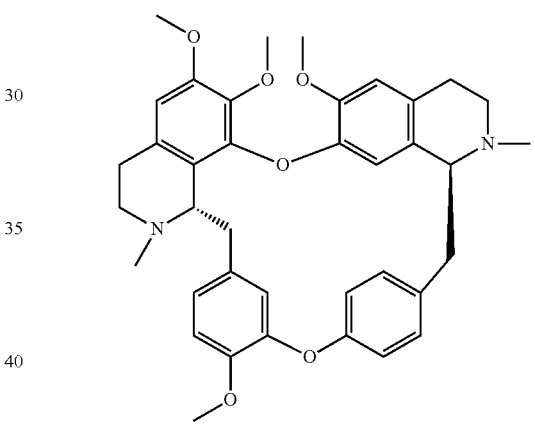
The structural formula of isotetrandrine is shown below.
[Chem. 29]
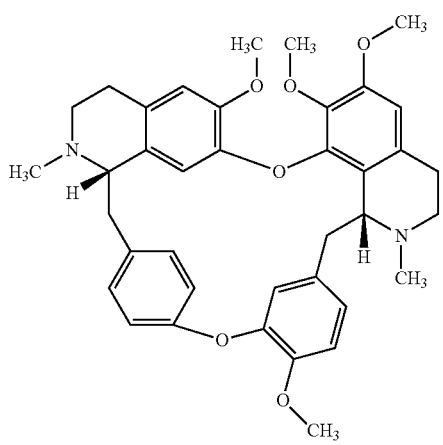

The structural formula of cocsoline is shown below.

[Chem. 30]

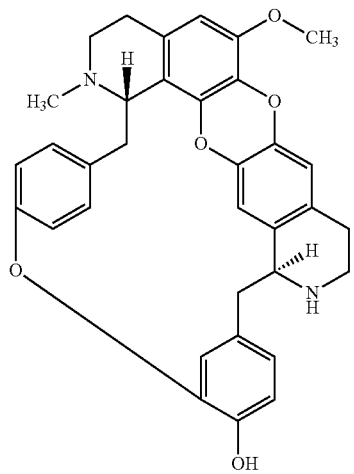

Further, specific examples of the bisbenzylisoquinoline alkaloid represented by the formula (I) include BBMD1 to BBMD13 that are berbamine derivatives represented by the following structural formulae, and the like.

The structural formula of BBMD1 is shown below.

[Chem. 31]

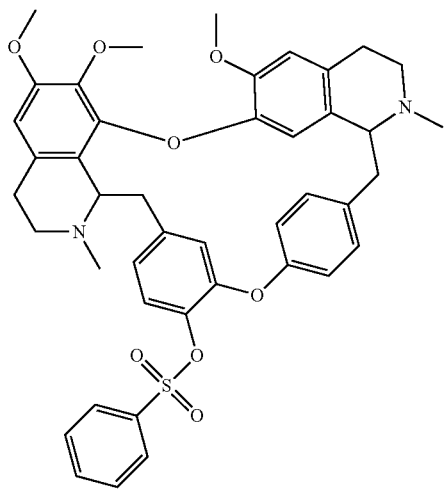

The structural formula of BBMD2 is shown below.

[Chem. 32]

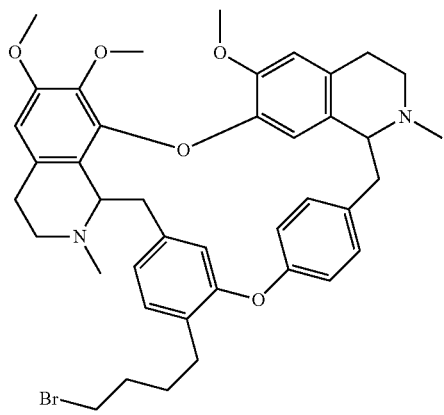

The structural formula of BBMD3 is shown below.

[Chem. 33]

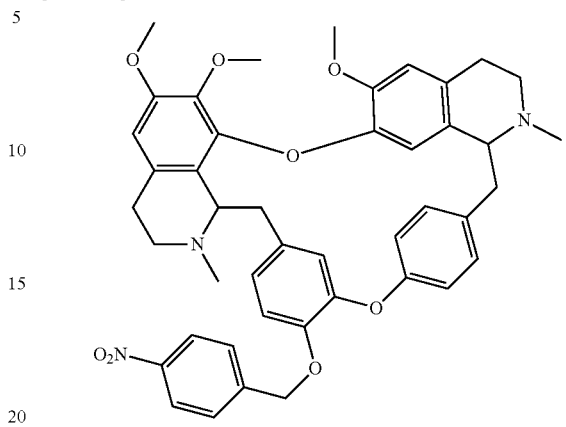

The structural formula of BBMD4 is shown below.

[Chem. 34]

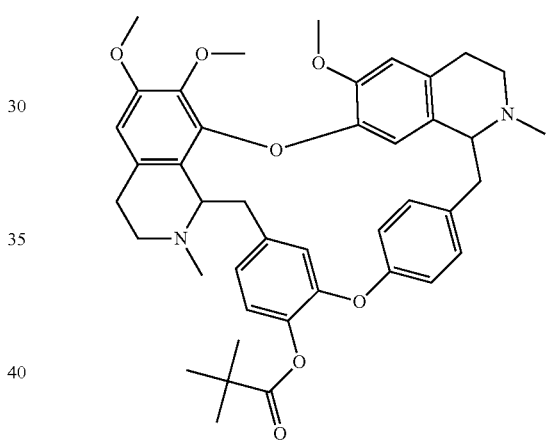

The structural formula of BBMD5 is shown below.

[Chem. 35]

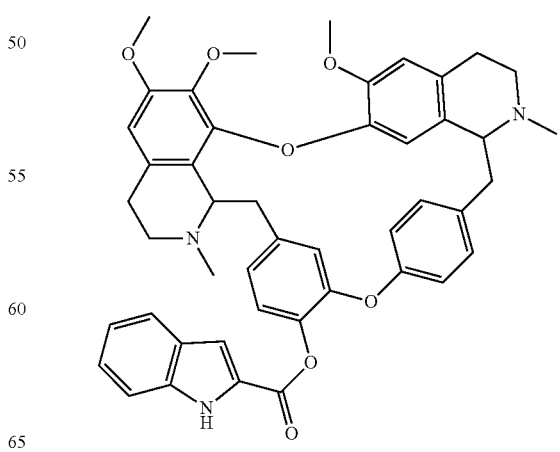

The structural formula of BBMD6 is shown below.
[Chem. 36]
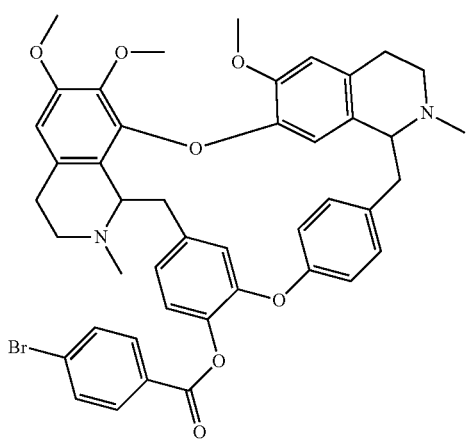
The structural formula of BBMD7 is shown below.
[Chem. 37]
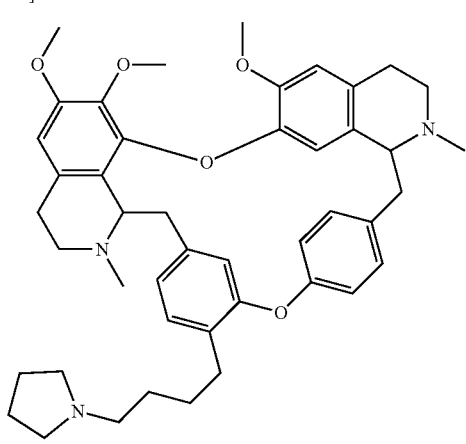
The structural formula of BBMD8 is shown below.
[Chem. 38]
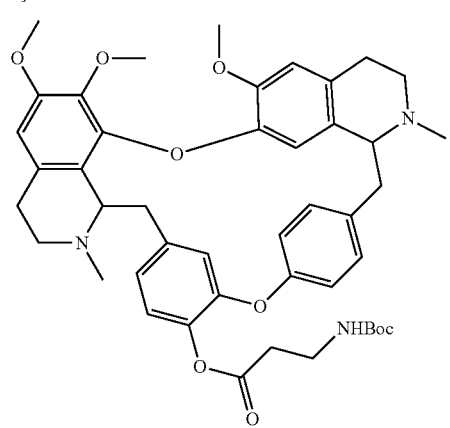
The structural formula of BBMD9 is shown below.
[Chem. 39]
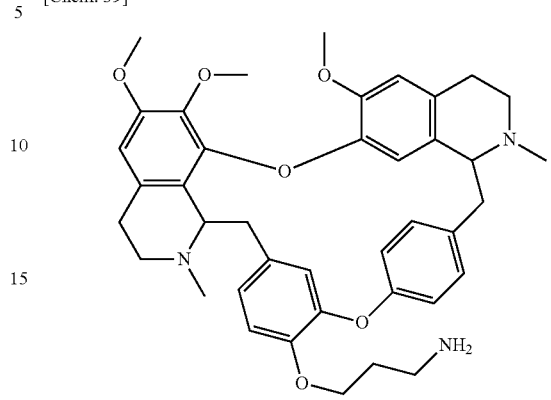
The structural formula of BBMD10 is shown below.
[Chem. 40]
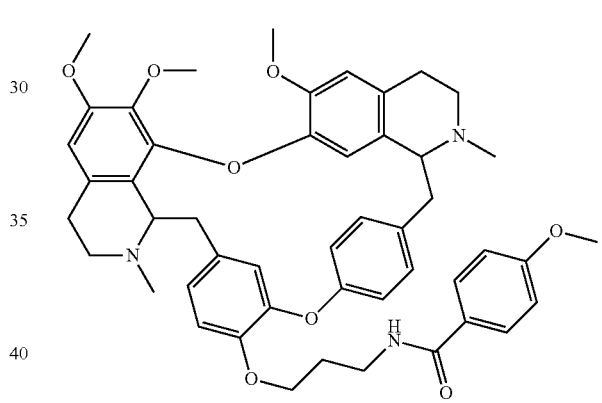
The structural formula of BBMD11 is shown below.
[Chem. 41]
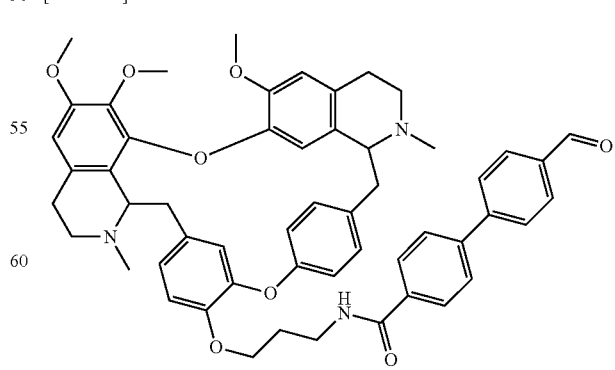

The structural formula of BBMD12 is shown below.

[Chem. 42]

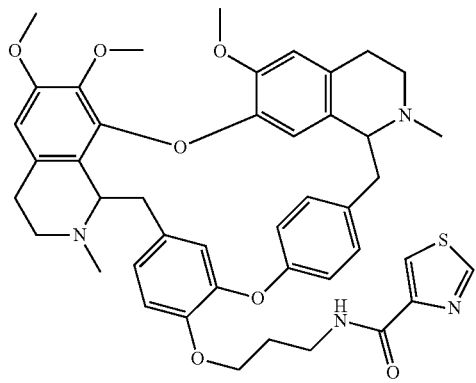

The structural formula of BBMD13 is shown below.

[Chem. 43]

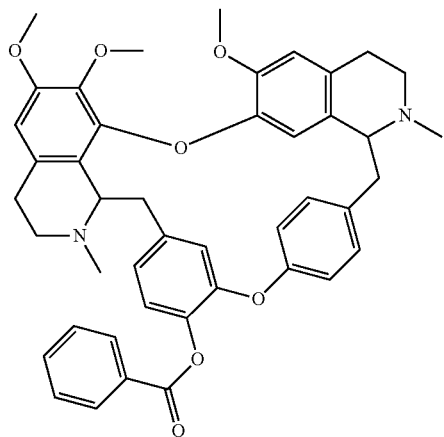

Specific examples of the bisbenzylisoquinoline alkaloid represented by the formula (II) include cepharanthine, oxyacanthine, thalrugosaminine, cocsoline, and the like.
The structural formula of cepharanthine is shown below.

[Chem. 44]

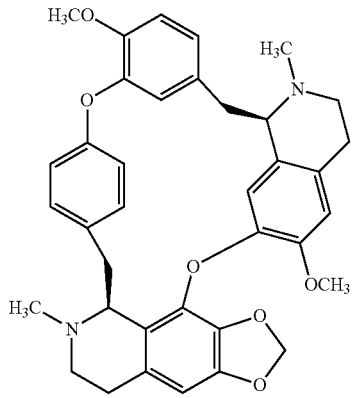

The structural formula of oxyacanthine is shown below.

[Chem. 45]

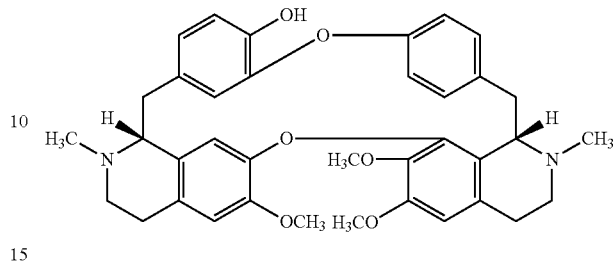

The structural formula of thalrugosaminine is shown below.

[Chem. 46]

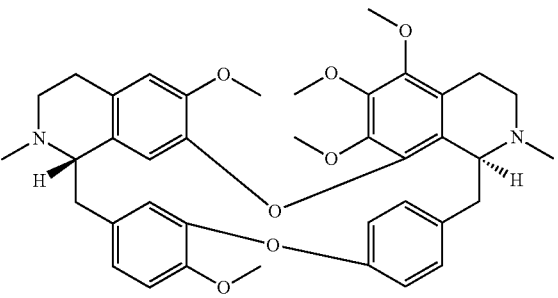

The structural formula of cocsoline is shown below.

[Chem. 47]

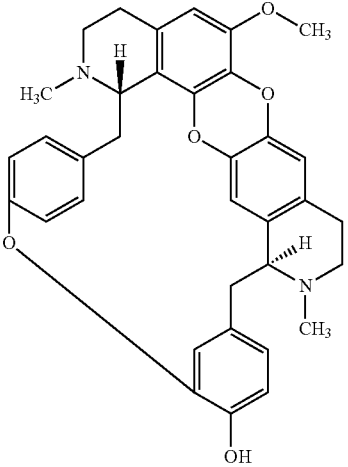

Specific examples of the bisbenzylisoquinoline alkaloid represented by the formula (III) include 2-norberbamine, and the like.

The structural formula of 2-norberbamine is shown below.

[Chem. 48]

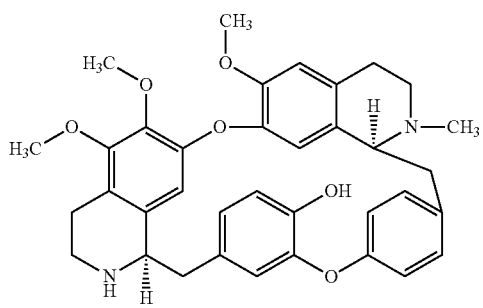

Specific examples of the bisbenzylisoquinoline alkaloid represented by the formula (IV) include cycleanine, and the like.

The structural formula of cycleanine is shown below.

[Chem. 49]

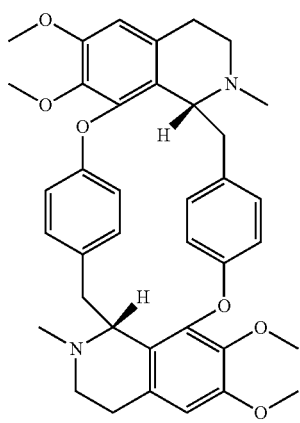

Specific examples of the bisbenzylisoquinoline alkaloid represented by the formula (V) include tubocurarine, tubocurarine chloride pentahydrate (curare pentahydrate), and the like. The structural formula of tubocurarine chloride pentahydrate is shown below.

[Chem. 50]

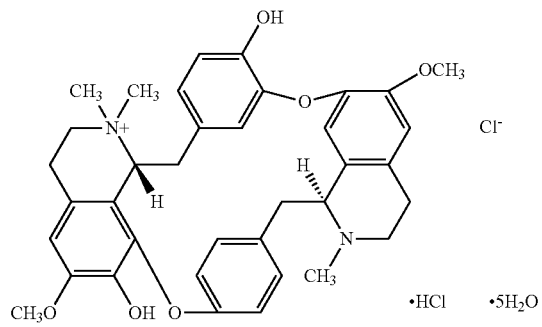

Specific examples of the compound represented by the formula (VI) include dauricin, magnoline, daurisoline, and the like.

The structural formula of dauricin is shown below.

[Chem. 51]

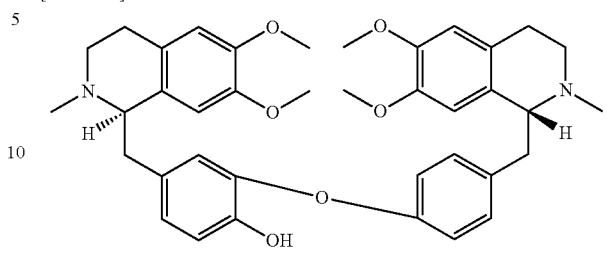

The structural formula of magnoline is shown below.

[Chem. 52]

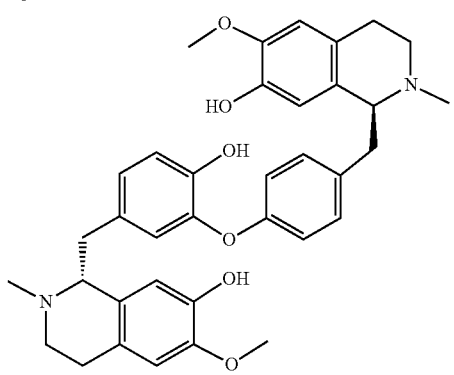

The structural formula of daurisoline is shown below.

[Chem. 53]

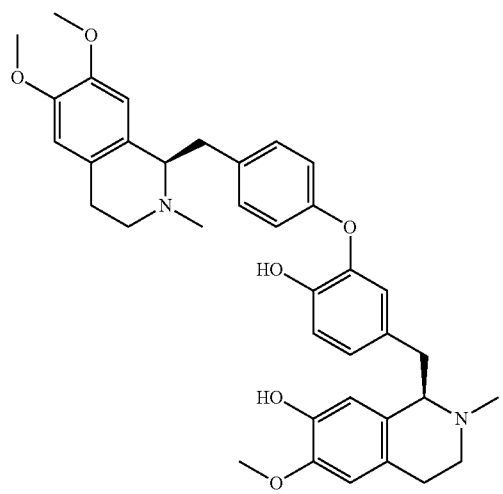

Further, the present invention also provides a method for producing T cells or NK cells including culturing T cells or NK cells in a culture medium containing a $Ca^{2+}$/calmodulin-dependent protein kinase II (CaMKII) inhibitor, a culture medium for culturing T cells or NK cells containing a CaMKII inhibitor, a method for maintaining the undifferentiated state of undifferentiated T cells including culturing T cells or NK cells in a culture medium containing a CaMKII inhibitor, and a growth promoter for T cells or NK cells containing a CaMKII inhibitor as an active ingredient.

CaMKII is a protein kinase to be activated by $Ca^{2+}$ and calmodulin that is a $Ca^{2+}$-binding protein.

Examples of the CaMKII inhibitor include, other than the bisbenzylisoquinoline alkaloid represented by the above formula (X-1) or formula (X-2) or the compound resulting from cleavage of one ether bond thereof or the pharmaceutically acceptable salt thereof, Peptide AIP (Autocamtide 2 Related Inhibitory Peptide) derived from a sequence at an autophosphorylation site present in a regulatory domain thereof, Staurosporine, Fasudil, Monohydrochloride Salt, 1-Naphthyl PP1, K-252a, KN-62, Lavendustin C, 12(S)-HPETE, K-252b, HA-1077 dihydrochloride, Arcyriaflavin A, and the like. The CaMKII inhibitor may be a compound alone or may be a composition or a mixture such as a plant extract. Further, the CaMKII inhibitor may be an artificially synthesized one or may be derived from a natural product.

Further, a method for inhibiting the CaMKII gene family such as siRNA targeting the CaMKII gene family is also included in the CaMKII inhibitor of the present invention. As the method for inhibiting the CaMKII gene family, the genomic DNA of stem cells, T cells, or NK cells may be altered by gene targeting, genome editing, or the like, and for example, the gene expression level may be permanently decreased by introducing shRNA or the like. As the gene targeting, for example, a method of introducing a targeting vector into a known pluripotent stem cell to cause homologous recombination, or the like is exemplified. The gene editing is not particularly limited, and examples thereof include known Zinc Finger Nuclease, Transcription Activator-like Effector Nuclease (TALEN), CRISPR/Cas9, and the like.

[T Cells]

The T cell in the present invention means a cell expressing an antigen receptor called T cell receptor (TCR) on its surface.

The T cells in the present invention are not particularly limited, but T cells expressing CD3 and also expressing at least one molecule of CD4 and CD8 are preferred.

Examples of such T cells include helper T cells, cytotoxic T cells, regulatory T cells, naive T cells, stem cell memory T cells (TSCM), central memory T cells (TCM), effector memory T cells, terminal effector T cells, and the like.

The helper T cells are CD4-positive cells and are further classified into Th1 cells, Th2 cells, Th17 cells, and the like according to the cytokine expressed by the cells (for example, J Allergy Clin. Immunol., 135(3): 626-635, 2012).

Examples of the Th1 cells include cells expressing IFN-γ, IL-2, TNF-α, or the like. Examples of the Th2 cells include cells expressing IL-4, IL-5, IL-6, IL-10, IL-13, or the like. Examples of the Th17 cells include cells expressing IL-17, IL-6, or the like.

The cytotoxic T cells are CD8-positive cells and are further classified into Tc1 cells, Tc2 cells, and the like according to the cytokine expressed by the cells in the same manner as the helper T cells.

Examples of the Tc1 cells include cells expressing IFN-γ, IL-2, TNF-α, or the like. Examples of the Tc2 cells include cells expressing IL-4, IL-5, IL-6, IL-10, IL-13, or the like.

Preferred examples of the regulatory T cells include CD4(+)CD25(+)FoxP3(+) cells.

Preferred examples of the naive T cells include CD4(+)CD45RA(+)CD62L(+)CCR7(+) cells, CD8(+)CD45RA(+)CD62L(+)CCR7(+) cells, CD4(+)CCR7(+)CD45RA(+)CD95(−)CD45RO(−) cells, CD8(+)CCR7(+)CD45RA(+)CD95(−)CD45RO(−) cells, and the like.

Preferred examples of the stem cell memory T cells include CD4(+)CD45RA(+)CD62L(+)CCR7(+)CD95(+) cells, CD8(+)CD45RA(+)CD62L(+)CCR7(+)CD95(+) cells, CD4(+)CCR7(+)CD45RA(+)CD95(+)CD45RO(+) cells, CD8(+)CCR7(+)CD45RA(+)CD95(+)CD45RO(+) cells, and the like.

Preferred examples of the central memory T cells include CD4(+)CD45RA(−)CD62L(+)CCR7(+)CD95(+) cells, CD8(+)CD45RA(−)CD62L(+)CCR7(+)CD95(+) cells, CD4(+)CCR7(+)CD45RA(−)CD45RO(+) cells, CD8(+)CCR7(+)CD45RA(−)CD45RO(+) cells, and the like.

Preferred examples of the effector memory T cells include CD4(+)CCR7(−)CD45RA(−)CD45RO(+) cells, CD8(+)CCR7(−)CD45RA(−)CD45RO(+) cells, and the like.

Preferred examples of the terminal effector T cells include CD4(+)CD45RA(+)CD62L(−) cells, CD8(+)CD45RA(+)CD62L(−) cells, and the like.

The T cells in the present invention are preferably undifferentiated T cells. Examples of the undifferentiated T cells include naive T cells, stem cell memory T cells, and central memory T cells in descending order of the degree of undifferentiation. Among these, naive T cells and stem cell memory T cells are particularly preferred from the viewpoint of maintaining the undifferentiated state of the cells and improving the proliferative property or the in vivo persistence.

Since T cells having a high undifferentiated property exhibit a high therapeutic effect, the T cells in the present invention are preferably T cells for immune cell therapy.

As a method for determining whether or not T cells maintain an undifferentiated state, a method for performing the determination by detecting the expression of an undifferentiated marker and/or not detecting the expression of a differentiated marker, a method for performing the determination by detecting the expression of other various types of markers (genes or proteins), a method for observing the morphological characteristics of cells, or the like is exemplified. For example, CCR7 is used as an undifferentiated marker of peripheral blood (for example, Nature Reviews Immunology, 18: 363-373, 2018).

The T cells in the present invention are preferably T cells derived from pluripotent stem cells.

A method for inducing T cells from pluripotent stem cells can be carried out using a known method. Specifically, for example, the method described in WO 2016/076415 as a method for producing CD8-positive cells and the method described in WO 2017/221975 as a method for producing CD4 and CD8 double-positive T cells are exemplified.

In the present invention, the pluripotent stem cells are stem cells having pluripotency capable of differentiating into many cells present in vivo and also having a proliferative ability, and include any cells induced into at least hematopoietic progenitor cells to be used in the present invention.

The pluripotent stem cells are preferably of mammalian origin, and more preferably of human origin.

The pluripotent stem cells are not particularly limited, but examples thereof include embryonic stem (ES) cells, cloned embryo-derived embryonic stem (ntES) cells obtained by nuclear transfer, germline stem cells (GS cells), embryonic germ cells (EG cells), induced pluripotent stem (iPS) cells, cultured fibroblasts or umbilical cord blood-derived pluripotent stem cells or bone marrow stem cell-derived pluripotent stem cells (Muse cells), and the like. In the present invention, preferred pluripotent stem cells are iPS cells, and more preferably human iPS cells from the viewpoint that they can be obtained without destroying embryos, eggs, or the like in the production process.

A method for producing iPS cells is known in the art, and can be produced by introducing a reprogramming factor into any somatic cells. Examples of the reprogramming factor include genes or gene products such as Oct3/4, Sox2, Sox1, Sox3, Sox15, Sox17, Klf4, Klf2, c-Myc, N-Myc, L-Myc, Nanog, Lin28, Fbx15, ERas, ECAT15-2, Tcl1, beta-catenin, Lin28b, Sal11, Sal14, Esrrb, Nr5a2, Tbx3, and Glis1. These reprogramming factors may be used alone or in combination.

Examples of the combination of reprogramming factors include combinations described in WO 2007/069666, WO 2008/118820, WO 2009/007852, WO 2009/032194, WO 2009/058413, WO 2009/057831, WO 2009/075119, WO 2009/079007, WO 2009/091659, WO 2009/101084, WO 2009/101407, WO 2009/102983, WO 2009/114949, WO 2009/117439, WO 2009/126250, WO 2009/126251, WO 2009/126655, WO 2009/157593, WO 2010/009015, WO 2010/033906, WO 2010/033920, WO 2010/042800, WO 2010/050626, WO 2010/056831, WO 2010/068955, WO 2010/098419, WO 2010/102267, WO 2010/111409, WO 2010/111422, WO 2010/115050, WO 2010/124290, WO 2010/147395, WO 2010/147612, Huangfu D, et al., Nat. Biotechnol., 26: 795-797, 2008, Shi Y, et al., Cell Stem Cell, 2: 525-528, 2008, Eminli S, et al., Stem Cells. 26: 2467-2474, 2008, Huangfu D, et al., Nat. Biotechnol. 26: 1269-1275, 2008, Shi Y, et al., Cell Stem Cell, 3, 568-574, 2008, Zhao Y, et al., Cell Stem Cell, 3: 475-479, 2008, Marson A, Cell Stem Cell, 3, 132-135, 2008, Feng B, et al., Nat. Cell Biol. 11: 197-203, 2009, R. L. Judson et al., Nat. Biotechnol., 27: 459-461, 2009, Lyssiotis C A, et al., Proc Natl Acad Sci USA. 106: 8912-8917, 2009, Kim J B, et al., Nature. 461: 649-643, 2009, Ichida J K, et al., Cell Stem Cell. 5: 491-503, 2009, Heng J C, et al., Cell Stem Cell. 6: 167-74, 2010, Han J, et al., Nature. 463: 1096-100, 2010, Mali P, et al., Stem Cells. 28: 713-720, 2010, Maekawa M, et al., Nature. 474: 225-9, 2011, and the like.

The somatic cells to be used for producing iPS cells are not particularly limited, and examples thereof include fetal (pup) somatic cells, neonatal (pup) somatic cells, mature healthy or diseased somatic cells, primary cultured cells, subcultured cells, established cells, and the like.

Examples of the somatic cells include (1) tissue stem cells (for example, somatic stem cells) such as neural stem cells, hematopoietic stem cells, mesenchymal stem cells, or dental pulp stem cells, (2) tissue progenitor cells such as hematopoietic progenitor cells, or (3) differentiated cells such as blood cells (for example, peripheral blood cells, umbilical cord blood cells, and the like), myeloid cells, lymphocytes, epithelial cells, endothelial cells, muscle cells, fibroblasts (for example, skin cells, and the like), hair cells, hepatocytes, gastric mucosal cells, intestinal cells, spleen cells, pancreatic cells (for example, exocrine pancreatic cells, and the like), brain cells, lung cells, kidney cells, or adipocytes, and the like. The somatic cells are preferably T cells, but somatic cells other than T cells (non-T cells) may be used.

As the somatic cells, for example, lymphocytes (preferably T cells) that have undergone TCR gene rearrangement are preferred. When lymphocytes are used as the somatic cells, it is preferred that the lymphocytes are stimulated and activated by an anti-CD3 antibody and an anti-CD28 antibody in the presence of a cytokine such as IL-2 prior to a reprogramming step.

The stimulation can be performed, for example, by adding a cytokine such as IL-2, an anti-CD3 antibody, or an anti-CD28 antibody to the culture medium and culturing the lymphocytes for a given period of time. Further, the anti-CD3 antibody and the anti-CD28 antibody may be those to which a magnetic bead or the like is attached, or the stimulation may be given by culturing the T cells for a given period of time on a culture dish io which the anti-CD3 antibody and the anti-CD28 antibody are attached to the surface thereof instead of adding these antibodies to the culture medium. Further, the stimulation may be given by adding an antigen peptide that is recognized by human T cells to the culture medium.

In the present invention, a mammalian individual from which somatic cells are collected is not particularly limited, but is preferably a human. When the T cells to be produced are used for blood transfusion, the somatic cells to serve as the origin of iPS cells are preferably isolated from a subject to be transfused from the viewpoint that the type of human leukocyte antigen (HLA) is easily matched with that of a patient to be transfused.

As the iPS cells, an existing cell line may be used. For example, as a human iPS cell line, 253G1 cell line (RIKEN Cell Bank No. HPS0002), 201B7 cell line (RIKEN Cell Bank No. HPS0063), 409B2 cell line (RIKEN Cell Bank No. HPS0076), 454E2 cell line (RIKEN Cell Bank No. HPS0077), HiPS-RIKEN-1A cell line (RIKEN Cell Bank No. HPS0003), HiPS-RIKEN-2A cell line (RIKEN Cell Bank No. HPS0009), HiPS-RIKEN-12A cell line (RIKEN Cell Bank No. HPS0029), Nips-B2 cell line (RIKEN Cell Bank No. HPS0223), or the like is exemplified.

The iPS cells may be iPS cells into which CAR or specific TCR has been introduced in advance.

Here, the CAR means a fusion protein containing an extracellular domain that binds to an antigen and an intracellular domain derived from a polypeptide different from the extracellular domain. As the CAR, for example, a fusion protein in which an antigen recognition domain (L chain and H chain of a variable region) of an antibody against a specific antigen is bound to, for example, an intracellular domain of a T cell receptor such as CD3 and an intracellular domain of a costimulatory molecule such as CD28 or 4-1BB, or the like is exemplified (for example, JP-T-2015-509716).

The antigen recognition domain of the CAR can be selected according to the target antigen, and thereby it is possible to produce T cells specific to the target antigen. For example, when CD19 is used as an antigen, the antigen recognition domain of an anti-CD19 antibody is cloned and bound to the intracellular domain of a CD3 molecule, whereby the CAR can be formed (for example, Cancer Res., 66: 10995-11004, 2006). In addition, by selecting the type and number of costimulatory molecules to be bound, the intensity or duration of activation can be controlled (for example, Mol Ther., 17: 1453-1464, 2009).

By introducing the CAR, it becomes possible to impart specificity for a target antigen to any T cells whose differentiation has been induced from T cell-derived iPS cells or non-T cell-derived iPS cells. Further, by introducing the CAR, an antigen molecule can be directly recognized, and a high immunoreaction can be caused even in a tumor in which the expression of HLA class I gene has decreased.

Further, by introducing the specific TCR, it becomes possible to impart specificity for a target cell to any T cells whose differentiation has been induced from T cell-derived iPS cells or non-T cell-derived iPS cells. Further, a high immunoreaction can be caused even in a tumor which expresses a peptide-HLA complex in a cancer specific manner.

The T cells in the present invention are not particularly limited, but may be peripheral blood-derived T cells. Further, the T cells into which CAR or TCR described above is introduced may be T cells in peripheral blood. The peripheral blood is derived from a patient oneself or a healthy subject such as a related donor or an unrelated donor.

Further, the T cells in the present invention may be primary hematopoietic stem and progenitor cell-derived T cells. The primary hematopoietic stem and progenitor cells can be collected from umbilical cord blood, bone marrow, mobilized peripheral blood, or the like, and these are derived from a patient oneself or a healthy subject such as a related donor or an unrelated donor. A method for inducing T cells from primary hematopoietic stem and progenitor cells can be carried out by a method which is the same as or similar to the method for inducing T cells from pluripotent stem cells described above (for example, Induction of T-cell development from human cord blood hematopoietic stem cells by Delta-like 1 in vitro; Blood, 105(4): 1431-1439, 2005).

The T cells in the present invention preferably have desired antigen specificity. Therefore, it is preferred that lymphocytes to serve as the origin of the iPS cells described above have desired antigen specificity.

The lymphocytes may be specifically isolated by purification using an affinity column or the like on which a desired antigen is immobilized. In this purification, a method for purifying the lymphocytes having desired antigen specificity from a human tissue using a material (so-called MHC tetramer) obtained by tetramerizing a major histocompatibility complex (MHC) to which a desired antigen is bound can also be adopted.

Further, T cells can also be obtained through concentration by stimulation with a CD3 antibody or CD3 beads to achieve selective proliferation without particularly performing purification.

[NK Cells]

As the NK cells in the present invention, any NK cells can be used. It is preferred that a donor of the NK cells and a recipient of the NK cells are of the same species. For example, when the donor is a human, the recipient is a human. It is more preferred that a donor of the NK cells and a recipient of the NK cells are the same individual. For example, when the donor is donor X, the recipient is the donor X.

The NK cells in the present invention can be obtained by a known method (for example, the method described in Japanese Patent No. 5016732). The NK cells can be obtained by induction from mononuclear cells collected from peripheral blood, a lymph node, a thymus, bone marrow, a tumor, pleural effusion, ascites, or umbilical cord blood, more preferably peripheral blood mononuclear cells. For example, mononuclear cells including NK cells can be collected from peripheral blood by a specific gravity centrifugation method.

The NK cells in the present invention are preferably pluripotent stem cell-derived NK cells. The pluripotent stem cells are preferably of mammalian origin, and more preferably of human origin. A method for inducing NK cells from pluripotent stem cells can be carried out using a known method (for example, the method described in Cell Stem Cell. 23(2): 181-192, 2018). The pluripotent stem cells are the same as those described above.

The NK cells in the present invention may be primary hematopoietic stem and progenitor cell-derived NK cells. The primary hematopoietic stem and progenitor cells are the same as those described above.

The NK cells in the present invention may be peripheral blood-derived NK cells. The peripheral blood is derived from a patient oneself or a healthy subject such as a related donor or an unrelated donor. Further, the NK cells exhibit a high therapeutic effect, and therefore, the NK cells in the present invention are preferably NK cells for immune cell therapy.

Examples of the NK cells include CD3(−)CD56(+) cells. Further, as the NK cells, cells expressing a surface marker such as CD2(+/−), CD5(−), CD7(+), CD8(+), CD1d(−), CD16a(+), CD27(+), CD49a to f(+)CD56(+), CD57(+), CD94(+), CD161(+) or CD165(+) in addition to CD3(−) CD56(+) is exemplified.

The NK cells in the present invention may be either immature NK cells or mature NK cells, and examples thereof include CD56 bright CD16(−) immature NK cells, CD56 dim CD16(+) mature NK cells, and the like.

[Culture Medium for Culturing T Cells or NK Cells]

The culture medium for culturing T cells or NK cells according to the present invention contains a bisbenzylisoquinoline alkaloid represented by the formula (X-1) or the formula (X-2), a compound resulting from cleavage of one ether bond thereof or a pharmaceutically acceptable salt thereof.

The culture medium for culturing T cells or NK cells according to the present invention can be prepared by using a culture medium to be used for culturing animal cells as a base culture medium and adding the bisbenzylisoquinoline alkaloid represented by the formula (X-1) or the formula (X-2), the compound resulting from cleavage of one ether bond thereof or the pharmaceutically acceptable salt thereof thereto.

The content of the bisbenzylisoquinoline alkaloid represented by the formula (X-1) or the formula (X-2), the compound resulting from cleavage of one ether bond thereof or the pharmaceutically acceptable salt thereof in the culture medium for culturing T cells or NK cells according to the present invention is not particularly limited as long as it exhibits a proliferation promoting activity for T cells or NK cells, but is, for example, generally from 0.1 nM to 10 μM, and as a preferred range, a range from 0.1 nM to 3 μM, from 0.1 nM to 10 nM, from 1 nM to 3 μM, from 1 nM to 10 nM, from 10 nM to 100 nM, from 100 nM to 1 μM, from 1 nM to 1 μM, or the like is exemplified. When the bisbenzylisoquinoline alkaloid represented by the formula (X-1) or the formula (X-2) and the pharmaceutically acceptable salt thereof are at least one selected from berbamine, (+)-berbamine, berbamine dihydrochloride, E6-berbamine, and cepharanthine, the content is preferably from 0.1 nM to 10 μM.

Examples of the base culture medium include Iscove's Modified Dulbecco's Medium (IMDM) medium, Medium 199 medium, Eagle's Minimal Essential Medium (EMEM) medium, αMEM medium, Dulbecco's Modified Eagle's Medium (DMEM) medium, Ham's F12 medium, RPMI 1640 medium, Fischer's medium, Neurobasal Medium (Life Technologies), a mixed medium thereof, and the like. In the culture medium, serum may be contained, or a serum-free medium may be used.

The base culture medium may contain, for example, one or more substances of albumin, insulin, transferrin, selenium, a fatty acid, a trace element, 2-mercaptoethanol, thiolglycerol, a lipid, an amino acid, L-glutamine, a nonessential amino acid, a vitamin, a growth factor, a low-molecular weight compound, an antibiotic, an antioxidant, pyruvic acid, a buffer, an inorganic salt, a cytokine, and the like as needed.

The culture medium for culturing T cells or NK cells according to the present invention preferably further contains vitamin C group, or a cytokine.

The vitamin C group means L-ascorbic acid and its derivatives, and an L-ascorbic acid derivative means a substance that becomes vitamin C by an enzymatic reaction in vivo. Examples of the L-ascorbic acid derivative include vitamin C phosphate, ascorbyl glucoside, ethyl ascorbyl, vitamin C esters, ascorbyl tetrahexyldecanoate, ascorbyl stearate, ascorbyl-2-phosphate-6-palmitate, and the like. It is preferably vitamin C phosphate, and for example, L-ascorbyl phosphate such as sodium L-ascorbyl phosphate or magnesium L-ascorbyl phosphate is exemplified. The concentration of the vitamin C group in the culture medium for culturing T cells or NK cells is, for example, from 5 µg/mL to 500 µg/mL.

Examples of the cytokine include IL-2, IL-7, IL-12, IL-15, IL-18, IL-21, Flt3L, and the like. The concentration thereof in the culture medium for culturing T cells or NK cells is, for example, from 1 ng/mL to 100 ng/mL for IL-7, from 1 ng/mL to 100 ng/mL for IL-12, from 1 ng/mL to 100 ng/mL for IL-15, from 1 ng/mL to 100 ng/mL for IL-18, from 1 ng/mL to 100 ng/mL for IL-21, and from 1 ng/mL to 100 ng/mL for Flt3L.

The culture medium for culturing T cells or NK cells according to the present invention contains the bisbenzylisoquinoline alkaloid represented by the formula (X-1) or the formula (X-2), the compound resulting from cleavage of one ether bond thereof or the pharmaceutically acceptable salt thereof so as to be able to promote cell proliferation while maintaining the state (for example, undifferentiated property) of the cells, and therefore, feeder cells need not be included. By not including feeder cells in the culture medium, the risk of infection derived from feeder cells can be reduced, and further, the production stability is improved, and as a result, the cost can be reduced.

The culture medium for culturing T cells or NK cells according to the present invention may contain a MAPK cascade inhibitor in addition to the bisbenzylisoquinoline alkaloid represented by the formula (X-1) or the formula (X-2) or the compound resulting from cleavage of one ether bond thereof or the pharmaceutically acceptable salt thereof. By the combined use of the MAPK cascade inhibitor, the proliferation of cells (for example, memory T cells) having an excellent activity in immune cell therapy can be enhanced.

The MAPK cascade is composed of three types of kinase (protein kinase) molecules: MAPKKK, MAPKK, and MAPK, or the like, and at least three types of MAPK cascades (ERK cascade, p38 cascade, and JNK cascade) having different functions are present in human cells (for example, Journal of Electrophoresis, vol. 60, pp. 7-10, 2015). Among these, the ERK pathway is activated by a growth factor or the like and mainly acts on cell proliferation, whereas the p38 cascade and the JNK cascade that are stress-responsive MAPK cascades are activated by various environmental stress stimuli and inflammatory cytokines, and play an important role in inducing apoptosis and controlling immune response.

Preferred examples of the MAPK cascade inhibitor in the present invention include an ERK cascade inhibitor or a p38 cascade inhibitor. Examples of the ERK cascade inhibitor include inhibitors targeting BRAF, RAF, and the like which constitute the ERK cascade (for example, CEP-32496, ZM-336372, etc.) and the like. Examples of the p38 cascade inhibitor include inhibitors targeting p38 (for example, SB-203580, Losmapimod, etc.) and the like.

[Culturing of T Cells or NK Cells]

A culture container to be used for culturing T cells or NK cells is not particularly limited, and examples thereof include flasks, dishes, plates, microwell plates, microslides, chamber slides, tubes, trays, culture bags, and the like. A base material of such a culture container is not particularly limited, and examples thereof include glass, various types of plastics such as polypropylene and polystyrene, and the like.

The culture container may be cell-adhesive or non-cell-adhesive, and is appropriately selected according to the intended use. The cell-adhesive culture container may be coated with any cell-supporting matrix such as an extracellular matrix (ECM) for the purpose of improving the adhesiveness between the surface of the culture container and cells.

Examples of the cell-supporting matrix include collagen, gelatin, poly-L-lysine, poly-D-lysine, laminin or a partial structure of laminin, fibronectin or a mixture thereof, and the like, and specifically, Matrigel, a lysed cell membrane preparation, or the like is exemplified (for example, Lancet, 365, 9471, 1636-1641, 2005).

The T cells or the NK cells used for culturing may be dispersed cells or non-dispersed cells. The dispersed cells refer to cells treated for promoting cell dispersion. Examples of the dispersed cells include cells that form a small cell cluster composed of 2 to 50 cells, 2 to 20 cells, or 2 to 10 cells. The dispersed cells may be floating (suspended) cells or adherent cells.

The culture density of T cells or NK cells is not particularly limited as long as an effect of promoting the survival and proliferation of the cells can be achieved. The culture density is preferably from $1.0\times10^1$ to $1.0\times10^7$ cells/mL, more preferably from $1.0\times10^2$ to $1.0\times10^7$ cells/mL, further more preferably from $1.0\times10^3$ to $1.0\times10^7$ cells/mL, and most preferably from $3.0\times10^4$ to $1.0\times10^7$ cells/mL.

The culture conditions such as a temperature, a $CO_2$ concentration, a dissolved oxygen concentration, and a pH can be appropriately set based on a conventionally known technique. For example, the culture temperature is, although not particularly limited, generally from 30 to 40° C., and preferably 37° C. The $CO_2$ concentration is generally from 1 to 10%, and preferably from 2 to 5%. The oxygen partial pressure is generally from 1 to 10%. The pH is generally from 3 to 10.

In the culturing of T cells or NK cells, the cells may be cultured in the presence of feeder cells, but are preferably cultured without using feeder cells. The temperature conditions when culturing T cells or NK cells are not particularly limited, but are, for example, generally from 37 to 42° C., and preferably from 37 to 39° C. Further, the culturing period can be appropriately determined by those skilled in the art while monitoring the number of T cells or NK cells. The number of days is not particularly limited, but is, for example, at least 1 day or more, 2 days or more, 3 days or more, 4 days or more, 5 days or more, 10 days or more, 30 days or more, 40 days or more, 50 days or more, 60 days or more, or 70 days or more, preferably 3 days or more, more preferably 10 days or more, further more preferably 30 days or more, particularly preferably 40 days or more, and most preferably 50 days or more. According to the culturing method of the present invention, long-term culturing for 50 days or more can be carried out.

The method for producing T cells or NK cells according to the present invention includes a step of subculturing T cells or NK cells as needed. The subculturing of T cells and the induction of differentiation thereof can be carried out by a conventionally known method.

A cell composition containing T cells or NK cells obtained by the method for producing T cells or NK cells according to the present invention can be used for a cell source for regenerative medicine or the like. The cell composition may be a composition containing dispersed T cells or NK cells such as small cell clusters.

The above-mentioned cell composition can be used, for example, for preservation, transportation, and subculturing of T cells or NK cells by cryopreservation. The cell composition may further contain serum or a substitute therefor, or an organic solvent such as DMSO. In that case, the concentration of the serum or the substitute therefor is not particularly limited, but is, for example, from 1 to 50% (v/v), and preferably from 5 to 20% (v/v). The concentration of the organic solvent is not particularly limited, but is, for example, from 0 to 50% (v/v), and preferably from 5 to 20% (v/v). The cell composition may contain feeder cells, but preferably does not contain feeder cells.

[Immune Cell Therapy]

T cells or NK cells obtained by the production method of the present invention, or a cell composition thereof can be suitably used in an immune cell therapeutic agent. The T cells, the NK cells, or the cell composition thereof are/is produced as an oral/parenteral preparation, preferably a parenteral preparation such as an injection, a suspension, or an infusion by being mixed with a pharmaceutically acceptable carrier according to a known method. As the pharmaceutically acceptable carrier that can be contained in the parenteral preparation, for example, an aqueous solution for injection such as an isotonic solution containing physiological saline, glucose, or another adjuvant (for example, D-sorbitol, D-mannitol, sodium chloride, or the like) can be exemplified.

The immune cell therapeutic agent may be blended with, for example, a buffer (for example, a phosphate buffer solution, a sodium acetate buffer solution, or the like), a soothing agent (for example, benzalkonium chloride, procaine hydrochloride, or the like), a stabilizer (for example, human serum albumin, polyethylene glycol, or the like), a preservative, an antioxidant, or the like.

When the immune cell therapeutic agent is formulated as an aqueous suspension, T cells or NK cells may be suspended in the above-mentioned buffer solution at, for example, about $1.0 \times 10^6$ to about $1.0 \times 10^7$ cells/mL.

The pharmaceutical preparation thus obtained is stable and has low toxicity, and therefore can be safely administered to a mammal such as a human. The administration method is not particularly limited, and it can be administered orally or parenterally, but it is preferably administered through injection or infusion, and examples of the administration route include intravenous administration, subcutaneous administration, intradermal administration, intramuscular administration, intraperitoneal administration, direct administration to the affected area, and the like. The dose of the immune cell therapeutic agent varies depending on the administration subject, target organ, symptoms or administration method, etc., but generally in an adult patient (assuming the body weight is 60 kg), for example, in the case of parenteral administration, as the cell number per dose, about $1.0 \times 10^7$ to about $1.0 \times 10^9$ cells are administered about 4 to about 8 times at an interval of about 1 to 2 weeks.

In order to promote the in vivo activation of T cells or NK cells to be administered, in the immune cell therapeutic agent of the present invention, the T cells or the NK cells serving as the active ingredient thereof and a receptor ligand for the T cells or the NK cells may be combined.

[Method for Maintaining Undifferentiated State]

The method for maintaining the undifferentiated state of undifferentiated T cells according to the present invention is characterized by culturing T cells in the above-mentioned culture medium for culturing T cells. The method for culturing T cells is the same as described above. By culturing undifferentiated T cells in the culture medium, by the effect of the bisbenzylisoquinoline alkaloid represented by the formula (X-1) or the formula (X-2) or the compound resulting from cleavage of one ether bond thereof or the pharmaceutically acceptable salt thereof, the undifferentiated state of the undifferentiated T cells can be maintained.

The maintenance of the undifferentiated state of T cells can be evaluated, for example, based on whether or not the expression level of an undifferentiated marker gene of T cells is significantly maintained at a level equal to the expression level at the start of culturing at an mRNA level or a protein level in the T cells cultured in the presence of the bisbenzylisoquinoline alkaloid represented by the formula (X-1) or the formula (X-2) or the compound resulting from cleavage of one ether bond thereof or the pharmaceutically acceptable salt thereof as compared with T cells cultured in the absence of the bisbenzylisoquinoline alkaloid represented by the formula (X-1) or the formula (X-2) or the compound resulting from cleavage of one ether bond thereof or the pharmaceutically acceptable salt thereof. Examples of the undifferentiated marker gene of T cells include CCR7 gene and the like.

As a method for measuring the expression level of an undifferentiated marker gene, in the case of measuring an mRNA level, for example, a method such as RT-PCR, quantitative PCR, or Northern blotting using a primer or a probe specific to the marker gene is exemplified. Further, in the case of measuring a protein level, for example, an immunological method such as ELISA, flow cytometry, or Western blotting using an antibody specific to a protein encoded by the marker gene is exemplified.

As a result of measuring the expression level of the undifferentiated marker gene, it can be determined that the undifferentiated state of T cells could be maintained when the relative ratio of the expression level of the undifferentiated marker gene in T cells at the time of start of culturing to the expression level of the undifferentiated marker gene in T cells after culturing for a predetermined period of time in the presence of the bisbenzylisoquinoline alkaloid represented by the formula (X-1) or the formula (X-2) or the compound resulting from cleavage of one ether bond thereof or the pharmaceutically acceptable salt thereof is larger than the relative ratio (control) when culturing in the absence of the bisbenzylisoquinoline alkaloid represented by the formula (X-1) or the formula (X-2) or the compound resulting from cleavage of one ether bond thereof or the pharmaceutically acceptable salt thereof.

[Growth Promoter for T Cells or NK Cells]

The growth promoter for T cells or NK cells according to the present invention (hereinafter, also abbreviated as the growth promoter according to the present invention) is characterized by containing a bisbenzylisoquinoline alkaloid represented by the formula (X-1) or the formula (X-2) or a compound resulting from cleavage of one ether bond thereof or a pharmaceutically acceptable salt thereof. By culturing T cells or NK cells using a culture medium containing the growth promoter according to the present invention, the proliferation efficiency of T cells or NK cells is significantly improved even when feeder cells are not used, and the state of the cells (for example, undifferentiated property) can be maintained.

The growth promoter according to the present invention can also be provided as a composition further containing a physiologically acceptable carrier [for example, a physiological isotonic solution [an isotonic solution containing physiological saline, the above-mentioned base culture medium, glucose, or another adjuvant (for example, D-sorbitol, D-mannitol, sodium chloride, or the like), or the like], an excipient, an antiseptic agent, a stabilizer (for example, human serum albumin, polyethylene glycol, or the like), a binder, a solubilizing agent, a nonionic surfactant, a buffer (for example, a phosphate buffer solution, a sodium acetate buffer solution, or the like), a preservative, an antioxidant, the above-mentioned additives, or the like], a signal transduction inhibitor, or the like.

The content of the bisbenzylisoquinoline alkaloid represented by the formula (X-1) or the formula (X-2), the compound resulting from cleavage of one ether bond thereof or the pharmaceutically acceptable salt thereof in the growth promoter according to the present invention is preferably configured such that, for example, when the growth promoter according to the present invention is added to a culture medium, the growth promoter is contained so that the concentration of the compound in the culture medium is sufficient for promoting the proliferation of T cells or NK cells.

It is preferred that the growth promoter according to the present invention is used by a method such as adding it in a state of an isotonic aqueous solution, a powder, or the like to a culture medium.

The growth promotion of T cells or NK cells can be evaluated, for example, based on whether or not the cell number of T cells or NK cells cultured in the presence of the growth promoter according to the present invention has significantly increased as compared with that of T cells or NK cells cultured in the absence of the growth promoter according to the present invention. The measurement of the cell number can be carried out, for example, using a commercially available cell number measuring kit by a known MTT method, WST method, or the like. It can be determined that the proliferation of T cells or NK cells can be promoted when, as a result of measurement, the relative ratio of the cell number of T cells or NK cells at the time of start of culturing to the cell number of T cells or NK cells after culturing for a predetermined period of time in the presence of the growth promoter according to the present invention is larger than the relative ratio (control) when culturing in the absence of the growth promoter according to the present invention.

Hereinafter, the present invention will be specifically described with reference to Examples, however, the present invention is not limited to these Examples.

EXAMPLES

Example 1

Induction of Differentiation of iPS Cells

The induction of T cells from iPS cells was carried out by a method modified from the method described in NPL 1. A schematic view of the procedure for inducing the differentiation of iPS cells in Example 1 is shown in FIG. 1.

iPS cells were maintained using mouse embryonic fibroblasts (MEF) as feeder cells. As the culture medium, a culture medium for iPS cells [Dulbecco's Modified Eagle's Medium/Nutrient Mixture F-12 Ham (Sigma), Knockout Serum Replacement (KSR, 20%, Life Technologies), 1× Insulin, Transferrin, Selenium Solution (ITS-G, 100×, Thermo Fisher Scientific), 1% MEM Non-Essential Amino Acids Solution (NEAA, Life Technologies), 0.1 mM 2-Mercaptoethanol (55 mM, Gibco), Fibroblast Growth Factor basic (Sigma)] was used.

Hematopoietic progenitor cells (HPCs) were induced by culturing iPS cells on 10T1/2 cells to form Sac (NPL 2). The 10T1/2 cells were maintained in a 0.1% gelatin-coated dish using Basal Medium Eagle (Life Technologies) supplemented with 1% FBS and 1% L-Glutamine-Penicillin-Streptomycin solution (PSG, Sigma) and used as the feeder cells.

The iPS cells were treated with a dissociation agent [D-PBS supplemented with $CaCl_2$ (Nacalai Tesque), KSR (Life Technologies), and trypsin (Life Technologies)], and iPS cell colonies were collected. The colonies were seeded on the 10T1/2 cells, and cultured using Sac medium [IMDM (Sigma), 15% FBS, 1% PSG, Insulin, Transferrin, Selenium Solution (ITS-G, 1×, GIbco), monothioglycerol (MTG, Nacalai Tesque), L(+)-ascorbic acid (PAA, 50 µg/mL, Nacalai Tesque, 03420-52), VEGF (R&D Systems, 20 ng/mL)] at 37° C. under 5% $O_2$ and 5% $CO_2$ (Day 0). The Sac medium was replaced on Day 4. The culture medium was replaced with Sac medium supplemented with SCF (R&D Systems, 30 ng/mL) and Flt3 (Peprotech, 10 ng/mL) on Days 7, 10, and 12, and the cells were cultured at 37° C. under 20% $O_2$ and 5% $CO_2$.

T cells were induced by co-culturing HPCs with OP9-DL1 cells. The OP9-DL1 cells were maintained in alpha-MEM medium (Life technologies) supplemented with 15% FBS and 1% PSG Sac on day 14 after the initiation of differentiation induction was collected with the tip of a pipette, and after pipetting, it was allowed to pass through a cell strainer to collect the flow-through.

The obtained blood cells were seeded on OP9-DL1 cells, and cultured using alpha-MEM medium (Life technologies) supplemented with IL-7 (1 ng/mL), Flt3L (10 ng/mL), PAA (50 µg/mL), ITS-G, 15% FBS, and 1% PSG.

After 3 days, the blood cells were transferred to fresh OP9-DL1 cells. Thereafter, the culture medium was replaced every 3 days and the cells were transferred to fresh OP9-DL1 cells every 6 days. After 24 days from the start of co-culturing with the OP9-DL1 cells, the culture medium was replaced with alpha-MEM medium supplemented with IL-7 (10 ng/mL), Flt3L (10 ng/mL), PAA (50 µg/mL), ITS-G, 15% FBS, PSG, and an anti-CD3 antibody OKT3 (1 µg/mL).

After 3 days, a trypsin treatment and removal of the OP9-DL1 cells by adhesion selection were performed, and then, the cells were transferred to a 24-well plate coated with RetroNectin (registered trademark) (TaKaRa, diluted to 2 µg/mL with PBS) and cultured in alpha-MEM medium supplemented with IL-7 (10 ng/mL), Flt3L (10 ng/mL), IL-21 (10 ng/mL), PAA (50 µg/mL), ITS-G, 15% FBS, and PSG After 6 days from OKT3 stimulation, the cells were stained with CD8beta-PE (Beckman), CD5-PECy7 (Thermo Fisher), CD1a-FITC (Thermo Fisher) and CD336-APC (BioLegend), and CD8beta(+)CD5(+)CD1a(−)CD336(−) cells were sorted, whereby CD8(+) T cells (T-iPS-T cells) were obtained.

Example 2

Expansion Culture of iPS-T Cells

Figure 2:
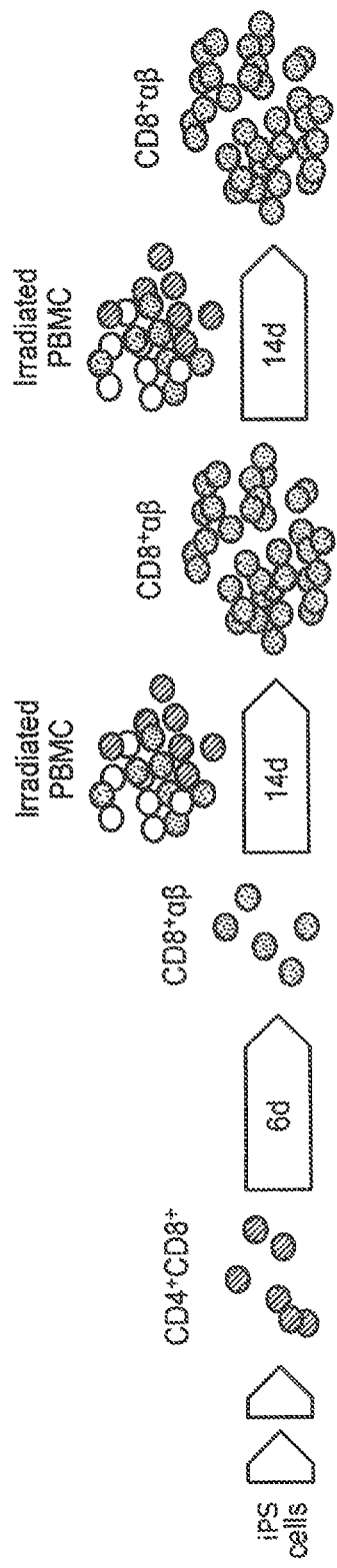
FIG. 2 shows a schematic view of a procedure for proliferating iPS-T cells.

The number of CD8(+) T cells (T-iPS-T cells) obtained according to the method of Example 1 is only several thousands to several tens of thousands. The cells were co-cultured with Phytohemagglutinin-P (PHA) and PBMCs derived from a healthy donor, and the number of cells was increased several tens of thousands of times. A schematic view of the procedure for expanding iPS-T cells in Example 2 is shown in FIG. 2.

PBMCs were thawed and cultured overnight in alpha-MEM medium supplemented with 15% FBS and PSG On the following day, the PBMCs were irradiated with a radiation (40 Gy), and thereafter mixed with iPS-T cells in alpha-MEM medium supplemented with IL-7 (5 ng/mL), IL-15 (5 ng/mL), Pan Caspase Inhibitor Z-VAD-FMK (R&D Systems, 10 µM), PAA (50 µg/mL), ITS-G, 15% FBS, and PSG, and PHA (Wako, 2 µg/mL) was added thereto (Day 0). The culture medium was replaced every 3 days, and the cells were appropriately subcultured in accordance with the proliferation, and cultured until Day 14. In this Example, this step was performed once or twice as needed.

Example 3

Immunophenotyping Test

The expression of T cell-related molecules in the iPS-T cells was analyzed by flow cytometry. In the analysis, cells obtained by expanding CD8ab(+) iPS-T cells with PHA and PBMCs 0 to 2 times were used. For staining, CD8β-PE (BECKMAN), CD5-PECy7 (Thermo Fisher), CD27-APC, CD28-BV421, CCR7-APC, CD45RA-BV510, CD45RO-APCCy7 and CD62L-FITC, CD95-PECy7 (all are from BioLegend) were used. In the analysis, a BD LSR-FORTESSA cytometer (BD Bioscience) was used, and dead cells were excluded using propidium iodide (PI).

Figure 3A:
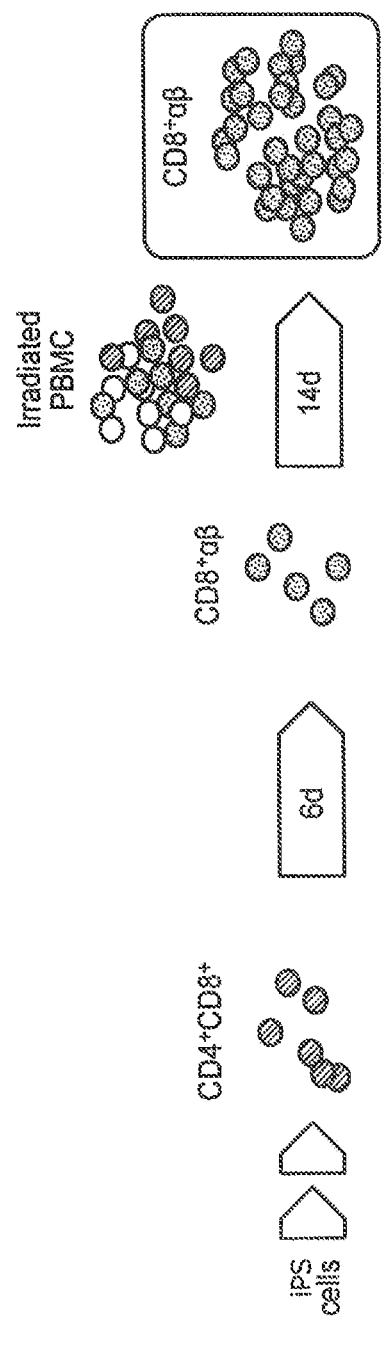
FIG. 3A shows a schematic view of a procedure for an immunophenotyping test using T-iPS-T cells.
Figure 3B:
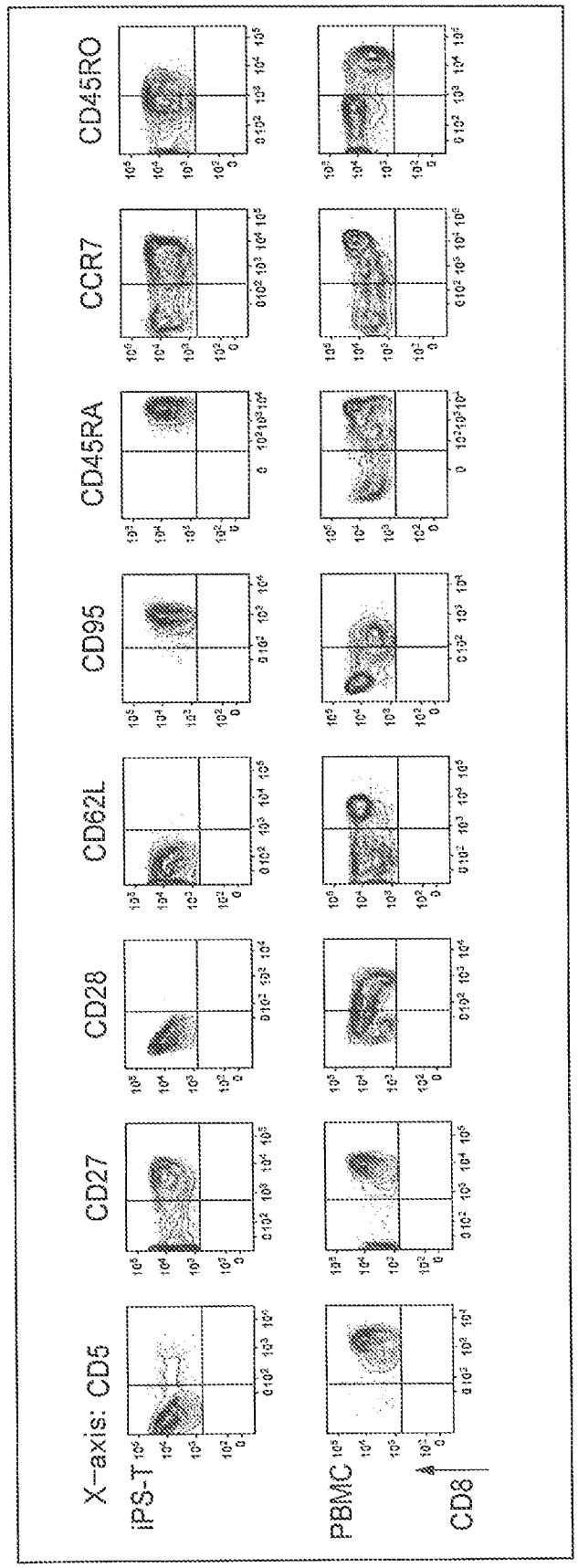
FIG. 3B shows the results of the immunophenotyping test using T-iPS-T cells.

A schematic view of the procedure for performing an immunophenotyping test using T-iPS-T cells expanded once is shown in FIG. 3A, and the results are shown in FIG. 3. As shown in FIG. 3B, the positive rates of CD95 and CD45RA were 100%. In addition, partial expression of CD5, CD27, CCR7, and CD45RO was observed. The expression of CD28 and CD62L in T cells in PBMCs derived from a healthy subject serving as the positive control was observed, but expression in T-iPS-T cells was not observed.

Subsequently, in order to evaluate a change in the expression of a marker molecule during a differentiation process accompanying the proliferation of T cells, T-iPS-T cells for which the number of expansion times in Example 2 is different were compared and examined. A schematic view of the procedure for the examination is shown in FIG. 4(A), and the results are shown in FIG. 4(B). As shown in FIG. 4(B), a decrease in the expression level of CCR7 and the CCR7-positive cell ratio due to expansion was observed.

A hierarchy in which CD45RA(+)CCR7(+) Naive T cells are positioned at the top for undifferentiated property among T cells in PBMCs is known (for example, Nicholas P. Restifo, Blood, 124: 476-477, 2014). Therefore, it was suggested that CD45RA(+)CCR7(+) is an undifferentiated cell marker in iPS-T cells.

Example 4

Figure 5:
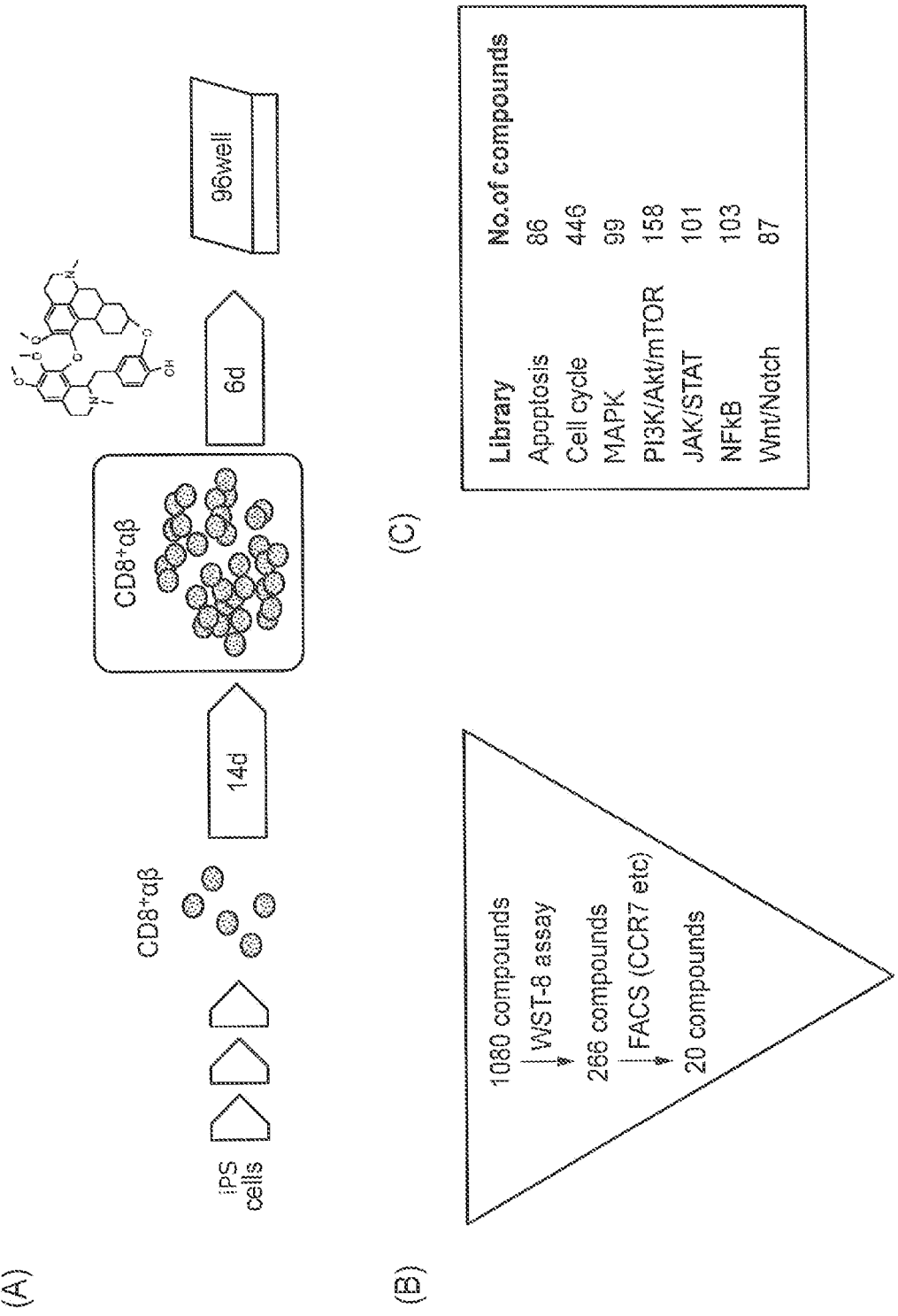
FIG. 5(A) to 5(C) show a scheme of screening for a low-molecular weight compound that improves the proliferation efficiency of T-iPS-T cells under feeder-free culture conditions.

Screening for Low-Molecular Weight Compound Using Number of Viable Cells as Index T-iPS-T cells were cultured without using PBMC feeder to screen for a low-molecular weight compound that improves the proliferation efficiency. A scheme for the screening is shown in FIGS. 5(A) to 5(C).

T-iPS-T cells (1,500 cells/well) after 1st expansion were seeded and cultured in RPMI-1640 medium (SIGMA, R8758) supplemented with 15% FBS (CORNING, 35-076-CV, 35076104R), 1% PSG (SIGMA, G1146), PAA (50 µg/mL, Nacalai Tesque, 03420-52), ITS-G, IL-7 (5 ng/mL), IL-12 (50 ng/mL), IL-15 (5 ng/mL), IL-18 (50 ng/mL), IL-21 (20 ng/mL), and z-VAD-fmk (10 µM). The cells were stimulated by adding CD3/CD28 Dynabeads (Gibco, 11131D, the "Dynabeads" is a registered trademark) (4,500 beads/well) thereto, and 1,080 compounds [MedChemExpress, Apoptosis Compound Library (HY-L003), Cell Cycle/DNA Damage Compound Library (HY-L004), JAK/STAT Compound Library (HY-L008), MAPK Compound Library (HY-L010), NF-kappaB Compound Library (HY-L014), PI3K/Akt/mTOR Compound Library (HY-L015), and Wnt/Hedgehog/Notch Compound Library (HY-L020)] were added thereto (one type per well) at a final concentration of 1 µM, and then, the cells were cultured at 37° C. under 5% $CO_2$.

DMSO (0.1%) that is a solvent for the compound was used as a control. After 6 days, the number of viable cells was measured using Cell Count Reagent SF (Nacalai Tesque, 07553) and a microplate reader (SoftMax Pro 5.X, Molecular Devices, 450 nm/650 nm). As a result, 266 compounds that exhibit an absorbance equal to or higher than that of DMSO were selected.

A calibration curve for cell number was set as follows. When measuring the number of viable cells, 12-point serial dilution was performed for the same cells as those used in the screening, and the cells were seeded (0 to 1,536,000 cells/well) in RPMI-1640 medium supplemented with 15% FBS, 1% PSG, PAA, ITS-G, IL-7 (5 ng/mL) and IL-15 (5 ng/mL). The number of viable cells was measured together with the screening samples, and a calibration curve for WST-8 assay was formed.

Figure 6:
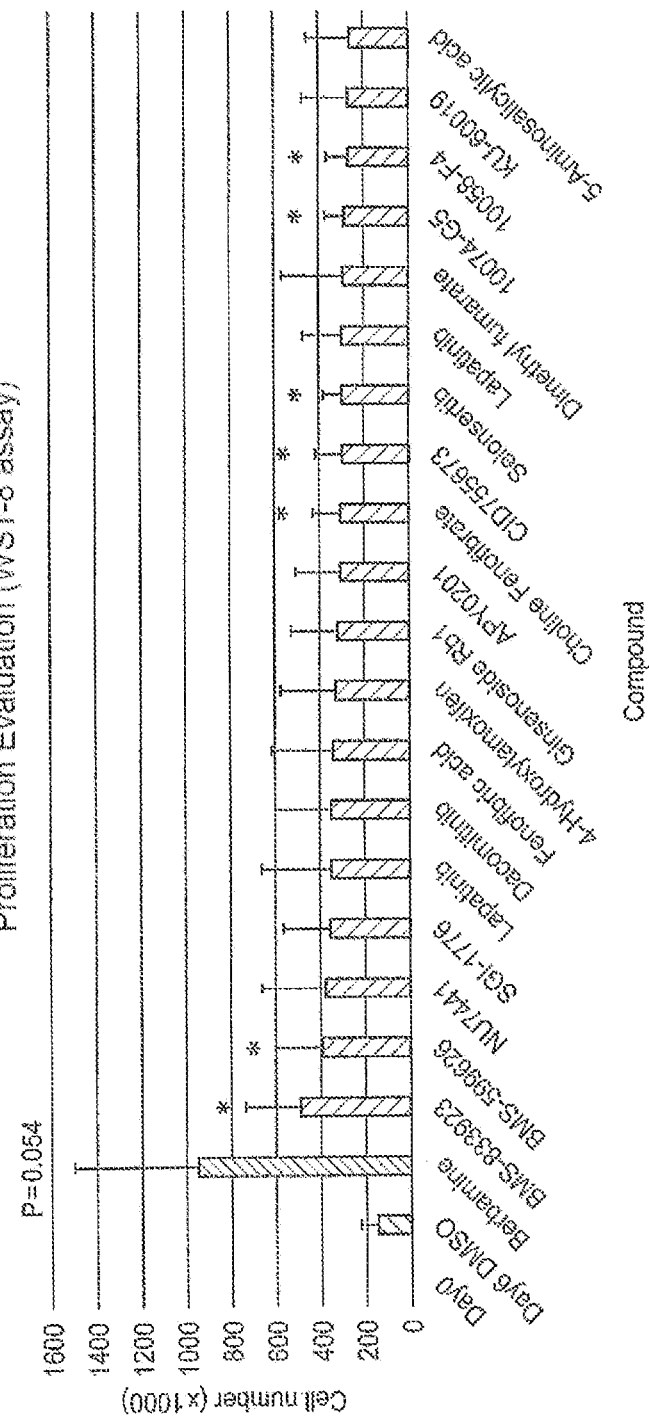
FIG. 6 shows the results of screening for a low-molecular weight compound that promotes the proliferation of T-iPS-T cells under feeder-free culture conditions using the number of viable cells as an index.

The results of the control (DMSO) and the top 20 compounds with respect to the number of viable cells are shown in FIG. 6. As shown in FIG. 6, among the 1,080 compounds used in this Example, the highest number of viable cells was observed when the cells were cultured in the presence of berbamine (HY-N0714A, MedChemExpress). From the results, it was indicated that the bisbenzylisoquinoline alkaloid represented by the formula (X-1) or the formula (X-2) has an effect of remarkably promoting cell proliferation under feeder-free culture conditions.

Example 5

Screening for Low-Molecular Weight Compound Using Number of CCR7-Positive Cells as Index T-iPS-T cells, and the 266 compounds extracted from the 1,080 compounds used in Example 4 were used, and the cells were cultured for 6 days according to the culturing method in Example 4, and the expression of CCR7 and CD45RA was analyzed by FACS. The cells cultured with the compound were transferred to a 96-well plate, and washed with a staining solution (PBS containing 2% FBS), and then stained with CCR7-APC (BioLegend, 353214) and CD45RA-BV510 (BioLegend, 304142).

After washing, the cells were resuspended in the staining solution containing PI. Half the amount was analyzed using a BD LSR Fortessa cytometer (BD Bioscience) equipped with HTS, and all cells were recorded. A graph in which the control (DMSO) and the top 20 compounds were plotted with respect to the number of events (#Cells) of CD45RA (+)CCR7(+) cells in the PI-negative cell population analyzed by FlowJo 10 is shown in FIG. 7.

Figure 7:
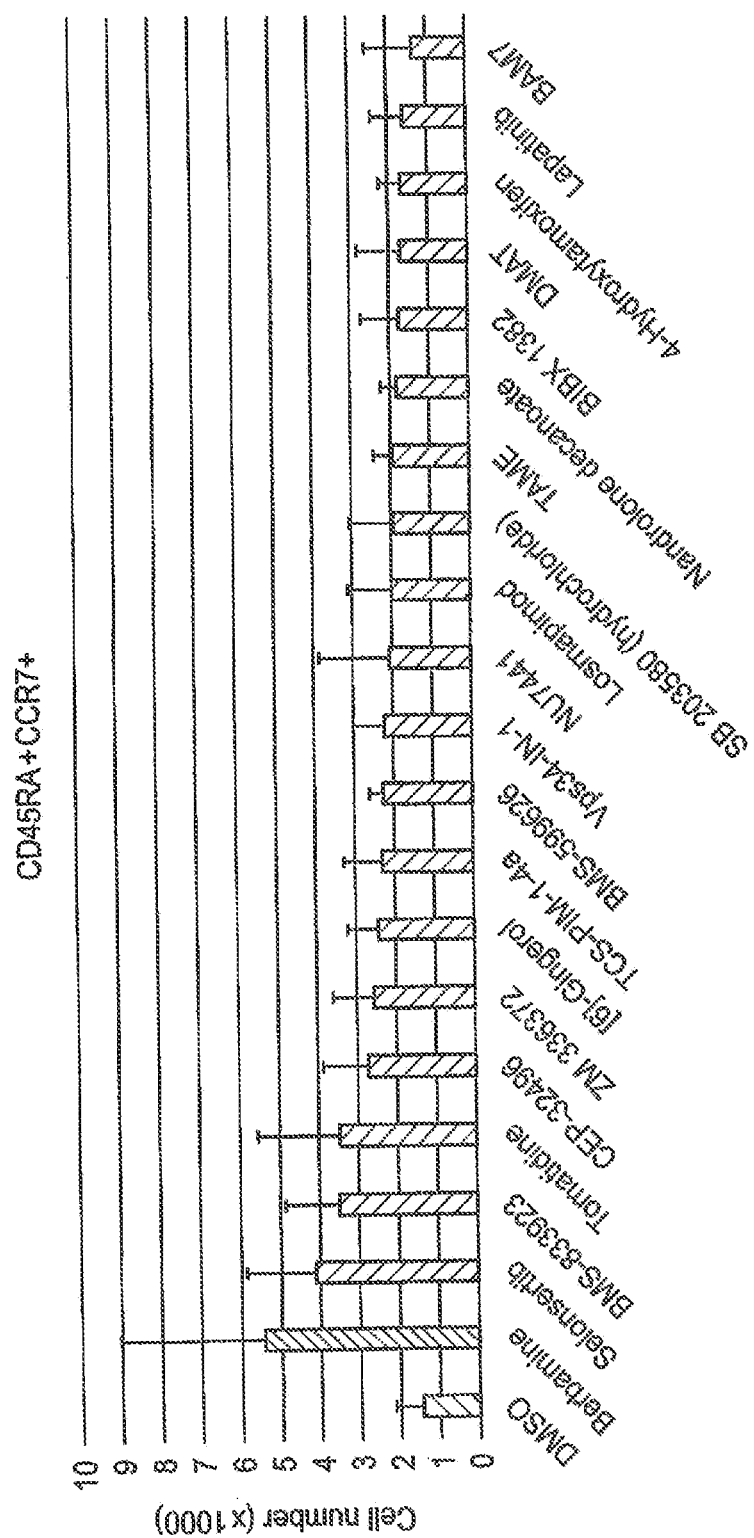
FIG. 7 shows the results of screening for a low-molecular weight compound that promotes cell proliferation while maintaining the undifferentiated property of undifferentiated T cells under feeder-free culture conditions.

As shown in FIG. 7, among the 266 compounds used in this Example, berbamine showed the highest number of CD45RA(+)CCR7(+) cells. From the above results, the bisbenzylisoquinoline alkaloid of the formula (I) was extracted as a compound that promotes cell proliferation while maintaining the undifferentiated property of undifferentiated T cells under feeder-free culture conditions.

Example 6

Evaluation of Concentration Dependence of Bisbenzylisoquinoline Alkaloid

The concentration dependence of the bisbenzylisoquinoline alkaloid represented by the formula (X-1) or the formula (X-2) in feeder-free proliferation of T-iPS-T cells was examined. T-iPS-T cells were cultured using alpha-MEM medium supplemented with 15% FBS, 1% PSG, PAA (50 µg/mL), ITS-G, IL-7 (5 ng/mL), IL-12 (50 ng/mL), IL-15 (5 ng/mL), IL-18 (50 ng/mL), IL-21 (20 ng/mL), and z-VAD-fmk (10 µM). In addition, to the culture medium, each of various types of bisbenzylisoquinoline alkaloids represented by the formula (I) or the formula (II) [berbamine (SIGMA, 547190), (+)-berbamine (Ark Pharm, AK167975), E6-berbamine (Santa Cruz, SC-221573), or cepharanthine (Cayman, 19648)] was added at a concentration of 1 nM, 3 nM, 10 nM, 30 nM, 100 nM, 300 nM, 1 µM, 3 µM, or 10 µM. After culturing for 6 days, staining and measurement were performed in the same manner as in Example 5. The results are shown in FIGS. 8 and 9.

Figure 8:
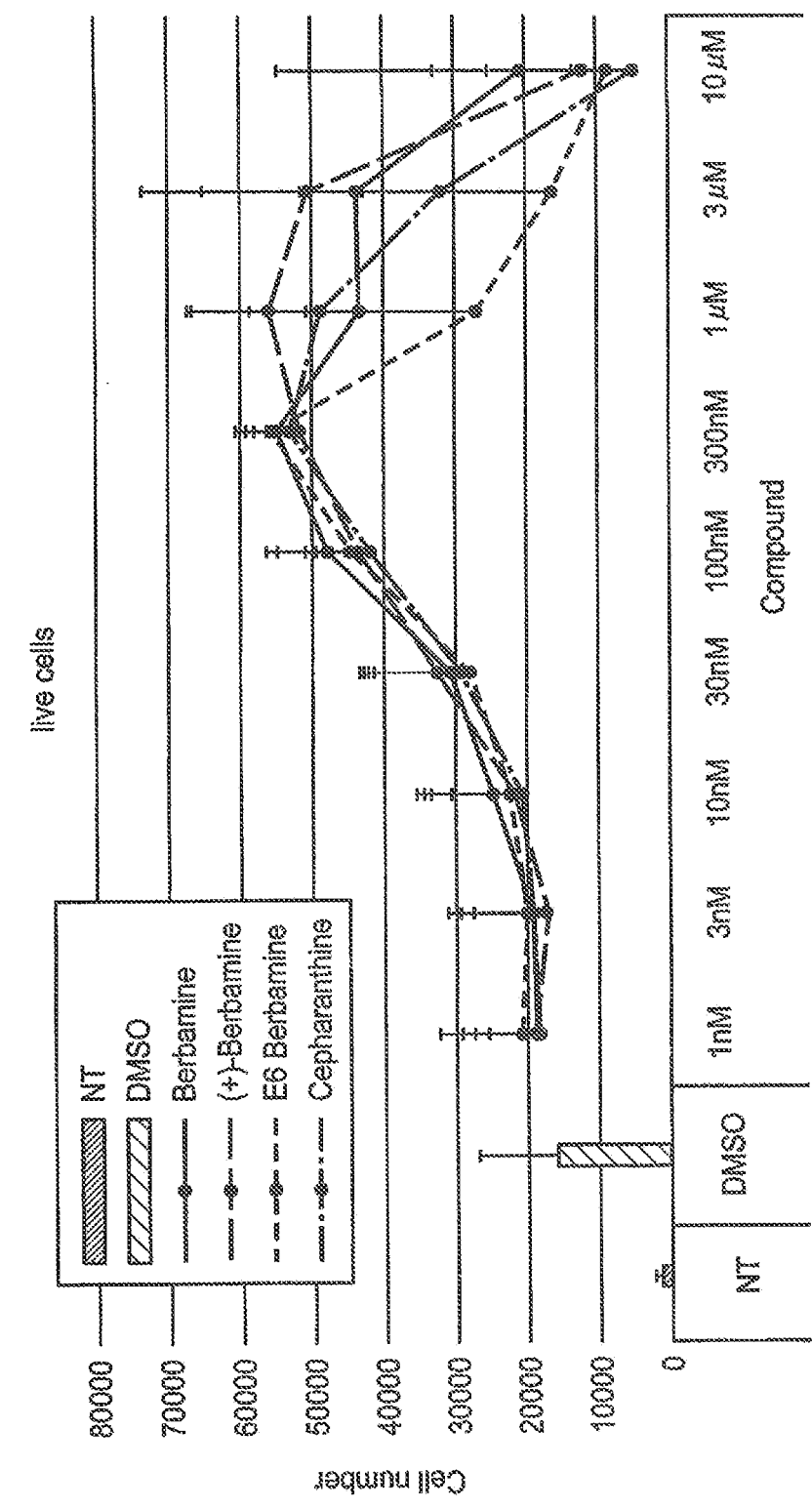
FIG. 8 shows the results of evaluation of the concentration dependence of berbamine and its derivatives on the number of viable cells under feeder-free culture conditions.
Figure 9:
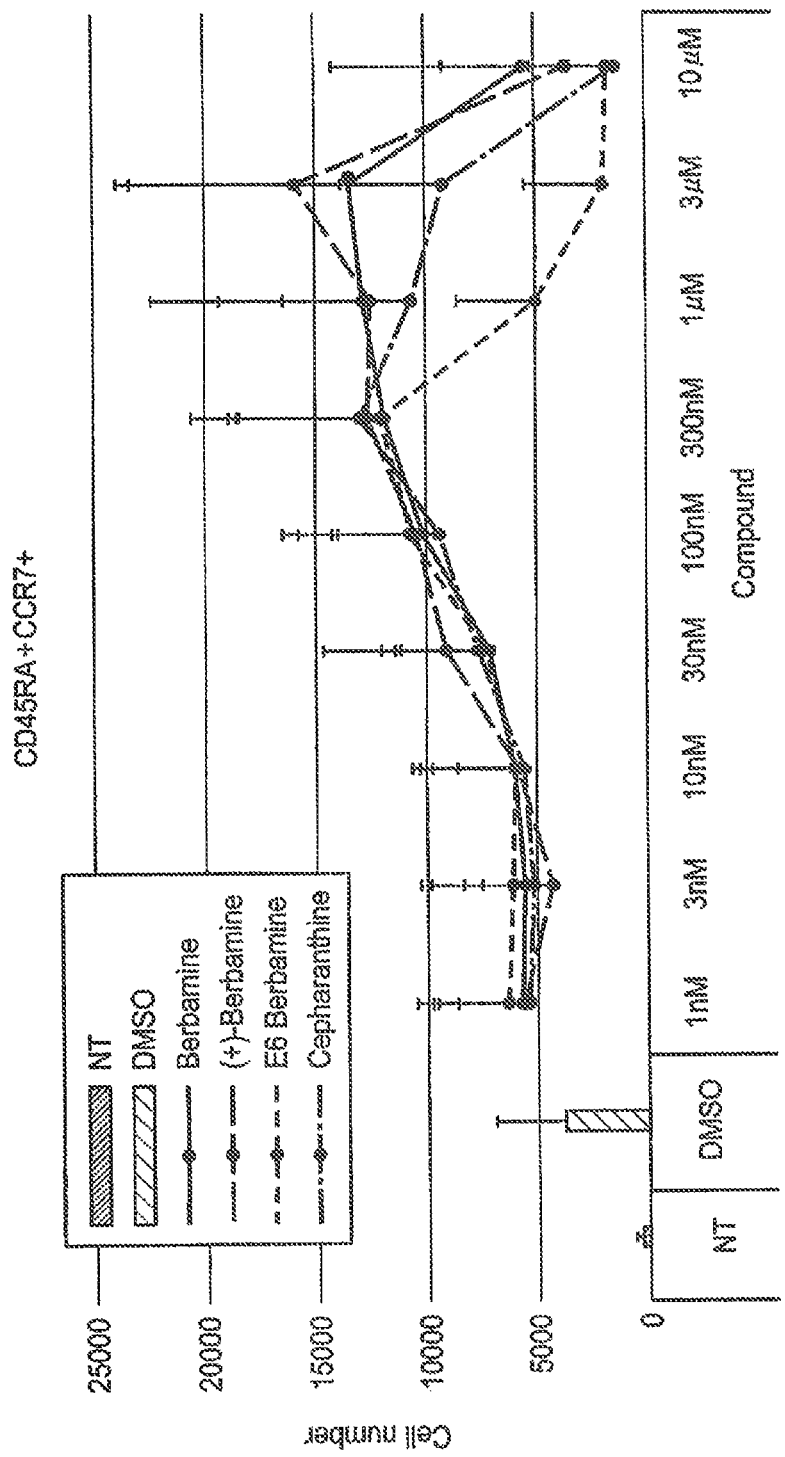
FIG. 9 shows the results of evaluation of the concentration dependence of berbamine and its derivatives on the number of undifferentiated cells under feeder-free culture conditions.

As shown in FIG. 8, the number of viable cells increased in a concentration-dependent manner of the bisbenzylisoquinoline alkaloid represented by the formula (X-1) or the formula (X-2), and the highest proliferation effect was observed at 1 µM. Further, as shown in FIG. 9, the number of undifferentiated cells increased in a concentration-dependent manner of the bisbenzylisoquinoline alkaloid of the formula (I), and the highest proliferation effect was observed at 1 µM. Therefore, it was determined that all the subsequent examinations were performed by setting the concentration of the bisbenzylisoquinoline alkaloid represented by the formula (X-1) or the formula (X-2) in the culture medium to 1 µM.

Example 7

Comparison with PBMC Feeder

By using T-iPS-T cells, a proliferation promoting effect was compared by culturing the cells using the following three methods: the same stimulation method as in Example 2 using PBMC feeder, the same stimulation method as in Example 4 using CD3/CD28 Dynabeads, and the same stimulation method as in Example 4 in which berbamine (SIGMA, 547190) at 1 µM was added to CD3/CD28 Dynabeads. The PBMC feeder cells were labeled using CellTrace CFSE Cell Proliferation Kit for Flow Cytometry (CFSE, Invitrogen, 100 nM) in order to discriminate them from T-iPS-T cells, and then, a radiation irradiation treatment was performed.

Figure 10:
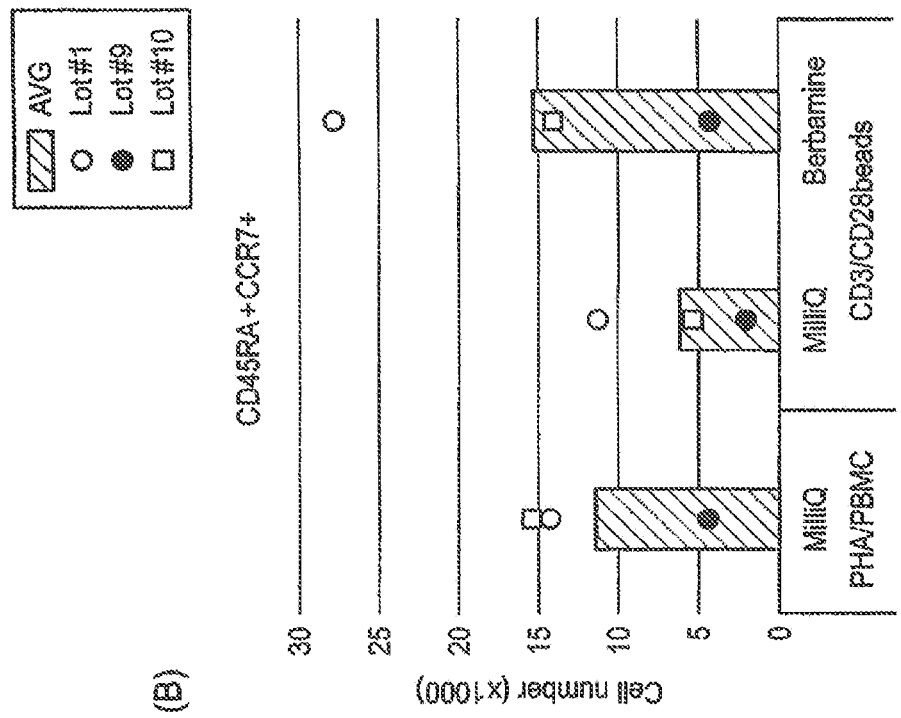
FIGS. 10(A) and 10(B) show the results of comparison of the following three methods using T-iPS-T cells: a stimulation method using PBMC feeder, a stimulation method using CD3/CD28 Dynabeads, and a stimulation method in which berbamine at 1 µM was added to CD3/CD28 Dynabeads.

The results of staining and measurement performed in the same manner as in Example 5 are shown in FIGS. 10(A) and 10(B). As shown in FIGS. 10(A) and 10(B), by culturing the cells in the presence of berbamine, as compared with the presence of the feeder cells, a significant increase in the number of viable cells was observed, and comparable results were obtained for the number of undifferentiated cells. From the above results, it can be said that the present invention can substitute PBMCs which have been conventionally used for the proliferation of T cells.

Example 8

Screening for Low-Molecular Weight Compound

In order to further evaluate the results obtained in Example 4, reproducibility was evaluated. As a method therefor, the same method as in Example 4 was used to carry out culturing and evaluation. As compounds, 20 compounds were selected and used among the compounds used in Example 4 including berbamine, and DMSO (0.1%) that is a solvent for the compound was used as a control. Note that in a statistical analysis, a Student's t-test was used (*: $p<0.05$). The results are shown in FIG. 11.

Figure 11:
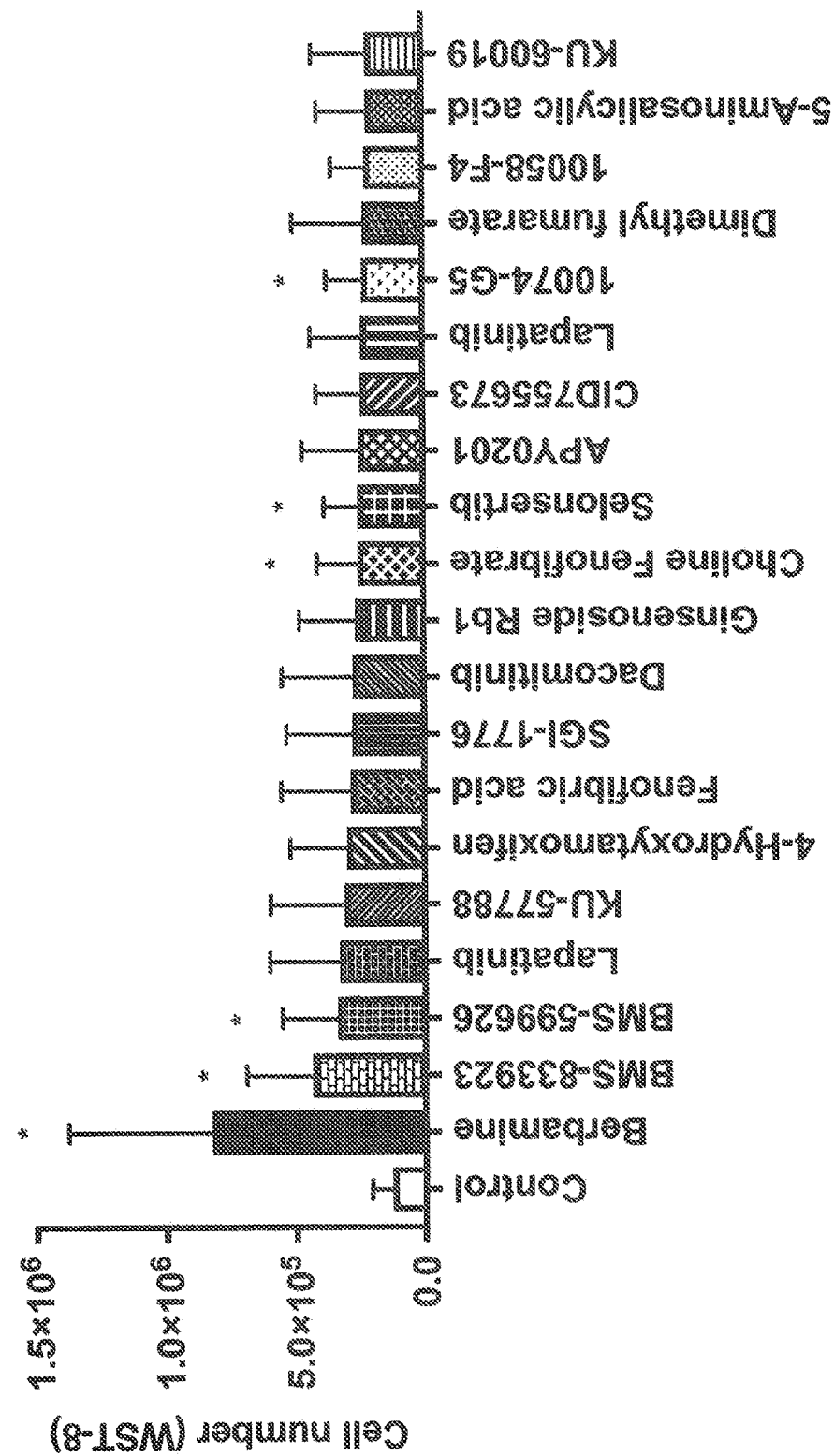
FIG. 11 shows the results of analysis of the effect of a low-molecular weight compound on the proliferation of T-iPS-T cells under feeder-free culture conditions using the number of viable cells as an index.

As shown in FIG. 11, a significant increase in the number of cells was observed when using a plurality of compounds including berbamine at the first place as compared with DMSO, and it was found that berbamine enhances the proliferation of iPS-T cells as compared with DMSO.

Example 9

Comparison with Known Compound Contributing to Proliferation of Memory T Cells

The effect on culturing of T-iPS-T cells was evaluated by comparing a known compound that contributes to the proliferation of memory T cells with berbamine. As a method therefor, T-iPS-T cells after 1st expansion were stimulated with CD3/CD28 Dynabeads in the same manner as in Example 4, and any of TWS119 (Cayman, 6015114-19-6) (for example, Gattinoni et al., Nat. Med., 15(7): 808-813, 2009), (+)-JQ1 (abcam, ab146612) (for example, Gattinoni et al., Nat. Med., 15(7): 808-813, 2009), each of which is known as a known compound, and berbamine (BBM, SIGMA, 547190) was added at 1 µM. DMSO (0.1%) that is a solvent for the compound was used as a control.

After culturing for 6 days in the same culture medium as in Example 6, the cells were stained and measured by the method in Example 5. The number of events of PI-negative cells and the number of events of CD45RA(+)CCR7(+) cells in the PI-negative cells, which were analyzed by FlowJo 9, were used as data. Note that in a statistical analysis, a Student's t-test was used (*: $p<0.05$). The results are shown in FIGS. 12(A) and 12(B).

As shown in FIGS. 12(A) and 12(B), in the T-iPS-T cells, the above-mentioned known compounds did not contribute to proliferation, and only berbamine exhibited a significant proliferation effect. With respect to the (+)-JQ1 (abcam, ab146612) compound, the evaluation was carried out also at 0.15 µM, but the result was similar to that obtained at 1 µM.

From the above results, it was indicated that berbamine is useful for culturing and producing T cells as compared with the known compounds.

Example 10

Effect of Combined Use with MAPK Cascade Inhibitor on Proliferation of Memory T Cells The effect of the combined use of berbamine with a MAPK cascade inhibitor on the proliferation of memory T cells was examined. As a method therefor, T-iPS-T cells after 1st expansion were stimulated with CD3/CD28 Dynabeads in the same manner as in Example 4, and berbamine (BBM) and CEP-32496 (ERK cascade inhibitor, Cayman, 18776), SB-203580 (p38 cascade inhibitor, Cayman, 13344), Losmapimod (p38 cascade inhibitor, Cayman, 13614), or ZM-336372 (ERK cascade inhibitor, Cayman, 10010367) were used in combination and added thereto. The final concentration of each compound was set to 1 µM. DMSO (0.1%) that is a solvent for the compound was used as a control.

After culturing for 6 days in the same culture medium as in Example 6, the cells were stained and measured by the method in Example 5. The number of events (#Cells) of CD45RA(+)CCR7(+) cells in the PI-negative cell population analyzed by FlowJo 9 was plotted and graphed. Note that in a statistical analysis, a Student's t-test was used (*: $p<0.05$, $P<0.01$, *$P<0.001$, ****$P<0.0001$). The results are shown in FIG. 13.

Figure 13:
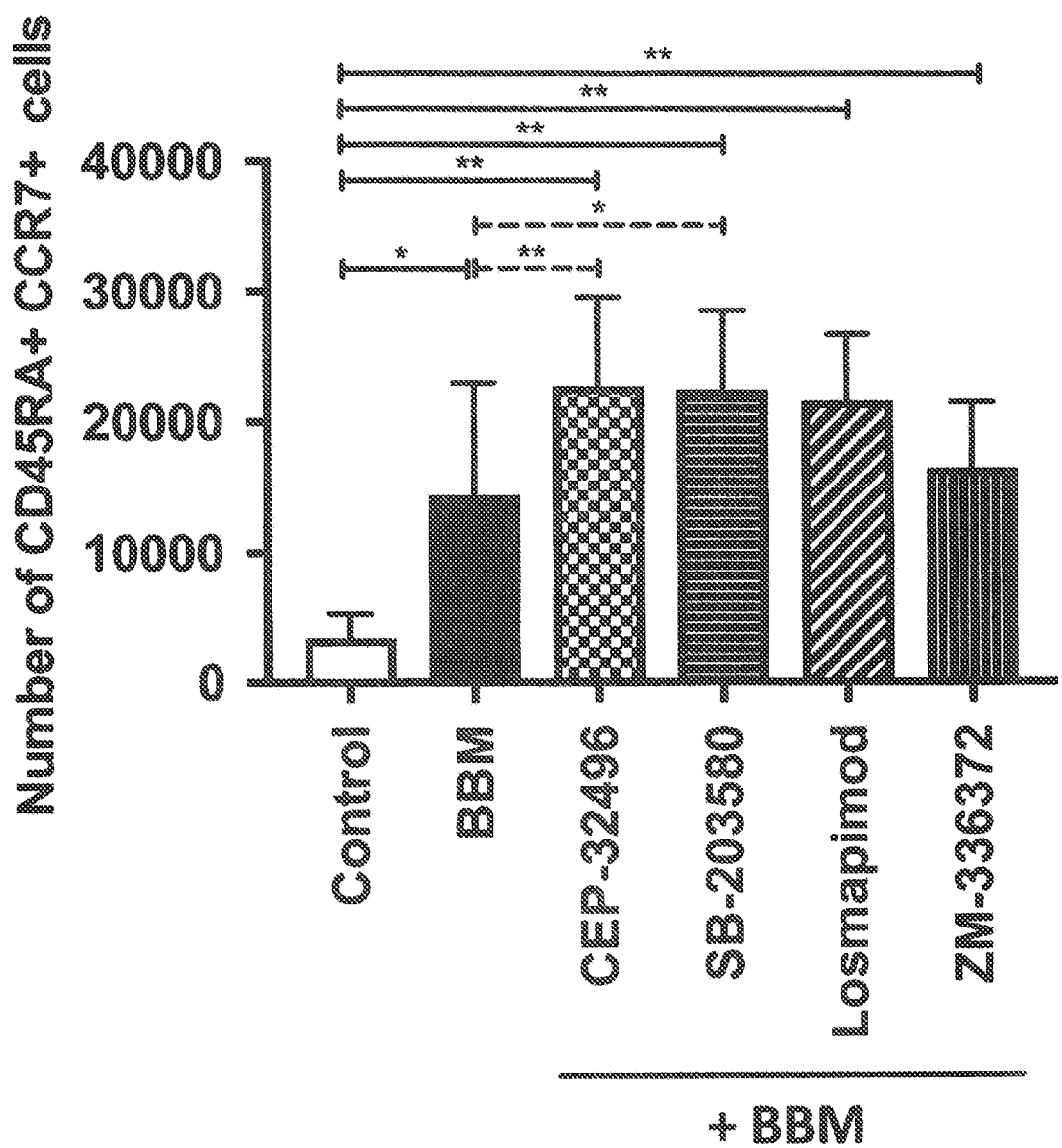
FIG. 13 shows the results of examination of the effect of combined use of berbamine with a MAPK cascade inhibitor on the proliferation of memory T cells.

As shown in FIG. 13, significant cell proliferation was observed under all combined use conditions in addition to the berbamine single agent as compared with DMSO, and enhancement of cell proliferation was observed more under all combined use conditions than in the case of the berbamine single agent.

From the above results, it was indicated that the proliferation of memory T cells can be further enhanced by the combined use of berbamine with a MAPK cascade inhibitor such as an ERK cascade inhibitor or a p38 cascade inhibitor as compared with berbamine alone.

Example 11

Effect of Berbamine Derivative on Proliferation of T Cells

The effect of a berbamine derivative on the proliferation of T cells was verified. As a method therefor, T-iPS-T cells after 1st expansion were cultured in the same manner as in Example 4, and berbamine (BBM) or each of 13 types of derivatives [BBMD1 to 13, Hebei Sundia MediTech Company Ltd.] was added thereto (one type per well) at a final concentration of 0.1 nM, 1 nM, 10 nM, 100 nM, or 1 µM, and then, the cells were cultured at 37° C. under 5% $CO_2$. DMSO (0.1%) that is a solvent for the compound was used as a control.

After culturing for 6 days, the number of viable cells was measured using Cell Count Reagent SF (Nacalai Tesque, 07553) and a microplate reader (SoftMax Pro 5. X, Molecular Devices, 450 nm/650 nm), and the OD value was used as data. Note that in a statistical analysis, a Student's t-test was used (*: $p<0.05$). The results are shown in Table. 1.

Reference No. in Table 1 is as follows.
1. Xie et al., Eur J Med Chem, 44(8: 3293-8, 2009
2. Tan et al., International Journal of Mass Spectrometry, 386: 37-41, 2015
3. Nam et al., Mol Oncol, 6(5): 484-93, 2012

In Table 1, the values with respect to DMSO were calculated and rounded off to the third decimal place. In Table 1, *$P<0.05$, $P<0.01$, *$P<0.001$, and ***$P<0.0001$. In addition, the statistical analysis was also performed with respect to Example 6 in the same manner. The results are shown in Table 2.

TABLE 1

| | 0.1 nM | 1 nM | 10 nM | 100 nM | 1 µM | Reference No. |
|---|---|---|---|---|---|---|
| BBM | 0.257 ± 0.018 | 0.266 ± 0.024 | 0.275 ± 0.019 * | 0.282 ± 0.031 * | 0.505 ± 0.034 *** | 1 |
| BBMD1 | 0.257 ± 0.024 | 0.268 ± 0.009 * | 0.289 ± 0.033 * | 0.415 ± 0.039 ** | 0.529 ± 0.101 ** | 1 |
| BBMD2 | 0 264 ± 0.010 * | 0.269 ± 0.059 | 0.295 ± 0.028 * | 0.437 ± 0.059 ** | 0.493 ± 0.036 *** | 1 |
| BBMD3 | 0.245 ± 0.013 | 0.298 ± 0.021 * | 0.325 ± 0.077 | 0.581 ± 0.025 **** | 0.195 ± 0.002 | 1 |
| BBMD4 | 0.234 ± 0.024 | 0.245 ± 0.037 | 0.286 ± 0.019 * | 0.470 ± 0.023 *** | 0.470 ± 0.053 ** | 1 |
| BBMD5 | 0.246 ± 0.001 | 0.245 ± 0.016 | 0.285 ± 0.032 * | 0.477 ± 0.064 ** | 0.186 ± 0.001 | 1 |
| BBMD6 | 0.248 ± 0.019 | 0.248 ± 0.016 | 0.290 ± 0.023 * | 0.472 ± 0.077 ** | 0.208 ± 0.004 | 1 |
| BBMD7 | 0.230 ± 0.018 | 0.266 ± 0.013 * | 0.258 ± 0.024 | 0.346 ± 0.041 ** | 0.550 ± 0.026 **** | 2 |
| BBMD8 | 0.268 ± 0.022 * | 0.227 ± 0.028 | 0.261 ± 0.029 | 0.326 ± 0.051 * | 0.462 ± 0.027 *** | 3 |
| BBMD9 | 0.264 ± 0.030 | 0.255 ± 0.004 * | 0.221 ± 0.017 | 0.268 ± 0.020 * | 0.328 ± 0.016** | 3 |
| BBMD10 | 0.255 ± 0.013 | 0.274 ± 0.007 ** | 0.295 ± 0.023 * | 0.494 ± 0.038 *** | 0.301 ± 0.008 ** | 3 |
| BBMD11 | 0.270 ± 0.099 | 0.242 ± 0.046 | 0.300 ± 0.081 | 0.425 ± 0.079 * | 0.239 ± 0.076 | 3 |
| BBMD12 | 0.185 ± 0.072 | 0.234 ± 0.027 | 0.235 ± 0.010 | 0.257 ± 0.008 * | 0.561 ± 0.035 *** | 3 |
| BBMD13 | 0.253 ± 0.022 | 0.292 ± 0.001 ** | 0.260 ± 0.011 * | 0.412 ± 0.085 * | 0.288 ± 0.041 | 1 |
| DMSO | 0.225 ± 0.017 | | | | | |

TABLE 2

| | 1 nM | 3 nM | 10 nM | 30 nM | 100 nM |
|---|---|---|---|---|---|
| Cell number | | | | | |
| Berbamine | 18397 ± 10723 | 19540 ± 11587 | 24672 ± 10675 ** | 30885 ± 12249 ** | 48026 ± 6597 ** |
| (+)-Berbamine | 19064 ± 8563 | 16889 ± 10498 | 21727 ± 12682 * | 32578 ± 10874 * | 43590 ± 6129 ** |
| E6 Berbamine | 20795 ± 11427 ** | 19420 ± 9845 ** | 22404 ± 11035 *** | 28009 ± 13327 * | 44562 ± 11985 ** |
| Cepharanthine | 18312 ± 7127 | 19212 ± 8368 | 20590 ± 9995 | 29158 ± 12980 * | 41856 ± 9113 ** |
| DMSO | 16096 ± 10785 | | | | |
| Number of CD45RA+CCR7+ cells | | | | | |
| Berbamine | 5761 ± 4045 | 5667 ± 4255 | 6186 ± 3617 | 7186 ± 4180 * | 10224 ± 3801 ** |
| (+)-Berbamine | 5705 ± 3931 | 4438 ± 3092 | 5650 ± 4529 | 9173 ± 5555 | 10581 ± 5279 * |
| E6 Berbamine | 6440 ± 4121 * | 6205 ± 4137 * | 6015 ± 4682 | 7410 ± 4691 * | 10775 ± 5788 * |
| Cepharanthine | 5429 ± 3207 ** | 5256 ± 3168 | 5632 ± 3014 *** | 7764 ± 3495 ** | 9486 ± 4802 * |
| DMSO | 3891 ± 3170 | | | | |

TABLE 2-continued

|  | 300 nM | 1 μM | 3 μM | 10 μM |
|---|---|---|---|---|
| Cell number | | | | |
| Berbamine | 54888 ± 5691 ** | 43432 ± 23926 | 43656 ± 29882 | 20559 ± 34130 |
| (+)-Berbamine | 52032 ± 4158 ** | 55822 ± 2871 ** | 50338 ± 14996 * | 12254 ± 20583 |
| E6 Berbamine | 55682 ± 3508 ** | 26964 ± 23925 | 16367 ± 26569 | 8441 ± 16764 |
| Cepharanthine | 52923 ± 5313 ** | 48800 ± 17971 * | 31965 ± 19694 | 4884 ± 8378 |
| DMSO | | | | |
| Number of CD45RA+CCR7+ cells | | | | |
| Berbamine | 12034 ± 6515 * | 12957 ± 9483 | 13552 ± 10355 | 5650 ± 8552 |
| (+)-Berbamine | 12675 ± 6249 * | 12638 ± 6767 * | 15981 ± 7397 * | 3692 ± 5579 |
| E6 Berbamine | 12148 ± 6414 * | 5075 ± 3582 | 2080 ± 3520 | 1791 ± 3538 |
| Cepharanthine | 13060 ± 7584 * | 10741 ± 5793 | 9245 ± 4682 * | 1447 ± 2117 |
| DMSO | | | | |

As shown in Table 1 and Table 2, in all the 16 types of derivatives, significant enhancement of cell proliferation was observed as compared with DMSO. From the results, it was found that berbamine and its derivatives are useful for the production of T cells.

Example 12

Long-Term Culturing of T-iPS-T Cells

The possibility of long-term culturing of T-iPS-T cells using berbamine was evaluated. The experimental scheme is shown in FIG. 14(A). First, T cells were induced from T-iPS cells without using a feeder. For the maintenance of iPS cells, StemFit AK02N medium (Ajinomo) was used for feeder-free iPS cells. The iPS cells were detached from the culture surface coated with iMatrix-511 using a dissociation agent [1× TrypLE Select (Thermo Fisher Scientific) was diluted to 1/2 with PBS, and a 0.5 mol/L EDTA solution (pH 8, Nacalai Tesque) was added thereto to give a final concentration of 0.5× TrypLE Select and 0.75 mM EDTA], and subcultured in a culture medium obtained by adding 10 μM Y-27632 to StemFit AK02N (37° C., 5% $CO_2$). On the following day, the culture medium was replaced with Stemfit AK02N. This operation was repeated once a week to maintain the iPS cells.

Hematopoietic progenitor cells (HPCs) were produced by inducing the differentiation of iPS cells by an embryoid body formation method. The feeder-free iPS cells were detached with 0.5× TrypLE Select, and 0.75 mM EDTA, and then seeded at 2 to 3×10⁵ cells/well in a 6-well plate (CORNING) subjected to an ultra-low adhesion treatment. By using Stemfit AK02N medium supplemented with 10 μM Y-27632 (Nacalai Tesque) and 10 μM CHIR99021 (Tocris Bioscience), the cells were cultured under low oxygen conditions (5% 02) (Day 0).

On the following day, 50 ng/mL BMP-4 (Miltenyi Biotec), 50 ng/mL VEGF-165A (Wako), and 50 ng/mL bFGF (Wako) were added to StemPro34 (Thermo Fisher Scientific) medium (EB medium) supplemented with 1× Insulin, Transferrin, Selenium Solution (Thermo Fisher Scientific), 1× Glutamax (Thermo Fisher Scientific), 0.2×PSG, and 45 mM monothioglycerol (Wako), and the cells were cultured (Day 1, 5% $O_2$).

On the following day, 6 μM SB431542 (Wako) was added thereto, and the cells were cultured (Day 2, 5% $O_2$). After 2 days, the cells were cultured in EB medium supplemented with 50 ng/mL VEGF-165A, 50 ng/mL bFGF, and 50 ng/mL SCF (Day 4, 5% $O_2$).

After two days, the cells were cultured in EB medium supplemented with 50 ng/mL VEGF-165A, 50 ng/mL bFGF, 50 ng/mL SCF, 30 ng/mL TPO (Wako), and 10 ng/mL FLT3L (Wako) (Day 6). Thereafter, the cells were cultured under 5% $CO_2$ until Day 8.

By using the obtained HPCs, CD4(+)CD8(+) T cells were obtained by differentiation induction. The HPCs were seeded at 2,000 to 3,000 cells/well in a 48-well plate coated with Fc-DLL4 (5 μg/mL, Sino Biological, Inc.) and Retronectin (5 μg/mL, Takara Bio).

The cells were cultured for 21 days using alpha-MEM medium supplemented with 50 ng/mL SCF (Wako), 50 ng/mL IL-7 (Wako), 50 ng/mL Flt3L (Wako), 100 ng/mL TPO (Wako), 30 μM SDF-1α (Wako), 15 μM SB203580 (Tocris Bioscience), 55 μM 2-mercaptoethanol (Wako), 50 μg/mL PAA, 15% FBS, and 1% PSG A new plate coated with Fc-DLL4 and Retronectin was prepared every week, and the cells were reseeded in the plate. The culture medium was replaced every 2 to 3 days.

Subsequently, CD8beta(+)CD8alpha(+) T cells were induced. Specifically, cells including the above CD4(+)CD8 (+) T cells were seeded in a 48-well plate, and cultured in alpha-MEM medium supplemented with 500 ng/mL of an anti-CD3 antibody OKT3 (eBioscience), 10 nM Dexamthasone (Dexate R, Fuji Pharma), 10 ng/mL IL-7 (Wako), 50 μg/mL PAA, 15% FBS, and 1% PSG After 3 days, the culture medium was replaced with 10 ng/mL IL-7 (Wako), 50 μg/mL PAA, 15% FBS, and 1% PSG, and the cells were cultured. After 7 days, the cells were stained with CD8 beta-PE (Beckman) and CD8 alpha-FITC (BD Bioscience) to sort the CD8beta(+)CD8alpha(+) T cells.

The CD8beta(+)CD8alpha(+) T cells (1,500 cells/well) obtained by feeder-free differentiation induction were seeded, stimulated with CD3/CD28 Dynabeads in the same manner as in Example 4, and berbamine (BBM) at 1 μM or MilliQ water that is a solvent for the compound as a control was added thereto, and the cells were cultured in the same culture medium as in Example 6. On day 14, day 28, and day 42, the cells were collected, the number of viable cells was counted by a trypan blue method, and the cells were restimulated and cultured. The cells were collected on day 56, and the number of viable cells was counted. The results are shown in FIG. 14(B).

As shown in FIG. 14(B), in the case of the cells cultured by adding MilliQ water, a decrease in viability was observed with each stimulation, and the cells could not be cultured after day 42. On the other hand, the cells cultured by adding berbamine could be cultured for 56 days, and further, enhancement of the proliferation of T-iPS-T cells was also observed.

Figure 15:
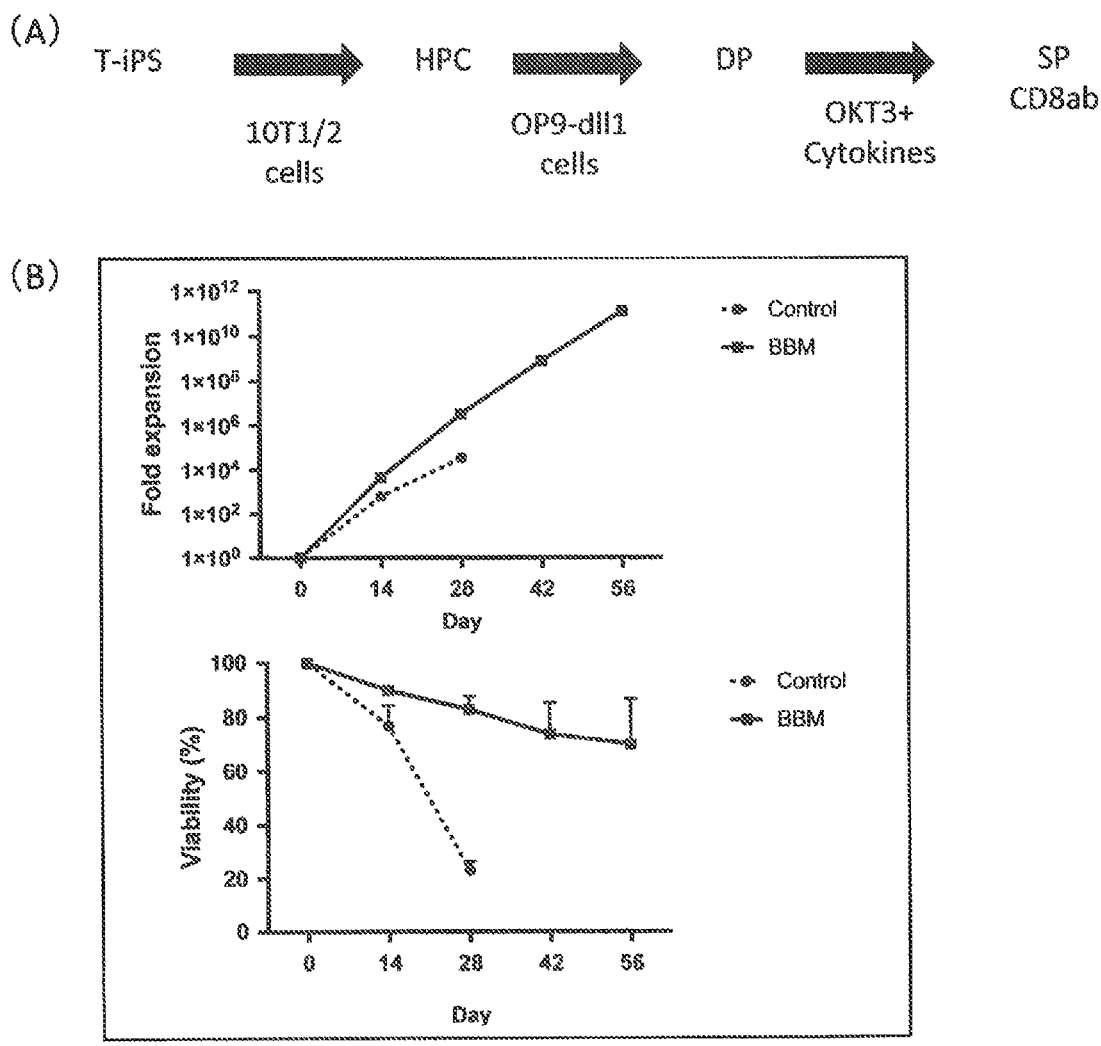
FIG. 15(A) shows an experimental scheme of evaluation of feeder long-term culturing of T-iPS-T cells using berbamine.
FIG. 15(B) shows the results.

Further, evaluation of T-iPS-T cells obtained by differentiation induction using a feeder was also performed. The experimental scheme is shown in FIG. 15(A). The T-iPS-T cells (1,500 cells/well) obtained by differentiation induction in Example 1 were seeded, and stimulated with CD3/CD28 Dynabeads in the same manner as in Example 4, and berbamine (BBM) at 1 µM or MilliQ water that is a solvent for the compound as a control was added thereto, and the cells were cultured in the same culture medium as in Example 6. The cells were collected on day 14, day 28, and day 42, and the number of viable cells was counted by a trypan blue method, and the cells were restimulated and cultured. The cells were collected on day 56, and the number of viable cells was counted. The results are shown in FIG. 15(B).

As shown in FIG. 15(B), in the case of the cells cultured by adding MilliQ water, a decrease in viability was observed with each stimulation, and the cells could not be cultured after day 28. On the other hand, the cells cultured by adding berbamine could be cultured for 56 days, and further, enhancement of the proliferation of the cells was also observed.

Conventionally, for the proliferation of T cells, a method using PBMCs derived from a healthy human subject as a feeder shown in Examples 2 and 7 has been used (NPL 1). As a result of this Example, by the addition of berbamine, long-term proliferation of T cells could be achieved without using PBMCs, and further, enhancement of cell proliferation was observed.

From the above results, it was indicated that cell proliferation using berbamine can not only substitute human PBMCs having been used for the proliferation of T cells but also produce more cells as a result of long-term cell proliferation.

Example 13

Effect on Proliferation of Primary T Cells

Figure 16:
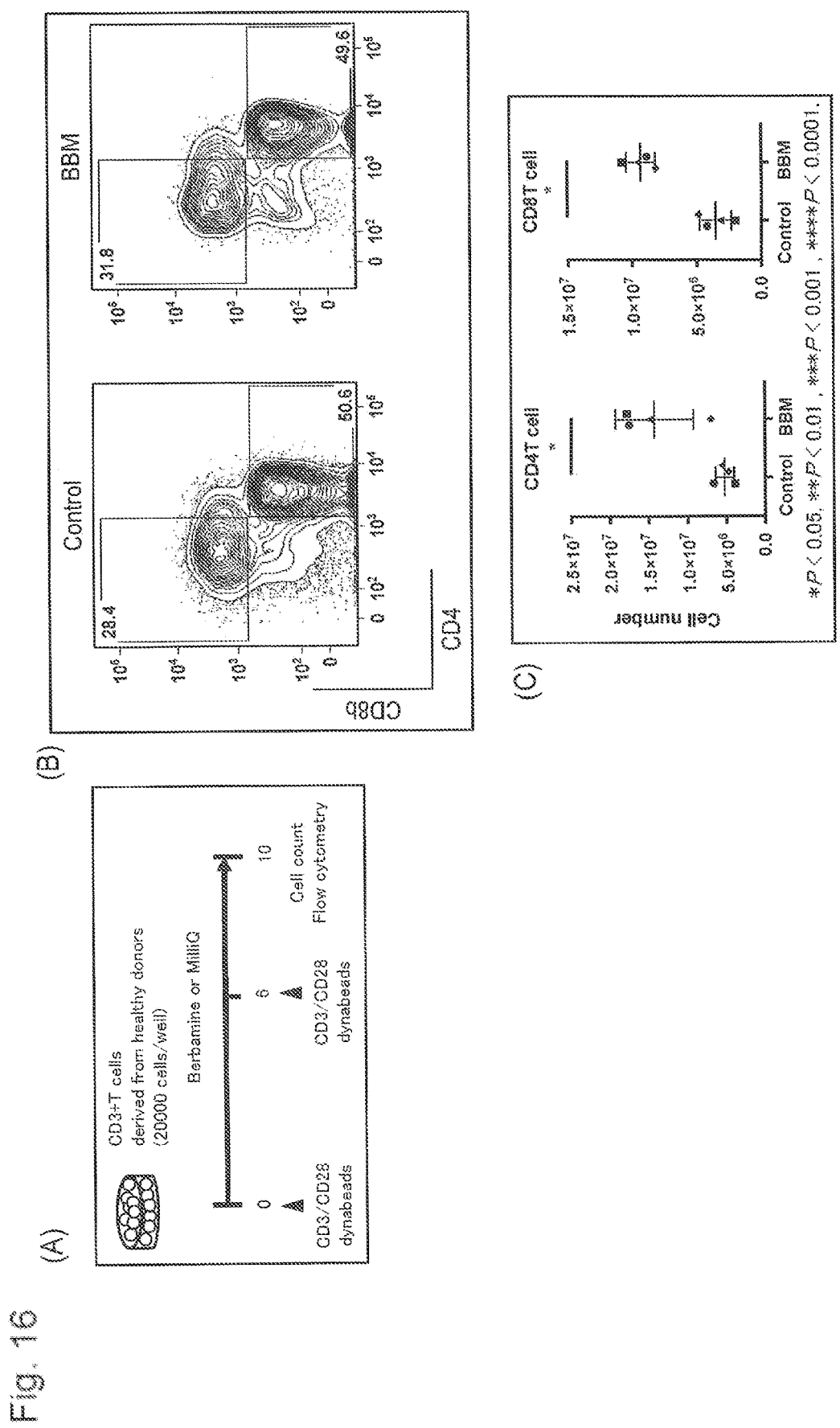
FIG. 16(A) shows an experimental scheme of evaluation of the effect of berbamine on the proliferation of primary T cells (CD4 T and CD8 T cells)
FIGS. 16(B) and 16(C) show the results.

The effect of berbamine on proliferation of primary T cells (CD4 T, CD8 T cells) was examined. The experimental scheme is shown in FIG. 16(A). As a method therefor, CD3 T cells were purified from PBMCs (CTL, Inc.) using Pan T Cell Isolation Kit, human (Miltenyi, 130-096-535). The purified CD3 T cells (20,000 cells/well) were seeded, and berbamine (BBM) at 1 µM or MilliQ water that is a solvent for the compound as a control was added thereto, and the cells were stimulated with CD3/CD28 Dynabeads (60,000 beads/well).

The cells were cultured for 6 days in the same culture medium as in Example 6 and restimulated. After the cells were further cultured for 4 days, the number of viable cells was counted by a trypan blue method and the ratios of CD4-positive cells and CD8-positive cells were analyzed by FACS. In the FACS, the cells cultured with the compound were transferred to a 96-well plate, washed with a staining solution (PBS containing 2% FBS), and then stained with CD4-BV421 (BioLegend, 305622) and CD8β-PE (Beckman, IM2217U).

After washing, the cells were resuspended in 200 µL/well of the staining solution containing PI. The suspension in an amount of 100 µL/well was analyzed using a BD LSR Fortessa cytometer (BD Bioscience) equipped with HTS, and all cells were recorded.

The value obtained by multiplying the positive rate of CD8(+) or CD4(+) cells in the PI-negative cell population analyzed by FlowJo 9 by the number of viable cells was defined as the number of CD8-positive cells or the number of CD4-positive cells. Note that in a statistical analysis, a Student's t-test was used (*: $p<0.05$). The results are shown in FIGS. 16(B) and 16(C).

As shown in FIGS. 16(B) and 16(C), by culturing the primary T cells with berbamine, in both CD4 T and CD8 T cells, significant enhancement of cell proliferation was observed as compared with MilliQ water. The CD4 T cells include Th0, Th1, Th2, Th9, Th17, Th22, Tfh, Treg, and the like. The CD8 T cells include Tc, Tc1, Tc2, Tc17, and the like.

From the above results, it was indicated that berbamine enhances the proliferation of CD4 T and CD8 T cells as compared with MilliQ water.

Example 14

Usefulness in Proliferation of Regulatory T Cells

The usefulness of berbamine (BBM) in the proliferation of regulatory T cells (Treg) was verified. As a method therefor, CD3 T cells were purified from PBMCs (CTL, Inc.) derived from 3 healthy donor subjects in the same manner as in additional Example 6 and cultured for 6 days. After culturing for 6 days, the number of viable cells was counted by a trypan blue method and the ratio of CD25(+)FoxP3(+) cells was analyzed by FACS.

In the FACS, the cultured cells were sorted into facs tubes, washed with a staining solution (PBS containing 2% FBS), and then stained with CD3-APC (BioLegend, 300421), CD4-BV510 (BioLegend, 317444), CD8-Pacific Blue (BD 558207), and CD25-FITC (BioLegend, 302604).

After the cells were further washed, intracellular staining was performed using FoxP3/Transcription Factor Staining Buffer Set (eBioscience, 00-5523) and FoxP3-PE (eBioscience, 12-4776-41), and measurement was performed using a BD LSRFortessa cytometer (BD Bioscience).

The value obtained by multiplying the positive rate of FoxP3(+) cells in the CD4(+) cells analyzed by FlowJo 9 by the number of viable cells was defined as the number of FoxP3-positive cells. The results are shown in FIGS. 17(A) and 17(B).

As shown in FIGS. 17(A) and 17(B), by berbamine, an increase in the number of FoxP3-positive cells was observed in all the three donors as compared with MilliQ water.

From the above results, it was indicated that berbamine enhances the proliferation of Treg as compared with MilliQ water.

Example 15

Analysis of T Cells on which Berbamine Particularly Acts

Figure 18A:
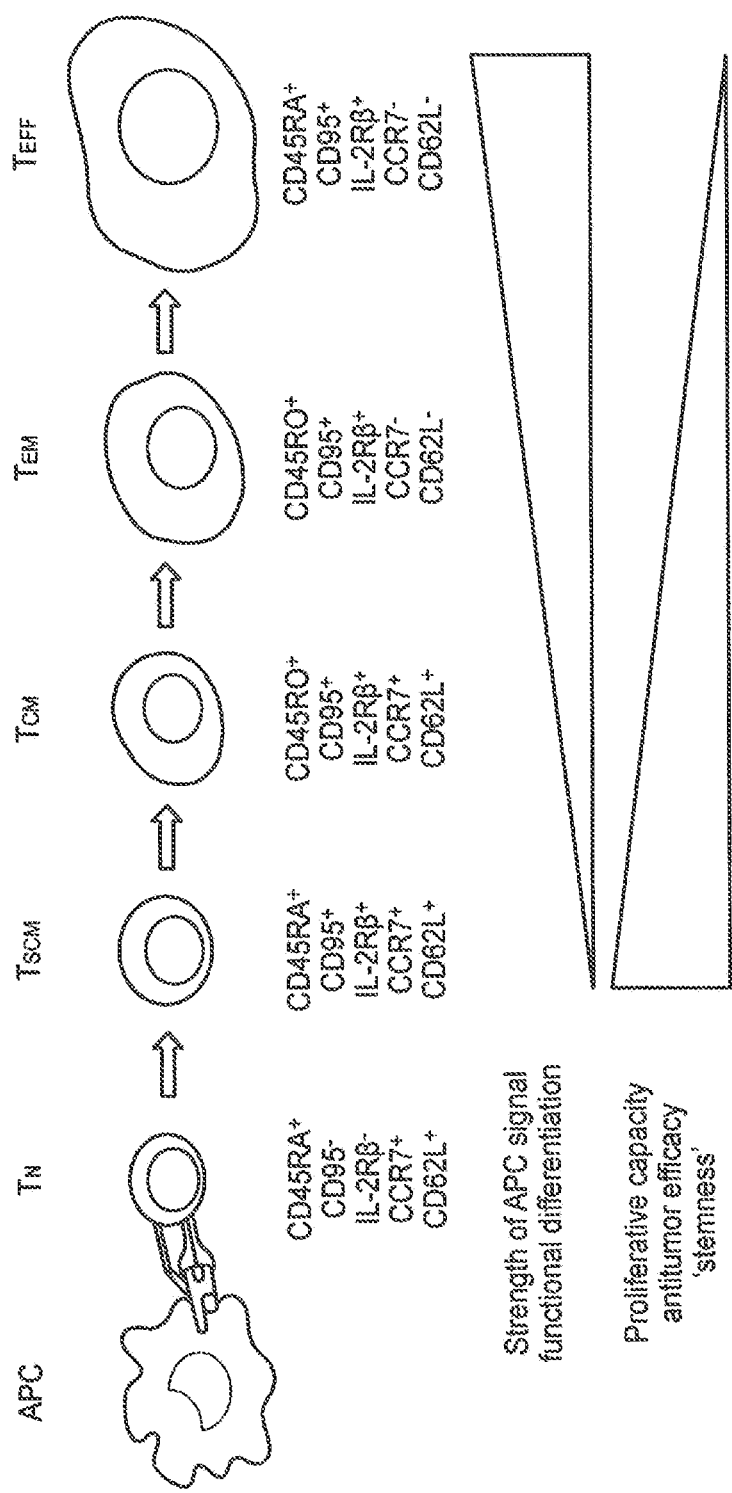
FIG. 18A is a schematic view showing the hierarchy of T cells.

NPL 4 reports that hierarchy exists in T cells (FIG. 18A). In this Example, a fraction in which berbamine acts in T cells was verified. As a method therefor, PBMCs (CTL, Inc.) derived from a healthy subject was washed with a staining solution (PBS containing 2% FBS) and then stained with CCR7-APC (BioLegend, 353214), CD45RA-BV510 (BioLegend, 304142), CD45RO-APC-Cy7 (BioLegend, 307228), CD95-PC-Cy7 (BioLegend, 305622), CD8β-PE (Beckman, IM2217U), and CD4-BV421 (BioLegend, 317434).

After washing, the cells were resuspended in the staining solution containing PI, and by using BD AriaII Cell Sorter (BD Bioscience), in the CD8β(+) cells, CCR7(+)CD45RA (+)CD95(−)CD45RO(−) was sorted as naive T cells, CCR7 (+)CD45RA(+)CD95(+)CD45RO(+) was sorted as stem cell memory T cells, CCR7(+)CD45RA(−)CD45RO(+) was sorted as central memory T cells, and CCR7(−) CD45RA (−)CD45RO(+) was sorted as effector memory T cells.

The respective cells (about 3,000 cells/well) were seeded, and berbamine (BBM) at 1 µM or MilliQ water that is a solvent for the compound as a control was added thereto, and the cells were stimulated with CD3/CD28 Dynabeads (about 9,000 beads/well). The cells were cultured using the same culture medium as in Example 6.

After 6, 9, 12, and 14 days of culturing, the number of viable cells was counted by a trypan blue method. In a statistical analysis, a Student's t-test was used (*: p<0.05). The gating at the time of sorting is shown in FIG. 18B, and the results of cell count are shown in FIG. 18C.

Figure 18B:
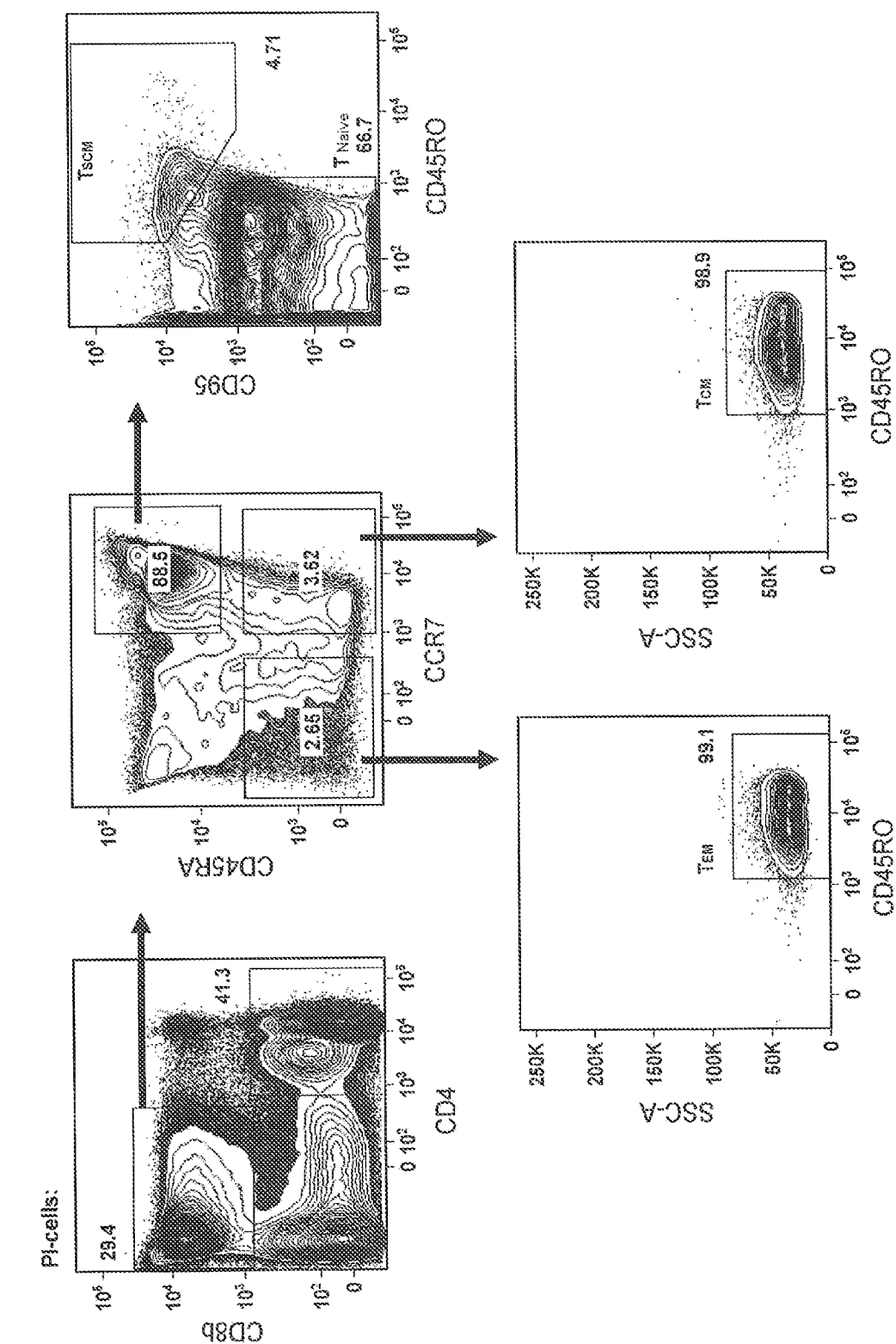
FIG. 18B shows the results of verification of a fraction in which berbamine acts in T cells, and shows gating at the time of sorting.
Figure 18C:
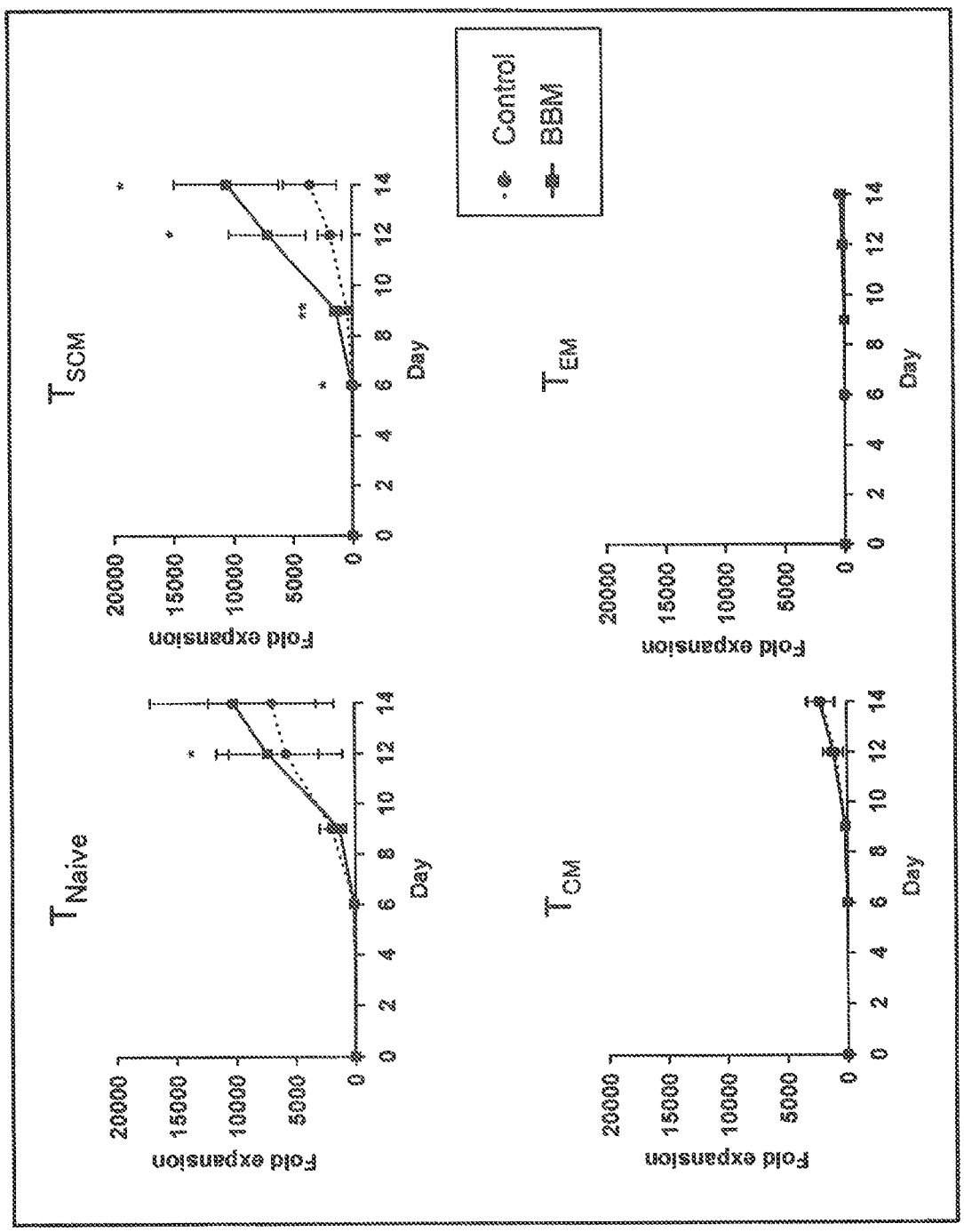
FIG. 18C shows the results of verification of a fraction in which berbamine acts in T cells, and shows the cell count.

As shown in FIGS. 18B and 18C, significant enhancement of cell proliferation by berbamine was observed in the naive T cells and the stem cell memory T cells.

From the above results, it was indicated that berbamine acts on T cells including naive T cells and stem cell memory T cells.

Example 16

Effect on Engraftment of Cells into Mice

The effect of cells cultured with berbamine on engraftment into mice was examined. The experimental scheme is shown in FIG. 19(A). As a method therefor, CD8 T cells were purified from PBMCs (CTL, Inc.) derived from a healthy subject using CD8 T Cell Isolation Kit, human (Miltenyi, 130-096-495).

The purified CD8 T cells (20,000 cells/well) were seeded, and berbamine (BBM) at 1 µM or MilliQ water that is a solvent for the compound as a control was added thereto, and the cells were cultured in the same culture medium by the same stimulation method as in additional Example 6, and the cells cultured for 10 days were used as cells to be transplanted.

NSG male mice at 6 to 11 weeks of age (Charles River Japan) were used as experimental animals and transplantation was performed through the tail vein (approximately $4 \times 10^6$ cells). Two weeks after the transplantation, the spleen, peripheral blood and bone marrow were collected, and the CD8β and CD45 positive rates were analyzed by FACS.

In the FACS, after the spleen and bone marrow were subjected to a homogenization treatment, and the peripheral blood was subjected to a hemolysis treatment, the resulting materials were transferred to a 96-well plate, followed by washing with a staining solution (PBS containing 2% FBS), and then staining with CD8β-PE-cy7 (eBioscience, 25-5273-42) and CD45-APC-Cy7 (BioLegend, 304014).

After washing, the cells were resuspended in the staining solution containing PI. An analysis was performed using a BD LSR Fortessa cytometer (BD Bioscience). The positive rate of CD8β(+)CD45(+) cells in the PI-negative cell population analyzed by FlowJo 9 was measured. Note that in a statistical analysis, a Student's t-test was used (*: p<0.05). The results are shown in FIG. 19(B).

As shown in FIG. 19(B), in all the spleen, peripheral blood, and bone marrow, in the case of the cells cultured with berbamine, significant engraftment was observed as compared with the cells cultured with MilliQ water.

From the above results, a possibility that when cells cultured with berbamine are transplanted, in vivo engraftment is enhanced as compared with cells cultured with MilliQ water, and the proliferation thereafter and a therapeutic effect are improved was suggested.

Example 17

Effect on Enhancement of Proliferation of NK Cells

The effect of berbamine on NK cells was examined. The experimental scheme is shown in FIG. 20(A). As a method therefor, NK cells were purified from PBMCs (CTL, Inc.) derived from 3 healthy donor subjects using NK Cell Isolation Kit, human (Miltenyi, 130-092-657).

The NK cells before and after purification were washed with a staining solution (PBS containing 2% FBS) and then stained with CD56-FITC (BioLegend, 362546) and CD3-APC-Cy7 (BioLegend, 300318).

After washing, the cells were resuspended in the staining solution containing propidium iodide and measured using a BD FACSCanto II Flow Cytometer (BD Bioscience). The ratios of CD3(−) and CD56(+) cells in the PI-negative cell population analyzed by FlowJo 10 were confirmed. FACS plots before and after purification of NK cells are shown in FIG. 20(B).

As shown in FIG. 20(B), the ratios of CD3(−) and CD56(+) cells showing NK cells were 90% or more, which were sufficient. The purified NK cells (37,000 cells/well) were seeded, and cultured using MEM Alpha medium (Gibco, 12571-063) supplemented with 15% FBS (Biological Industries, 04-001-1A), L-Ascorbic Acid 2-Phosphate Sesquimagnesium Salt Hydrate (L-asc-2P, 50 µg/mL, nacalai tesque, 13570-66), ITS-G, IL-7 (10 ng/mL), and IL-15 (5 ng/mL).

To the culture medium, berbamine (BBM) at 1 µM or MilliQ water that is a solvent for the compound as a control was added, and after culturing for 14 days, the number of viable cells was counted by a trypan blue method. The results of the cell number after culturing are shown in FIG. 20(C).

As shown in FIG. 20(C), by berbamine, an increase in the number of NK cells was observed in all the 3 donors as compared with MilliQ water.

From the above results, it was indicated that berbamine enhances the proliferation of NK cells as compared with MilliQ water.

While the present invention has been described in detail with reference to specific embodiments, it is apparent to those skilled in the art that various changes and modifications can be made without departing from the spirit and scope of the present invention.

The invention claimed is:

1. A method for producing T cells or NK cells, comprising culturing T cells or NK cells in a culture medium containing a bisbenzylisoquinoline alkaloid represented by the following formula (X-1) or formula (X-2) or a compound resulting from cleavage of one ether bond thereof or a pharmaceutically acceptable salt thereof:

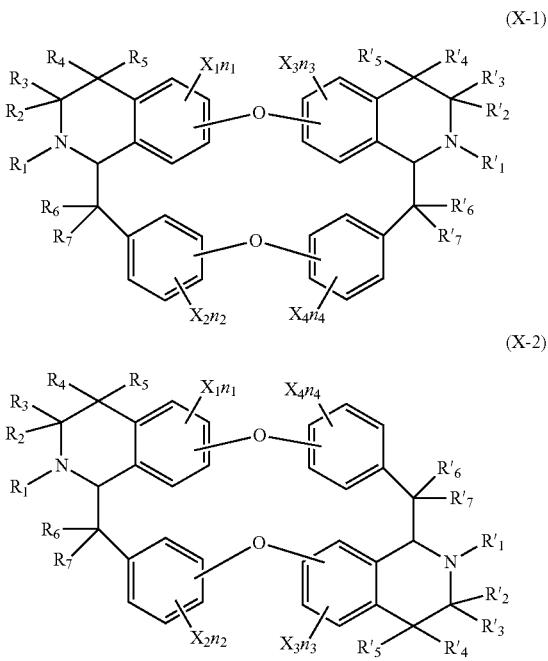

(X-1)

(X-2)

R₁ and R'₁ are each independently H or straight-chain or branched-chain alkyl having 1 to 10 carbon atoms, R₂, R'₂, R₃, R'₃, R₄, R'₄, R₅, and R'₅ are each independently H, acyl, straight-chain or branched-chain alkyl having 1 to 10 carbon atoms, and the alkyl may be interrupted by an O, N, or S heteroatom, or R₂ and R₃, R₄ and R₅, R'₂ and R'₃, or R'₄ and R'₅ together represent O or S, R₆, R'₆, R₇, and R'₇ are each independently H, acyl, or straight-chain or branched-chain alkyl having 1 to 10 carbon atoms, and the alkyl may be interrupted by an O, N, or S heteroatom, or R₆ and R₇ or R'₆ and R'₇ together represent O or S, and X₁, X₂, X₃, and X₄ may be the same or different, and are each independently H, hydroxy, straight-chain or branched-chain alkyl having 1 to 10 carbon atoms, alkoxy, acyloxy, or sulfonyloxy, and each may further have a substituent, n₁ and n₃ are each independently an integer of 0 to 3, n₂ and n₄ are each independently an integer of 0 to 4, and these may be linked to each other to form a ring, wherein the culturing period is 50 days or more.

2. The production method according to claim 1, wherein the T cells or the NK cells are T cells or NK cells for immune cell therapy.

3. The production method according to claim 1, wherein the T cells or the NK cells are peripheral blood-derived, primary hematopoietic stem/progenitor cell-derived, or pluripotent stem cell-derived cells.

4. The production method according to claim 1, wherein the T cells are undifferentiated T cells.

5. The production method according to claim 1, wherein the T cells express at least one of CD4 and CD8.

6. The production method according to claim 1, wherein the T cells are cells selected from the group consisting of helper T cells, regulatory T cells, cytotoxic T cells, naive T cells, memory T cells, and terminal effector T cells.

7. The production method according to claim 6, wherein the regulatory T cells express FoxP3.

8. The production method according to claim 6, wherein the memory T cells are stem cell memory T cells, central memory T cells, or effector memory T cells.

9. The production method according to claim 1, wherein the NK cells are immature NK cells or mature NK cells.

10. The production method according to claim 1, wherein the bisbenzylisoquinoline alkaloid or the compound resulting from cleavage of one ether bond thereof or the pharmaceutically acceptable salt thereof is at least one selected from the group consisting of berbamine, (+)-berbamine, E6-berbamine, cepharanthine, and a pharmaceutically acceptable salt thereof.

11. The production method according to claim 1, wherein the concentration of the bisbenzylisoquinoline alkaloid or the compound resulting from cleavage of one ether bond thereof or the pharmaceutically acceptable salt thereof in the culture medium is from 0.1 nM to 10 μM.

12. The production method according to claim 1, wherein the culture medium further contains a MAPK cascade inhibitor.

13. The production method according to claim 1, wherein feeder cells are not contained in the culture medium.

* * * * *